(12) United States Patent
Wassie et al.

(10) Patent No.: US 12,259,393 B2
(45) Date of Patent: *Mar. 25, 2025

(54) PROTEIN SEQUENCING VIA COUPLING OF POLYMERIZABLE MOLECULES

(71) Applicant: Glyphic Biotechnologies, Inc., New York, NY (US)

(72) Inventors: Asmamaw Wassie, Leander, TX (US); Daniel Masao Estandian, Antioch, CA (US); Andrew John Price, San Mateo, CA (US); Boyang Hua, Oakland, CA (US); Joshua Young Cynming Yang, Richardson, TX (US); David Dodd, San Francisco, CA (US); Gerardo Fabian Delgado, Oakland, CA (US); Elaine Jean Su, Martinez, CA (US)

(73) Assignee: Glyphic Biotechnologies, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/627,030

(22) Filed: Apr. 4, 2024

(65) Prior Publication Data
US 2024/0337660 A1 Oct. 10, 2024

Related U.S. Application Data

(63) Continuation of application No. PCT/US2023/071456, filed on Aug. 1, 2023.
(60) Provisional application No. 63/394,475, filed on Aug. 2, 2022.

(51) Int. Cl.
*G01N 33/68* (2006.01)
*C12Q 1/68* (2018.01)
(52) U.S. Cl.
CPC .......... *G01N 33/6818* (2013.01); *C12Q 1/68* (2013.01)

(58) Field of Classification Search
CPC ............... G01N 33/68; G01N 33/6818; G01N 33/6821; G01N 33/6824; Y10T 436/143333; C12Q 1/68
(Continued)

(56) References Cited

U.S. PATENT DOCUMENTS

| 4,665,037 A | 5/1987 | Stolowitz |
| 5,254,475 A | 10/1993 | Bailey |

(Continued)

FOREIGN PATENT DOCUMENTS

| EP | 2272981 B1 | 1/2013 |
| EP | 2342359 B1 | 3/2015 |

(Continued)

OTHER PUBLICATIONS

Alfaro, J.A. et al., The emerging landscape of single-molecule protein sequencing technologies, Nature Methods, vol. 18, 6 (2021):604-617.

(Continued)

*Primary Examiner* — Maureen Wallenhorst
(74) *Attorney, Agent, or Firm* — Wilson Sonsini Goodrich & Rosati

(57) ABSTRACT

"The present disclosure provides methods and systems for sequencing proteins. One or more methods disclosed herein may use linkers having an amino acid-reactive group and an additional reactive moiety that may be used to couple a polymerizable molecule. The linker may couple to a polymerizable molecule and an amino acid of a peptide and a capture moiety via the polymerizable molecule, followed by cleavage of the amino acid from the peptide. Further processing and analysis may be conducted using, for example, nanopores or nanogaps."

30 Claims, 28 Drawing Sheets

Specification includes a Sequence Listing.

(58) Field of Classification Search
USPC ......... 436/86, 89, 94, 149, 150; 435/6.1, 7.1
See application file for complete search history.

(56) References Cited

U.S. PATENT DOCUMENTS

| | | |
|---|---|---|
| 8,105,846 B2 | 1/2012 | Bayley et al. |
| 8,426,807 B2 | 4/2013 | Stein |
| 8,557,529 B2 | 10/2013 | Polonsky et al. |
| 8,829,432 B2 | 9/2014 | Stein |
| 9,494,554 B2 | 11/2016 | Davis et al. |
| 9,558,319 B1 | 1/2017 | Lathrop |
| 9,566,335 B1 | 2/2017 | Emili et al. |
| 10,006,879 B2 | 6/2018 | Ervin et al. |
| 11,214,830 B2 | 1/2022 | Turner et al. |
| 11,499,190 B2 | 11/2022 | Davis et al. |
| 11,499,979 B2 | 11/2022 | Estandian et al. |
| 11,673,136 B2 | 6/2023 | Qing et al. |
| 2014/0273004 A1 | 9/2014 | Havranek et al. |
| 2015/0087526 A1* | 3/2015 | Hesselberth ............ G16B 30/10 435/23 |
| 2016/0032236 A1* | 2/2016 | Nivala ..................... C12Q 1/48 435/7.1 |
| 2017/0002053 A1 | 1/2017 | Julius et al. |
| 2018/0284125 A1 | 10/2018 | Gordon et al. |
| 2018/0299460 A1 | 10/2018 | Emili |
| 2018/0372752 A1 | 12/2018 | Emili et al. |
| 2019/0145982 A1* | 5/2019 | Chee .................. G01N 33/6803 435/6.11 |
| 2020/0217853 A1* | 7/2020 | Estandian ............... G01N 33/58 |
| 2020/0219590 A1* | 7/2020 | Reed .................. G01N 33/6824 |
| 2020/0284783 A1 | 9/2020 | Schmidt et al. |
| 2020/0348307 A1* | 11/2020 | Beierle .................. C12N 15/10 |
| 2020/0348308 A1 | 11/2020 | Chee et al. |
| 2021/0033591 A1 | 2/2021 | Ambroso et al. |
| 2021/0132076 A1 | 5/2021 | Marcotte et al. |
| 2021/0355483 A1 | 11/2021 | Chee et al. |
| 2021/0396762 A1 | 12/2021 | Chee et al. |
| 2023/0016396 A1* | 1/2023 | Gunderson .......... G01N 33/582 |
| 2023/0024319 A1 | 1/2023 | Heron et al. |
| 2023/0056532 A1 | 2/2023 | Gunderson et al. |
| 2023/0076975 A1 | 3/2023 | Anslyn et al. |
| 2023/0104998 A1* | 4/2023 | Estandian ............. G01N 33/533 436/89 |
| 2023/0213527 A1* | 7/2023 | Reed .................. G01N 33/6893 436/85 |

FOREIGN PATENT DOCUMENTS

| | | |
|---|---|---|
| EP | 2851433 B1 | 10/2017 |
| EP | 3526349 B1 | 3/2021 |
| EP | 3891300 A1 | 10/2021 |
| EP | 4070092 B1 | 8/2023 |
| KR | 102034304 B1 | 10/2019 |
| WO | WO-2013188841 A1 | 12/2013 |
| WO | WO-2017192633 A1 | 11/2017 |
| WO | WO-2018017914 A1 | 1/2018 |
| WO | WO-2019089846 A1 | 5/2019 |
| WO | WO-2019195633 A1 | 10/2019 |
| WO | WO-2020146325 A1 | 7/2020 |
| WO | WO-2020223000 A1 | 11/2020 |
| WO | WO-2021051011 A1 | 3/2021 |
| WO | WO-2022150659 A1 | 7/2022 |
| WO | WO-2022243692 A1 | 11/2022 |
| WO | WO-2023196642 A1 | 10/2023 |
| WO | WO-2024030919 A1 | 2/2024 |

OTHER PUBLICATIONS

Ang, Y. et al., Rational design of hybridization chain reaction monomers for robust signal amplification, Chemical Communications, vol. 22, (2016).

Bird, R.E. et al., Single-Chain Antigen-binding Proteins, Science, vol. 242, 4877 (1988):423-426.

Bloom, S. et al., Decarboxylative alkylation for site-selective bioconjugation of native proteins via oxidation potentials, Nature Chemistry, vol. 10, 2, (2018):205-211.

Cherf, G.M. et al., Automated forward and reverse ratcheting of DNA in a nanopore at 5-Å precision, Nat. Biotechnol., vol. 30, 4 (2012):344-348.

Estandian, D.M. et al., Enabling tools for the de-novo single molecule protein sequencing, (2021):1-85.

Extended European Search Report issued Sep. 13, 2022, in European Patent Application No. 20739125.1 (8 pages).

Grammel, M. et al., Chemical reporters for biological discovery, Nature Chemical Biology, vol. 9, 8 (2013):475-484.

Hong, J.M. et al., ProtSeq: Toward high-throughput, single-molecule protein sequencing via amino acid conversion into DNA barcodes, ScienceDirect, vol. 25, 1 (2021):103586.

Hunkapiller, T. et al., The growing immunoglobulin gene superfamily, Nature, vol. 323, 6083 (1986):15-16.

Huston, J.S. et al., Protein engineering of antibody binding sites: Recovery of specific activity in an anti-digoxin single-chain Fv analogue produced in *Escherichia coli*, PNAS, vol. 85, (1988):5879-5883.

Knight, Z.A. et al., Phosphospecific proteolysis for mapping sites of protein phosphorylation, Nat. Biotechnology, vol. 21, 9 (2003):1047-1054.

Krishna, O.D. et al., Protein- and Peptide-Modified Synthetic Polymeric Biomaterials, Biopolymers, vol. 94, 1 (2010):32-48.

Lanzavecchia, A. et al., The use of hybrid hybridomas to target human cytotoxic T lymphocytes, Eur. J. Immunol., vol. 17, (1987):105-111.

Li, Z. et al., Design and Synthesis of Minimalist Terminal Alkyne-Containing Diazirine Photo-Crosslinkers and Their incorporation into Kinase Inhibitors for Cell- and Tissue-Based Proteome Profiling, Angew. Chem., vol. 125, 33 (2013):8713-8718.

Liu, R. et al., Development and Applications of Topologically Segregated Bilayer Beads in One-bead One-compound Combinatorial Libraries, QSAR & Combinatorial Science, vol. 24, 10 (2005):1127-1140.

Margolis, S.A. et al., The hydrolysis of proteins by microwave energy, Journal of Automatic Chemistry, vol. 13, 3 (1991):93-95.

Wilbanks, B. et al., Phenoxy radical reactivity of nucleic acids: practical implications for biotinylation, Chembiochem, vol. 22, 8 (2021):1400-1404.

Xie, T. et al., Selective C-Terminal Conjugation of Protease-Derived Native Peptides for Proteomic Measurements, Langmuir, vol. 38, 30 (2022):9119-9128.

Xu, G. et al., Chemoenzymatic Labeling of Protein C-Termini for Positive Selection of C-Terminal Peptides, ACS Chem Biol., vol. 6, 10 (2011): 1015-1020.

Zhang, L. et al., Photoredox-Catalyzed Decarboxylative C-Terminal Differentiation for Bulk- and Single-Molecule Proteomics, ACS Chem. Biol., vol. 16, 11 (2021):2595-2603.

Zhu, T. et al., Enzymatic clickable functionalization of peptides via computationally engineered peptide amidase, Chinese Chemical Letters, vol. 29, 7 (2018):1116-1118.

Howorka, et al., Reading amino acids in a nanopore, Nature Biotechnology, 38(2):159-160, (2020).

Nookaew, et al., Detection and Discrimination of DNA Adducts Differing in Size, Regiochemistry, and Functional Group by Nanopore Sequencing. Chemical Research in Toxicology, 33(12):2944-2952, (2020).

Ouldali, et al., Electrical recognition of the twenty proteinogenic amino acids using an aerolysin nanopore, Nature Biotechnology, 38(2):176-181, (2020).

Wei, et al., Enabling nanopore technology for sensing individual amino acids by a derivatization strategy. Journal of Material Chemistry B., 8(31):6792-6797, (2020).

* cited by examiner

Samples

| Sample | Position 1 | Position 2 |
|---|---|---|
| Unmodified | Unmodified | Unmodified |
| Alkyne | Alkyne | Alkyne |
| Asp/Trp | Asp | Trp |
| Asp/Tyr | Asp | Tyr |
| Trp/Tyr | Trp | Tyr |

FIG. 10C

PROTEIN SEQUENCING VIA COUPLING OF POLYMERIZABLE MOLECULES

CROSS REFERENCE

This application is a continuation application of International Application PCT/US2023/071456, filed on Aug. 1, 2023, which claims the benefit to U.S. Provisional Application No. 63/394,475, filed Aug. 2, 2022, which is incorporated herein by reference in its entirety.

SEQUENCE LISTING

The instant application contains a Sequence Listing which has been submitted electronically in XML file format and is hereby incorporated by reference in its entirety. Said XML copy, created on May 29, 2024, is named 60652_705_301.xml and is 11,977 bytes in size.

BACKGROUND

Technological improvements in the analysis and characterization of biological molecules have proven to be critical in understanding biological and pathological mechanisms, which has implications in disease diagnosis and modeling, development of therapeutics and treatment, and improving health outcomes. Among these technological improvements, nucleic acid sequencing has emerged as an important tool for genomic and transcriptomic analysis of biological samples.

Protein signaling underpins a variety of cellular processes and serve important functions in viruses, cells, and living organisms. However, current technologies for studying proteins are limited in selectivity, sensitivity, throughput, or require a priori knowledge. As such, new approaches for characterizing and analyzing proteins is needed.

SUMMARY

Recognized herein is a need for technologies for studying proteins de novo, with improved accuracy and in a high-throughput format. The use of nanopores in protein or peptide sequencing through conventional methods faces challenges. Peptide or protein translocation through a nanopore and subsequent readout is hindered by protein characteristics: proteins are folded and are not uniformly charged, and the tight intramolecular spacing of amino acids means many amino acids enter the nanopore simultaneously, leading to superimposed signals that are difficult to resolve from one another. Provided herein are systems, compositions, kits, and methods for analyzing proteins that address the abovementioned needs. A method of the present disclosure may comprise attaching a plurality of polymerizable molecules to amino acids of a peptide via an intramolecular expansion process and analyzing the polymerizable molecule-amino acid conjugates. One or more processes described herein may involve sequencing via a nanopore or nanogap, allowing for identification of individual amino acids of the peptide in the order in which they appear or occur in the peptide.

In some embodiments, the present disclosure provides systems for and methods of sequencing a peptide at single-amino acid resolution, the methods comprising: (a) providing the peptide, a capture moiety comprising a first nucleic acid molecule, a linker, and a second nucleic acid molecule; (b) coupling the linker to a terminal amino acid of the peptide; (c) coupling the linker to the second nucleic acid molecule; (d) coupling the first nucleic acid molecule of the capture moiety to the second nucleic acid molecule; (e) cleaving the terminal amino acid from the peptide to yield an amino acid-linker-capture moiety (AALC) complex; (f) providing an additional linker comprising a third nucleic acid molecule, wherein the additional linker is capable of coupling to an additional amino acid of the peptide; (g) coupling the additional linker to the additional amino acid, thereby generating an additional amino acid-linker complex; (h) coupling the additional amino acid-linker complex to the AALC complex; (i) cleaving the additional amino acid, thereby generating a stacked AALC complex; (j) translocating the stacked AALC complex through a nanopore or a nanogap; (k) during (j), measuring a current signal; and (l) using the measured current signal to determine an identity of the terminal amino acid and the additional amino acid, thereby sequencing the peptide.

In some embodiments, the linker comprises a reactive moiety. In some embodiments, the second nucleic acid molecule comprises an additional reactive moiety capable of reacting with the reactive moiety of the linker, and wherein the coupling of (c) comprises reacting the reactive moiety with the additional reactive moiety. In some embodiments, the second nucleic acid molecule comprises an additional linker comprising the additional reactive moiety, wherein the additional linker comprises a modified nucleobase and the additional reactive moiety comprises a click chemistry moiety. In some embodiments, the capture moiety is affixed to a substrate. In some embodiments, the substrate is substantially planar. In some embodiments, the substrate is a bead.

In some embodiments, the capture moiety is coupled to the peptide.

In some embodiments, the first nucleic acid molecule or the second nucleic acid molecule comprises a DNA molecule, an RNA molecule, an XNA molecule, or modified variant thereof. In some embodiments, the DNA molecule is single-stranded. In some embodiments, the coupling of (d) is performed using a ligase.

In some embodiments, at least a portion of the first nucleic acid molecule is complementary to at least a portion of the second nucleic acid molecule. In some embodiments, the coupling is performed by hybridizing the at least the portion of the first nucleic acid molecule to the at least the portion of the second nucleic acid molecule.

In some embodiments, the coupling of (d) is performed using a splint oligonucleotide, wherein the splint comprises a first sequence complementary to at least a portion of the first nucleic acid molecule and a second sequence complementary to at least a portion of the second nucleic acid molecule.

In some embodiments, the first nucleic acid molecule of the capture moiety comprises a nucleic acid barcode molecule.

In some embodiments, the nucleic acid barcode molecule identifies the peptide.

In some embodiments, the terminal amino acid is an N-terminal amino acid.

In some embodiments, (b) occurs before (c). In some embodiments, (c) occurs before (b).

In some embodiments, the method further comprises repeating (f)-(i) to generate the stacked AALC complex. In some embodiments, the translocating of (j) occurs at a temperature below ambient temperature. In some embodiments, the second nucleic acid molecule comprises a nucleic acid barcode molecule that comprises temporal information. In some embodiments, the capture moiety comprises a cleavable moiety. In some embodiments, the linker is a bifunctional linker. In some embodiments, the linker comprises an amino acid reactive group and a click chemistry moiety.

In some embodiments, the cleaving of (e) or (i) is performed using treatment with acid. In some embodiments, the acid is a Lewis acid.

In some embodiments, the peptide is derived from a biological sample.

In some embodiments, the terminal amino acid comprises a post-translational modification or a non-standard amino acid, and (1) comprises identifying the post-translational modification or the non-standard amino acid.

In some embodiments, steps (a)-(i) of the method described herein are performed in absence of a substrate.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 10C shows a table of example amino acid types comprised by the model stacked amino acid-linker-polymerizable molecule complexes.

DETAILED DESCRIPTION

Figure 1:
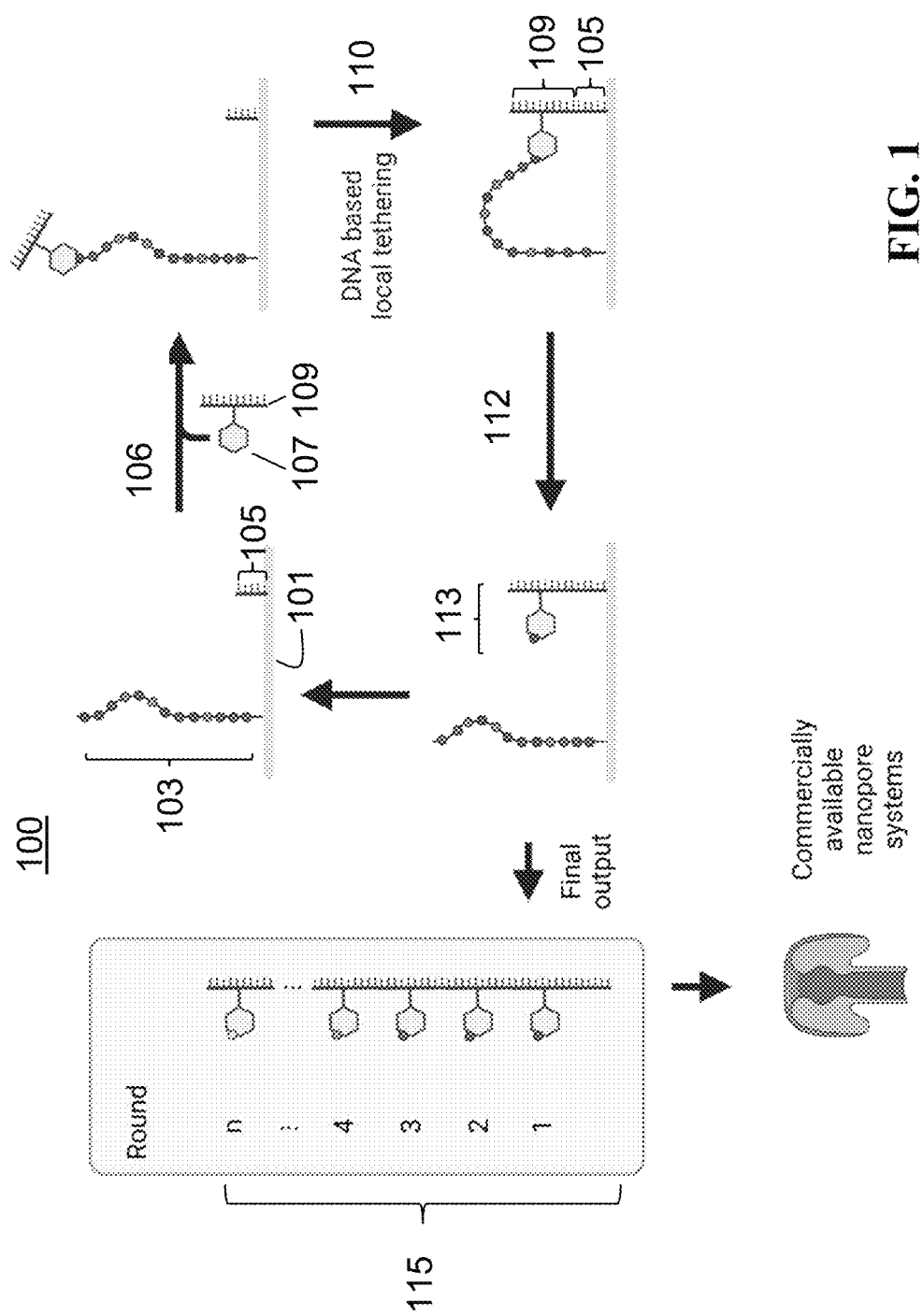
FIG. 1 schematically illustrates an example workflow for peptide sequencing disclosed herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to +20%, preferably up to +10%, more preferably up to ±5%, and more preferably still up to +1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

As used herein, the term "protein" generally refers to a molecule comprising two or more amino acids joined by a peptide bond. A protein may also be referred to as a "polypeptide", "oligopeptide", or "peptide". A protein can be a naturally occurring molecule, or a synthetic molecule. A protein may include one or more non-natural amino acids, modified amino acids, or non-amino acid linkers. A protein may contain D-amino acid enantiomers, L-amino acid enantiomers or both. Amino acids of a protein may be modified naturally or synthetically, such as by post-translational modifications or by chemical modification. In some circumstances, different proteins may be distinguished from each other based on different genes from which they are expressed in an organism, different primary sequence length or different primary sequence composition. Proteins expressed from the same gene may nonetheless be different proteoforms, for example, being distinguished based on non-identical length, non-identical amino acid sequence or non-identical post-translational modifications. Different proteins can be distinguished based on one or both of gene of origin and proteoform state.

As used herein, the term "peptide" may refer to any short, single peptide chain. A peptide may be no more than about 100, 95, 90, 85, 80, 75, 70, 65, 60, 55, 50, 45, 40, 35, 30, 25, 20, 15, 10, 5, or less than about 5 amino acids in length. A peptide may have a known or unknown biological function or activity. Peptides can include natural, synthetic, modified, or degraded proteins or peptides, or a combination thereof.

As used herein, the term "single analyte" may refer to an analyte that is individually manipulated or distinguished from other analytes. A single analyte may comprise a biomolecule or a synthetic molecule. A single analyte may comprise a small molecule. A single analyte can be a single molecule (e.g., a single biomolecule such as a single protein, nucleic acid molecule, affinity reagent, lipid, carbohydrate, etc.), a single complex of two or more molecules (e.g., a multimeric protein having two or more separable subunits, a single protein attached to a nucleic acid molecule or a single protein attached to an affinity reagent), a single particle, or the like. Reference herein to a "single analyte" in the context of a composition, system or method herein does not necessarily exclude application of the composition, system or method to multiple single analytes that are manipulated or distinguished individually, unless indicated contextually or explicitly to the contrary.

As used herein, "polypeptide" refers to two or more amino acids linked together by a peptide bond. The term "polypeptide" includes proteins that have a C-terminal end and an N-terminal end as generally known in the art and may be synthetic in origin or naturally occurring. As used herein "at least a portion of the polypeptide" refers to 2 or more amino acids of the polypeptide. A polypeptide may comprise one or more peptides. Optionally, a portion of the polypeptide includes at least: 1, 5, 10, 20, 30 or 50 amino acids, either consecutive or with gaps, of the complete amino acid sequence of the polypeptide, or the full amino acid sequence of the polypeptide.

As used herein, "affixed" refers to a connection between a polypeptide and a substrate such that at least a portion of the polypeptide and the substrate are held in physical proximity. The term "affixed" encompasses both an indirect or direct connection and may be reversible or irreversible, for example the connection is optionally a covalent bond or a non-covalent bond.

As used herein, the term "sample" refers to a collected substance or material that comprises or is suspected to comprise one or more analytes of interest (e.g., biomolecules, e.g., polypeptides). A sample may be modified for purposes such as storage or stability. A sample may be naturally occurring or synthetic. A sample may be processed to separate or remove unwanted fractions or impurities from the analyte(s) of interest. A sample may be enriched or purified. For example, a sample may comprise a fraction of a separation process (e.g., chromatography, fractionation, electrophoresis, etc.). Alternatively, a sample may not be subjected to processing that separates or removes any unwanted fractions or impurities from the analyte(s) of interest. A sample may be obtained from any suitable source or location, including from organisms, cells, tissues, cell preparations, cell-free compositions, the environment (e.g., air, water, dirt, soil, agriculture, soil, dust). A sample may be obtained from an organism or part of an organism, such as from a fluid, tissue, or cell. A sample may include biological and/or non-biological components. As used herein, the terms "biological sample" or "biological source" refer to a sample that is derived from a predominantly biological system or organism, such as one or more viral particles, cells (e.g. individualized cells), organelles (e.g. individualized organelles), tissues, bodily fluids, bone, cartilage, and exoskeleton. A biological sample may comprise a majority of biological material on a mass basis, excluding the weight of fluid within the sample. Biological samples may comprise one or more proteins, referred to herein as protein samples. Biological samples can be acquired from various sources, e.g., from a clinical patient sample, such as blood, serum, plasma, Cerebral Spinal Fluid (CSF), saliva, mucosal secretions, urine, lymph, perspiration, vaginal fluid, semen, etc. A biological sample may be processed to purify and retain one or more biomolecules (e.g., proteins, nucleic acids, carbohydrates, lipids, glycoproteins, lipoproteins, metabolites, etc.) from the biological sample. A biological sample (e.g., a protein sample) may be derived from cultured cells, which may be treated or untreated. A biological sample (e.g., a protein sample) can also result from tissue specimens, such as biopsy samples, which may optionally be processed to liberate biomolecules (e.g., proteins) contained therein. Tissue samples may also be derived from in vivo specimens, including fresh, frozen, acute, and fixed tissues.

As used herein, the terms "antibody" and "immunoglobulin" may generally refer to proteins that can recognize and bind to a specific antigen. An antibody or immunoglobulin may refer to an antibody isotype, fragments of antibodies including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a fluorophore, radioisotope, enzyme (e.g., a peroxidase) which generates a detectable product, fluorescent protein, nucleic acid barcode sequence, and the like. The antibodies may be further conjugated to other moieties, such as members of specific binding pairs, e.g., biotin (member of biotin-avidin specific binding pair), and the like. Also encompassed by the terms are Fab', Fv, F(ab')2, and other antibody fragments that retain specific binding to antigen. Antibodies may exist in a variety of other forms including, for example, Fv, Fab, and (Fab)2, as well as bi-functional (i.e., bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., Immunology, Benjamin, N.Y., 2nd ed. (1984), and Hunkapiller and Hood, Nature, 323, 15-16 (1986), which are herein incorporated by reference).

"Binding" as used herein generally refers to a covalent or non-covalent interaction between two molecules (referred to herein as "binding partners", e.g., a substrate and an enzyme or an antibody and an epitope). Binding between binding partners may be specific or non-specific.

As used herein, "specifically binds" or "binds specifically" generally refers to an interaction between binding partners (e.g., a binding partner and a cognate molecule) such that the binding partners bind to one another, but do not bind to other molecules that may be present in the environment (e.g., in a biological sample, in tissue, in an in vitro assay) under a set of conditions. A specific binding interaction may entail a binding partner that binds to a cognate molecule. The specific binding interaction may entail the binding of the binding partner to its cognate molecule at a significantly or substantially higher level or with greater affinity as compared to the binding of the binding partner to a non-cognate molecule. A specific binding interaction may entail a first binding partner that has greater selectivity of binding to the cognate molecule as compared to a non-cognate molecule.

The terms "nucleic acid", "nucleic acid molecule", "oligonucleotide" and "polynucleotide" may be used interchangeably herein and generally refer to a polymeric form of naturally occurring or synthetic nucleotides, or analogs thereof, of any length. A nucleic acid molecule may comprise one or more deoxyribonucleotides, deoxynucleotide triphosphates, dideoxynucleotide triphosphates, ribonucleotides, hexitol nucleotides, cyclohexane nucleotides, or analogs or combinations thereof. A nucleic acid molecule may comprise, e.g., DNA, RNA, HNA, CeNA, and modified forms thereof. A nucleic acid molecule may comprise nucleotides that are linked by phosphodiester bonds. A nucleic acid molecule may have any two- or three-dimensional structure, and may perform any function, known or unknown. A nucleic acid molecule may be single stranded, double stranded, or partially double stranded. Non-limiting examples of polynucleotides include a gene, a gene fragment, exons, introns, messenger RNA (mRNA), transfer RNA, ribosomal RNA, noncoding RNA, small interfering RNA, short hairpin RNA, micro RNA, scaRNA, ribozymes, riboswitches, viral RNA, complementary DNA (cDNA), cosmid DNA, mitochondrial DNA, chromosomal or genomic DNA, viral DNA, recombinant polynucleotides, branched polynucleotides, plasmids, vectors, isolated DNA of any sequence, control regions, isolated RNA of any sequence, nucleic acid probes, nucleic acid adapters, and primers. The nucleic acid molecule may be linear, circular, or any other geometry. Examples of polynucleotide analogs include but are not limited to xeno nucleic acid (XNA), bridged nucleic acid (BNA), glycol nucleic acid (GNA), hexitol nucleic acid (HNA), cyclohexane nucleic acid (CeNA), peptide nucleic acids (PNAs), yPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

As used herein, the term "amino acid" generally refers to an organic compound that combines to form a protein or peptide. An amino acid generally comprises an amine group, a carboxylic acid group, and a side-chain specific to each amino acid, which serve as a monomeric subunit of a peptide. An amino acid may include the 20 standard, naturally occurring or canonical amino acids as well as non-standard amino acids. The standard, naturally-occurring or canonical amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, (3-amino acids, Homo-amino acids, Proline and Pyruvic acid derivatives, 3-substituted alanine derivatives, glycine derivatives, ring-substituted phenylalanine and tyrosine derivatives, linear core amino acids, and N-methyl amino acids.

As used herein, the term "amino acid type" generally refers to one of the standard, naturally-occurring or canonical amino acids, e.g., one member of the group consisting of Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), Tyrosine (Y or Tyr), derivatives thereof, and modified forms of any of the aforementioned amino acids. The term "amino acid type" may be used herein to distinguish a plurality of amino acids that comprise different side chain groups, rather than a plurality of amino acids that are identical (e.g., different positional amino acids of a single peptide that have the same side chain). An amino acid type may comprise a modified version of one of the standard, naturally-occurring or canonical amino acids e.g., post translational modifications, an epigenetic modification, or chemical or enzymatic modifications.

As used herein, the term "post-translational modification" refers to modifications that occur on a peptide subsequent to translation. A post-translational modification may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopanteteinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is C1-C4 alkyl). A post-translational modification also includes modifications, such as but not limited to those described above, of amino acids falling between the amino and carboxy termini. The term post-translational modification can also include peptide modifications that include one or more detectable labels. A post-translational modification may be naturally occurring or synthetic.

As used herein, the term "binding agent" refers to a molecule, e.g., a nucleic acid molecule, a peptide, a polypeptide, a protein, carbohydrate, a synthetic molecule, or a small molecule that binds to, associates with, unites with, recognizes, or combines with another molecule. The binding agent may bind to a macromolecule or a component or feature of a macromolecule. A binding agent may form a covalent association or non-covalent association with a molecule, a macromolecule, or a component or feature of a macromolecule. A binding agent may also be a chimeric binding agent, composed of two or more types of molecules, such as a nucleic acid molecule-peptide chimeric binding agent, a carbohydrate-peptide chimeric binding agent, or a lipid-peptide chimeric binding agent. A binding agent may be a naturally occurring, synthetically produced, or recombinantly expressed molecule. A binding agent may bind to a single monomer or subunit of a macromolecule (e.g., a single amino acid of a peptide) or bind to a plurality of linked subunits of a macromolecule (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may preferably bind to a chemically modified or labeled amino acid over a non-modified or unlabeled amino acid. For example, a binding agent may preferably bind to an amino acid that has been modified with an acetyl moiety, guanyl moiety, dansyl moiety, PTC moiety, DNP moiety, SNP moiety, etc., over an amino acid that does not possess such a moiety. A binding agent may bind to a post-translational modification of a peptide molecule. A binding agent may exhibit selective binding to a component or feature of a macromolecule (e.g., a binding agent may selectively bind to one of the 20 possible natural amino acid residues and with bind with very low affinity or not at all to the other 19 natural amino acid residues). A binding agent may exhibit less selective binding, where the binding agent is capable of binding a plurality of components or features of a macromolecule (e.g., a binding agent may bind with similar affinity to two or more different amino acid residues). A binding agent may comprise a tag, which may be coupled to the binding agent via a linker.

As used herein, the term "linker" generally refers to a molecule or moiety that is involved in joining two or more molecules. A linker may facilitate a covalent or noncovalent interaction of two or more molecules. A linker may be a crosslinker. The linker can be unifunctional, bifunctional, trifunctional, quadrifunctional, or polyfunctional. A linker can be or comprise a nucleotide, a nucleotide analog, an amino acid, a peptide, a polypeptide, or a non-nucleotide chemical moiety, such as an organic or inorganic compound. A linker may comprise a polymer, such as a polyethylene glycol (PEG), polyethylene, polypropylene, polyvinyl chloride, polystyrene or other organic or inorganic polymer. A linker may comprise one or more reactive ends, e.g., an amine-reactive group, a carboxyl-reactive group, a sulfhydryl-reactive group, a hydroxyl-reactive group, etc. Alternatively, a linker may not comprise a reactive end. In some examples, a linker may be used to join different molecule types, e.g., different biomolecule types such as a peptide with a nucleic acid molecule, a lipid with a peptide, a carbohydrate with a peptide, etc.; non-biomolecule types; or a biomolecule to a non-biomolecule. For example, a linker may be used to join a binding agent with a tag, a tag with a macromolecule (e.g., peptide, nucleic acid molecule), a macromolecule with a solid support, a tag with a solid support, etc. A linker may join two molecules via enzymatic reaction or chemistry reaction (e.g., click chemistry). A linker may join more than two molecules, e.g., via enzymatic or chemical reactions.

The term "conjugated" as used herein generally refers to a covalent or ionic interaction between two entities, e.g., molecules, compounds, or combinations thereof.

As used herein, the term "tag" generally refers to a molecule or moiety that is conjugated to a molecule. A tag may comprise a detectable label, e.g., a fluorophore or fluorescent protein, a radioactive isotope, an enzyme (e.g., a chromogenic or fluorescent protein, proteins that can catalyze chromogenic substrates), a mass tag, a hapten (e.g., biotin, digoxigenin, urushiol, fluorescein), a vibrational or FTIR tag (e.g., alkyne group). A tag may comprise a biomolecule, such as a nucleic acid molecule, a protein, a lipid, a carbohydrate, or a combination thereof. A tag may comprise one or more nucleic acid molecules, which may optionally encode information regarding the tag or the molecule onto which a tag is conjugated (e.g., a binding agent, such as an antibody). For example, a tag may comprise a nucleic acid barcode molecule. A tag may comprise an organic compound or an inorganic compound.

As used herein, the term "barcode" generally refers to an identifying feature that may be used to distinguish similar items. A barcode may comprise a nucleic acid molecule of about 2 to about 30 bases. A barcode may comprise a nucleic acid molecule of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150 or more bases, which may provide a unique identifier tag or origin information for a molecule (e.g., protein, polypeptide, peptide), a binding agent, a set of binding agents from a binding cycle, a sample molecule, a set of samples, molecules within a compartment (e.g., droplet, bead, partition or separated location), macromolecules within a set of compartments, a fraction of macromolecules, a set of macromolecule fractions, a spatial region or set of spatial regions, a library of macromolecules, or a library of binding agents. A barcode can be an artificial sequence or a naturally occurring sequence including peptides, proteins, protein complexes, carbohydrates, and synthetic polymeric materials. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. A population of barcodes may comprise error correcting barcodes. Barcodes can be used to computationally deconvolute sequence reads derived from an individual molecule, sample, library, etc. Barcodes may comprise multiplexed information, e.g., arising from different samples, compartments, individual molecules, etc. A barcode can also be used for deconvolution of a collection of molecules that have been distributed into small compartments for enhanced mapping. For example, rather than mapping a peptide back to the proteome, the peptide can be mapped back to its originating protein molecule or protein complex, a sample or partition from which it originated, etc. A barcode may comprise any useful sequence, including repeat sequences (e.g., a poly-A, poly-T, poly-C, poly-G region) or the barcode may comprise non-repeat sequences.

As used herein, a "sample barcode", also referred to as "sample tag" generally refers to a barcode molecule comprising identifying information of a sample from which a barcoded molecule derives.

As used herein, a "spatial barcode" generally refers to a barcode molecule comprising identifying information of a region of a 2-D or 3-D sample (e.g., a tissue section) from which a molecule originates or is derived. Spatial barcodes may be used for molecular pathology on tissue sections. A spatial barcode may allow for multiplex sequencing of a plurality of samples or libraries from tissue section(s).

As used herein, a "temporal barcode" generally refers to a barcode molecule comprising time-based information relating to the barcoded molecule. The types of time-based data encoded in a temporal barcode can include information such as a lifetime of a barcoded molecule, a time of collection of a sample, a time or duration since the beginning of an experiment or induction with a stimulus, information on the age of a cell or tissue, a sequence of interactions between molecules, a time or cycle or round (e.g., of an iterative process) in which the barcode molecule is provided, among others. It is possible for different types of barcodes (e.g., spatial, temporal, cell-specific) to be combined in one multiplexed barcode.

As used herein, the term "nucleic acid sequence" or "oligonucleotide sequence" generally refers to a contiguous string of nucleotide bases and may refer to the particular placement of nucleotide bases in relation to each other as they appear in an oligonucleotide. Similarly, the term "polypeptide sequence" or "amino acid sequence" refers to a contiguous string of amino acids and may refer to the particular placement of amino acids in relation to each other as they appear in a polypeptide.

A "nucleotide sequence" according to the present invention may include any polymer or oligomer of nucleotides such as pyrimidine and purine bases, such as cytosine, thymine, and uracil, and adenine and guanine, respectively and combinations thereof. The nucleotide sequence may comprise any deoxyribonucleotide, ribonucleotide, hexitol-nucleotide, cyclohexane-nucleotide, peptide nucleic acid component, and any chemical variants thereof, such as methylated, 7-deaza purine analogs, 8-halopurine analogs, hydroxymethylated or glycosylated forms of these bases, and the like. The polymers or oligomers may be heterogeneous or homogenous in composition and may be isolated from naturally occurring sources or may be artificially or synthetically produced. In addition, a nucleotide sequence may be DNA, RNA, HNA, CeNA or a mixture thereof, and may exist permanently or transitionally in single-stranded or double-stranded form, including homoduplex, heteroduplex, and hybrid states.

The terms "complementary" or "complementarity" refer to polynucleotides (i.e., a sequence of nucleotides) related by base-pairing rules. For example, the sequence "5'-AGT-3'," is complementary to the sequence "5'-ACT-3'". Complementarity may be "partial," in which only some of the nucleic acids' bases are matched according to the base pairing rules, or there may be "complete" or "total" complementarity between the nucleic acids. The degree of complementarity between nucleic acid strands can have significant effects on the efficiency and strength of hybridization between nucleic acid strands under defined conditions.

As used herein, the term "hybridization" is used in reference to the pairing of complementary nucleic acids. Hybridization and the strength of hybridization (e.g., the strength of the association between the nucleic acids) is influenced by such factors as the degree of complementary between the nucleic acids, stringency of the conditions involved, and the melting temperature of the formed hybrid. Hybridization methods involve the annealing of one nucleic acid to another, complementary nucleic acid, e.g., based on Watson-Crick base pairing.

As used herein, the term "proteomics" generally refers to quantitative and/or qualitative analysis of the proteome within a sample, such as biological sample, e.g., from cells, tissues, or bodily fluids. Proteomics may include the analysis of spatial distributions of proteins within a sample (e.g., cell and/or tissues). Proteomics may include studies of the dynamic state of the proteome, e.g., how one or more proteins change in time.

The terminal amino acid at one end of the peptide chain that has a free amino group may be referred to herein as the "N-terminal amino acid" (NTAA). The terminal amino acid at the other end of the chain that has a free carboxyl group may be referred to herein as the "C-terminal amino acid" (CTAA). The amino acids making up a peptide may be numbered in order, with the peptide being "n" amino acids in length. As used herein, in some instances, NTAA may be considered the nth amino acid (also referred to herein as the "n NTAA"). In such cases, the next amino acid is the n−1 amino acid, then the n−2 amino acid, and so on down the length of the peptide from the N-terminal end to C-terminal end. Alternatively, CTAA may be considered the nth amino acid (also referred to herein as the "n CTAA"). In such cases, the next amino acid is the n−1, then the n−2 amino acid, and so on down the length of the peptide from the C-terminal end to N-terminal end. An NTAA, CTAA, or both may be modified or labeled with a chemical moiety.

As used herein, the terms "determining," "measuring," "assessing," and "assaying" are used interchangeably and include both quantitative and qualitative determinations.

As used herein, the term "unique molecular identifier" or "UMI" generally refers to a molecule barcode comprising indexing information. A UMI may comprise a nucleic acid molecule of about 3 to about 150 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, or 150 bases) in length. A UMI may provide a unique identifier tag for each molecule (e.g., peptide, binding agent, a nucleic acid molecule) that comprises or is coupled to a UMI. A UMI may comprise a random sequence (e.g., a random N-mer).

As used herein, a "derivative" of a nucleic acid molecule generally refers to a nucleic acid molecule that is derived from an originating nucleic acid molecule. The derivative may have the same or substantially the same nucleotide sequence as the originating nucleic acid molecule, or the derivative may comprise a complement or partial complement as the originating nucleic acid molecule. A derivative may be the same type of nucleic acid (e.g., DNA or RNA) as the originating nucleic acid molecule, or the derivative may be a different type of nucleic acid (e.g., cDNA generated from an RNA molecule). A nucleic acid molecule derivative may display sequence identity as the originating nucleic acid molecule. The derivative nucleic acid molecule may also be subjected to additional processing from the originating nucleic acid molecule, e.g., chemical or enzymatic modification, splicing, ligation, polymerization, fragmentation, tagmentation (e.g., using a transposase), digestion, etc.

A derivative polypeptide or peptide may be derived from an originating polypeptide (or peptide). A derivative may comprise the same amino acid sequence as the originating polypeptide, or the sequence may be different. The derivative polypeptide may result from or be subjected to additional processing from the originating polypeptide, e.g., chemical or enzymatic modification. The derivative polypeptide may comprise one or more tags, nucleic acid molecules, barcode molecules, labels (e.g., detectable labels), fluorophores, probes, linkers, post-translational modifications, chemical protecting groups, or other chemical moieties.

As used herein, the term "compartment" generally refers to a physical area or volume that separates or isolates a subset of molecules from a sample of molecules. For example, a compartment may separate an individual cell from other cells, or a subset of a sample's proteome from the rest of the sample's proteome. A compartment may be an aqueous compartment (e.g., microfluidic droplet), a solid compartment (e.g., picotiter well or microtiter well on a plate, tube, vial, gel bead), or a separated region on a surface. A compartment may comprise one or more beads to which macromolecules may be immobilized.

As used herein, the term "solid support", "solid surface", or "solid substrate" or "substrate" refers to any solid material, including porous and non-porous materials, to which a molecule can be associated directly or indirectly. The molecule may be associated with the substrate by covalent or non-covalent interactions, or a combination thereof. A substrate may be two-dimensional (e.g., planar surface) or three-dimensional (e.g., gel matrix or bead). A solid support may comprise, in non-limiting examples, a bead, a microbead, an array, a glass surface, a silicon surface, a plastic surface, a filter, a membrane, nylon or other polymer, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, nitrocellulose, glass, gold, quartz, polystyrene, polyethylene vinyl acetate, polypropylene, polymethacrylate, polyethylene, polyethylene oxide, polysilicates, polycarbonates, Teflon, fluorocarbons, nylon, silicon rubber, polyanhydrides, polyglycolic acid, polylactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, polystyrene bead, a polymer bead, a methylstyrene bead, an agarose bead, an acrylamide bead, a solid core bead, a porous bead, a paramagnetic bead, a glass bead, or a controlled pore bead. A bead may be spherical or an irregularly shaped. A bead's size may range from nanometers, e.g., 100 nm, to millimeters, e.g., 1 mm. In certain embodiments, beads range in size from about 0.2 micron to about 200 microns, or from about 0.5 micron to about 5 microns. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μm in diameter. In certain embodiments, "a bead" solid support may refer to an individual bead or a plurality of beads.

As used herein, "sequencing" generally refers to determining the order of: (A) nucleotides (base sequences) in a nucleic acid sample, e.g., DNA or RNA; or determining the order of (B) amino acids in all or part of a polymer, such as a protein, peptide, or other multimeric molecule. Many techniques are available, such as Sanger sequencing or High Throughput Sequencing technologies (HTS). Sanger sequencing may involve sequencing via detection through (capillary) electrophoresis, in which up to 384 capillaries may be sequence analyzed in one run. High throughput sequencing involves the parallel sequencing of thousands or millions or more sequences at once. HTS can be defined as Next Generation sequencing (NGS), i.e. techniques based on solid phase pyrosequencing or as Next-Next Generation sequencing based on single nucleotide real time sequencing (SMRT). HTS technologies are available such as offered by Roche, lllumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, nanopore sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, ThermoFisher, and Roche, including formats such as parallel bead arrays, sequencing by synthesis, sequencing by ligation, capillary electrophoresis, electronic microchips, "biochips," microarrays, parallel microchips, and single-molecule arrays, as reviewed by Service (Science 311:1544-1546, 2006).

As used herein, "analyzing" the macromolecule means to quantify, characterize, distinguish, or a combination thereof, all or a portion of the components of a molecule (e.g., a macromolecule, a biological molecule such as a protein, amino acid, nucleic acid molecule, etc.). For example, analyzing a peptide, polypeptide, or protein may comprise determining all or a portion of the amino acid sequence (contiguous or non-continuous) of the peptide. Analyzing a macromolecule may include partial identification of a component of the macromolecule. For example, partial identification of amino acids in a protein sequence can identify an amino acid in the protein as belonging to a subset of possible amino acids. Analysis may be performed sequentially, e.g., beginning with analysis of the n NTAA, and then proceeding to the next amino acid of the peptide (i.e., n–1, n–2, n–3, and so forth). In such instances, sequencing may be performed by cleavage of the n NTAA, thereby converting the n–1 amino acid of the peptide to an N-terminal amino acid (referred to herein as the "n–1 NTAA"). Similarly, analysis of a peptide may begin from C-terminus towards the N-terminus with each round of cleavage from the C-terminus creating a new CTAA. Cleavage of the n CTAA converts the n–1 amino acid of the peptide to a C-terminal amino acid, referred to herein as an "n–1 CTAA". Analyzing the peptide may also include determining a presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

As used herein, the term "array" generally refers to a population of molecules that is attached to one or more solid supports such that the molecules at one address can be distinguished from molecules at other addresses. An array can include different molecules that are each located at different addresses on a solid support. Alternatively, an array can include separate solid supports each functioning as an address that bears a different molecule, wherein the different molecules can be identified according to the locations of the solid supports on a surface to which the solid supports are attached, or according to the locations of the solid supports in a liquid such as a fluid stream. The molecules of the array can be, for example, nucleic acids such as SNAPs, polypeptides, proteins, peptides, oligopeptides, enzymes, ligands, or receptors such as antibodies, functional fragments of antibodies or aptamers. The addresses of an array can optionally be optically observable, and, in some configurations, adjacent addresses can be optically distinguishable when detected using a method or apparatus set forth herein.

As used herein, the term "functionalized" refers to any material or substance that has been modified to include a functional group. A functionalized material or substance may be naturally or synthetically functionalized. For example, a polypeptide can be naturally functionalized with a phosphate group, oligosaccharide (e.g., glycosyl, glycosylphosphatidylinositol or phosphoglycosyl), nitrosyl, methyl, acetyl, lipid (e.g., glycosyl phosphatidylinositol, myristoyl or prenyl), ubiquitin or other naturally occurring post-translational modification. A functionalized material or substance may be functionalized for any given purpose, including altering chemical properties (e.g., altering hydrophobicity or changing surface charge density) or altering reactivity (e.g., capable of reacting with a moiety or reagent to form a covalent bond to the moiety or reagent).

As used herein, the term "click reaction," "click chemistry," or "bioorthogonal reaction" refers to single-step, thermodynamically favorable conjugation reaction utilizing biocompatible reagents. A click reaction may utilize no toxic or biologically incompatible reagents (e.g., acids, bases, heavy metals) or generate no toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kiloJoules/mole (kJ/mol), −10 kJ/mol, −25 kJ/mol, −50 kJ/mol, −100 kJ/mol, −200 kJ/mol, −300 kJ/mol, −400 kJ/mol, or less than −500 kJ/mol. Exemplary bioorthogonal and click reactions are described in detail in WO 2019/195633A1, which is herein incorporated by reference in its entirety. Exemplary click reactions may include metal-catalyzed azide-alkyne cycloaddition, strain-promoted azide-alkyne cycloaddition, strain-promoted azide-nitrone cycloaddition, strained alkene reactions, thiolene reaction, Diels-Alder reaction, inverse electron demand Diels-Alder reaction, [3+2] cycloaddition, [4+1] cycloaddition, nucleophilic substitution, dihydroxylation, thiolyne reaction, photoclick, nitrone dipole cycloaddition, norbornene cycloaddition, oxanobomadiene cycloaddition, tetrazine ligation, and tetrazole photoclick reactions. Exemplary functional groups or reactive handles utilized to perform click reactions may include alkenes (e.g., linear alkenes or cyclic alkenes such as trans-cyclooctene (TCO)), alkynes (e.g., linear alkynes or cycloalkynes (e.g., cyclooctynes or derivatives thereof, e.g., aza-dimethoxycyclooctyne (DIMAC), symmetrical pyrrolocyclooctyne (SYPCO), pyrrolocyclooctyne (PYRROC), difluorocyclooctyne (DIFO), α,α-bis(trifluoromethyl)pyrrolocyclooctyne (TRIPCO), bicyclo[6.1.0]nonyne (BCN), dibenzocyclooctyne (DIBO), difluorinated cyclooctyne (DIFO), difluorobenzocyclooctyne (DIFBO), dibenzoazacyclo-octyne (DBCO), difluoro-aza-dibenzocyclooctyne (F2-DIBAC), biaryl-azacyclooctynone (BARAC), difluorodimethoxydibenzocyclooctynol (FMDIBO), difluorodimethoxydibenzocyclooctynone (keto-FMDIBO), and 3,3,6,6-tetramethylthiacycloheptyne (TMTH)), TMTH-sulfoximine (TMTHSI), azides, epoxides, amines, thiols, nitrones, isonitriles, isocyanides, aziridines, activated esters, and tetrazines, triazoles, and combinations, variations, or derivatives thereof. The click chemistry moieties may be subjected to conditions sufficient to react the first click chemistry moiety to the second click chemistry moiety, e.g., provision of metal catalysts, appropriate solvents, pH, temperature, ionic concentration, or light/energy, for any useful duration of time.

As used herein, the terms "group" and "moiety" are intended to be synonymous when used in reference to the structure of a molecule. The terms refer to a component or part of the molecule. The terms do not necessarily denote the relative size of the component or part compared to the molecule, unless indicated otherwise. The terms do not necessarily denote the relative size of the component or part compared to any other component or part of the molecule, unless indicated otherwise. A group or moiety can contain one or more atoms.

As used herein, "primers" generally refer to nucleic acid molecules which can prime the synthesis of a nucleic acid molecule (e.g., DNA or RNA). A primer may be single stranded. A primer may comprise one or more recognition sites for a protein (e.g., a polymerizing enzyme, a restriction enzyme, a cleaving enzyme, etc.) to bind to the primer or a primer hybridized to a template strand. A primer may comprise DNA, RNA, or other nucleic acid analogs or noncanonical bases (e.g., spacer moieties, uracils, abasic sites). A primer may optionally comprise any number of functional sequences such as sequencing primer sequences (e.g., P5 or P7 sequences), sequencing primer-binding sequences, read sequences (e.g., R1 or R2 sequences), restriction sites, transposition sites (e.g., mosaic end sequences), etc.

"Amplification" or "amplifying" generally refers to a polynucleotide amplification reaction, namely, a population of polynucleotides that are replicated from one or more starting sequences. Amplifying may refer to a variety of amplification reactions, including but not limited to polymerase chain reaction (PCR), linear polymerase reactions, nucleic acid sequence-based amplification, rolling circle amplification and similar reactions. An amplification reaction may generate an amplicon.

An "adapter" as referred to herein, generally refers to a short nucleic acid molecule (e.g., about 10 to about 100 base pairs in length). An adapter may comprise a short double-stranded DNA molecule. An adapter may be attached, e.g., via polymerization or ligation, to an end of a DNA fragments or amplicons. Adapters may comprise synthetic oligonucleotides, e.g., oligonucleotides that have nucleotide sequences which are at least partially complementary to each other. An adapter may have blunt ends, may have staggered ends (also referred to herein as a 3' or 5' "overhang sequence" or "sticky end", or a blunt end and a staggered end. Adapters may be attached (e.g., via ligation) to fragments to provide an adapter-ligated fragment; the adapter-ligated fragment may serve as a starting point for subsequent manipulation e.g., for amplification or sequencing. An adapter may be functionalized, e.g., conjugated with a tag, probe, detectable label, affinity capture reagent (e.g., biotin or streptavidin).

The term "translocating" and "translocation," as used herein, generally refers to the movement of a molecule through a medium (e.g., a gas, a liquid, or a solid). Translocation of a molecule may occur spontaneously (e.g., through diffusion, Brownian motion, etc.). Alternatively or in addition to, translocation of a molecule may occur with an application of force or pressure, e.g., using frictional force, tension force, a normal force, air resistance force, spring force, gravitational force, electrical force, magnetic force, acoustic force (e.g., acoustophoresis) etc. In some examples, translocation of a molecule may be achieved by application of pressure-driven flow or electrophoretic forces. Translocation may occur through a liquid or through a solid substrate (e.g., through a pore or gap).

As used herein, the abbreviations for the natural 1-enantiomeric amino acids are conventional and can be as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Unless otherwise specified, X can indicate any amino acid. In some aspects, X can be asparagine (N), glutamine (Q), histidine (H), lysine (K), or arginine (R). References to these amino acids are also in the form of "[amino acid] [residues/residues]" (e.g., lysine residue, lysine residues, leucine residue, leucine residues, etc.).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Protein Sequencing Via Coupling to Polymerizable Molecules

Provided herein are methods, systems, compositions, and kits for characterizing proteins. The methods, systems, compositions, and kits of the present disclosure provide for the analysis of individual amino acids of a protein, thereby providing information on the composition or sequence of amino acids in a protein (also referred to herein as "protein sequencing"). In some aspects, a method of the present disclosure comprises providing an analyte, such as an amino acid, coupled to a polymerizable molecule, and identifying the polymerizable molecule, the analyte (e.g., amino acid), or both. In some aspects, the methods, systems, compositions, and kits provided herein entail the use of nanoscale objects (e.g., nanopores or nanogaps) for identifying an amino acid, which may be coupled to a polymerizable molecule. Beneficially, the polymerizable molecule may alter or modulate a property of the amino acid, such that the amino acid is more accurately identifiable, e.g., while translocating adjacent to or through the nanoscale object. Accordingly, the methods, systems, and compositions disclosed herein provide a more facile and accurate approach to protein sequencing.

In one aspect of the present disclosure, provided herein is a method of processing a modified amino acid, comprising: providing the modified amino acid, in which the modified amino acid comprises a polymerizable molecule, and translocating the modified amino acid or derivative thereof through a nanopore or a nanogap. The method may further comprise measuring a signal from the nanopore or the nanogap and using the signal to determine the identity of the modified amino acid or derivative thereof. In some instances, the polymerizable molecule facilitates the translocation or modifies the translocation velocity of the modified amino acid through the nanopore or nanogap, which may render the modified amino acid more detectable as compared to an unmodified amino acid. In some instances, the translocation of the modified amino acid through the nanopore or nanogap may improve the measured signal (e.g., current blockade) or increase the signal-to-noise ratio of the measured signal as compared to an unmodified amino acid or an amino acid without a polymerizable molecule coupled thereto.

Modified amino acids: The modified amino acid or derivative thereof may originate from or be part of a protein or peptide; for example, the modified amino acid may comprise or be derived from an amino acid located at a terminus (N-terminus or C-terminus) of a peptide, or the modified amino acid may comprise or be derived from an amino acid located within the peptide. The modified amino acid may comprise a proteinogenic amino acid or derivative thereof with any number of modifications. Examples of modifications include, in non-limiting examples, chemical modifications (e.g., protecting groups), biological modifications (e.g., post-translational modifications, modifications introduced by enzymatic treatment or digestion), physical modifications (e.g., mutations introduced by irradiation, heat, etc.), and the like. In some instances, the modified amino acid or derivative thereof comprises or is coupled to a binding agent, such as an antibody, antibody fragment, nanobody, aptamer, peptide, a small molecule, an inorganic compound, a polymer, or any variations or combinations thereof. In some instances, the modified amino acid comprises a non-naturally occurring chemical modification. For example, the modified amino acid may comprise a protecting group, such as, in non-limiting examples, a methyl, formyl, ethyl, acetyl, t-butyl, anisyl, benzyl, tifluoroacetyl, N-hydroxysuccinimide, t-butyloxycarbonyl, benzoyl, 4-methyl benzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, or 2,2,5,7,8-pentamethylchroman-6-sulphonyl group. In some instances, the modified amino acid comprises a proteinogenic amino acid or derivative thereof that is coupled to a polymerizable molecule. In some instances, the modified amino acid comprises a proteinogenic amino acid or derivative thereof, a linker, and a polymerizable molecule.

The modified amino acid may comprise any useful modification. Modifications may be naturally-occurring (e.g., post translational modifications) or non-naturally occurring, such as by labeling or tagging, e.g., with an amino acid- or amine-reactive agent or linker comprising the amino acid- or amine-reactive agent. Examples of amino acid- or amine-reactive agents include isothiocyanate (e.g., PITC, NITC), 1-fluoro-2,-4-dinitrobenzene (DNFB), dansyl chloride, 4-sulfonyl-2-nitrobfluorobenzene (SNFB), an acetylating agent, an acylating agent, an alkylating agent, a guanidination agent, a thioacetylation agent, a thioacylation agent, a thiobenzoylation agent, or a derivative or combination thereof. Alternatively, or in addition to, the one or more modified amino acids may comprise an adduct (e.g., a polymer such as PEG, a polymerizable molecule such as a nucleic acid molecule, a nanoparticle or nanotube, a peptide or protein), a lipid, a carbohydrate, a metabolite, a fluorophore, a hapten, a quencher, a tag (e.g., a fluorescent tag, a magnetic tag, a radioactive tag), a barcode, or other moiety. In some instances, a modified amino acid may comprise a modification that facilitates recruitment of an enzyme (or ribozyme or DNAzyme) to recognize or cleave a terminal amino acid, e.g., a NTAA or CTAA of a peptide. For example, a terminal amino acid of a peptide may be modified with a saccharide in order to recruit a lectin or lectin-bound protease. In another example, one or more modified amino acids may comprise or be coupled to a nucleic acid molecule having a first sequence that is complementary to a second sequence comprised by an oligo-bound protease. Hybridization of the first sequence to the second sequence may facilitate local recruitment of the protease to the amino acid to be cleaved. In yet another example, a peptide may be modified with phenylisothiocyanate (PITC), which may allow for recruitment and cleavage of the modified amino acid by an Edmanase. In some examples, modifications to amino acids may include epitope tags, which can facilitate binding of a binding agent to the modified amino acid. Examples of such epitope tags include fluorophores, nucleic acid molecules, peptides, haptens, polymers, chemical moieties, or other adduct molecule.

The methods described herein may further comprise generating the modified amino acid. In some instances, the modified amino acid comprises a proteinogenic amino acid or derivative thereof, a linker, and a polymerizable molecule. In one example, a peptide comprising a terminal amino acid may be contacted with a linker that comprises (i) first reactive moiety capable of reacting with an amino acid and (ii) a second reactive moiety. Prior to, during, or subsequent to the reaction of the first reactive moiety with the terminal amino acid, a polymerizable molecule comprising a third reactive moiety that is capable of reacting with the second reactive moiety may be provided. The second and third reactive moieties may comprise click chemistry moieties that can react with one another (e.g., azide and DBCO, azide and BCN, alkyne and DBCO, TCO and tetrazine, etc.). The reaction of the terminal amino acid with the linker and the linker to the polymerizable molecule may thus yield a modified amino acid comprising the terminal amino acid, the linker, and the polymerizable molecule. In some instances, cleavage of the terminal amino acid from the peptide may be performed, and the modified amino acid may comprise the cleaved product comprising the cleaved, and optionally derivatized, amino acid, the linker, and the polymerizable molecule.

The polymerizable molecule of the modified amino acid may alter a property of the amino acid coupled thereto as compared to an unmodified amino acid or an amino acid that does not have the polymerizable molecule coupled thereto; such an altered property (e.g., size, charge, aspect ratio, etc.) may influence the interaction or residence time of the modified amino acid with the nanopore or nanogap. In some embodiments, the polymerizable molecule alters the translocation velocity of the modified amino acid as the modified amino acid translocates through the nanopore or nanogap as compared to the translocation velocity of an unmodified amino acid. The translocation velocity of the modified amino acid may be higher or lower than the translocation velocity of the unmodified amino acid. In some instances, the translocation velocity of the modified amino acid is lower than that of the unmodified amino acid. For example, the translocation velocity of the modified amino acid may be decreased by at least about 0.10%, at least about 10%, at least about 2%, at least about 3%, at least about 4%, at least about 5%, at least about 6%, at least about 7%, at least about 8%, at least about 9%, at least about 10%, at least about 20%, at least about 50%, at least about 60%, at least about 70%, at least about 80%, at least about 90%, at least about 100%, at least about 200%, at least about 500%, at least about 1000%, at least about 5000% or greater. The translocation velocity of the modified amino acid may be decreased by a range of percentages, e.g., from about 5%-20%, from about 500%-3000%, etc. In some instances, the translocation velocity of the modified amino acid is non-uniform, e.g., may fall within a range of percentages by which the translocation velocity changes, and may depend on a property (e.g., size, charge, polarity, etc.) of the polymerizable molecule, the amino acid encompassed by the modified amino acid, the linker, or any other component of the molecule.

The change in translocation velocity of the modified amino acid, as compared to an unmodified amino acid (e.g., an amino acid without a coupled polymerizable molecule) may render the modified amino acid more detectable. For example, the polymerizable molecule coupled to an amino acid may decrease or alter the translocation velocity as it translocates through the nanopore or nanogap, such that a more accurate current reading may be obtained. Alternatively or in addition to, the polymerizable molecule may alter the charge, size, aspect ratio of the amino acid to which it is coupled, which can alter the current signature to improve detectability of the amino acid, the polymerizable molecule, or both. Alternatively or in addition to, the media (e.g., liquid, buffer, solution) in which the nanopore is in contact may comprise one or more agents that can alter or modulate the translocation velocity of the modified amino acid. For example, the media may comprise ions, salts, or other molecules which may selectively or preferentially alter the interaction between the modified amino acid and the nanopore, as compared to a non-modified amino acid.

In some instances, a measured signal-to-noise ratio (SNR) of the modified amino acid is higher as compared to the measured SNR of an unmodified amino acid (e.g., a proteinogenic amino acid, an amino acid that does not have a polymerizable molecule coupled thereto) as it translocates through the nanopore or nanogap. The SNR increase may be greater by at least about 0.1%, at least about 1%, at least about 2%, at least about 3%, at least about 4%, at least about 5%, at least about 6%, at least about 7%, at least about 8%, at least about 9%, at least about 10%, at least about 20%, at least about 50%, at least about 60%, at least about 70%, at least about 80%, at least about 90%, at least about 100%, at least about 200%, at least about 500%, at least about 1000%, at least about 5000% or greater. The SNR of the modified amino acid may be increased by a range of percentages, e.g., from about 5%-20%, from about$^{500}$%-1000%, etc.

In some instances, a measured signal (e.g., current blockade) of the modified amino acid as it translocates through the nanopore or nanogap is substantially different than that of an unmodified amino acid. In some instances, a measured signal of the modified amino acid as it translocates through the nanopore or nanogap is substantially different than that of the polymerizable molecule alone. The difference of the measured signal may be measured by any useful metric, e.g., fold-change, percentage change, absolute current measurement, signal-to-noise ratio, etc.

The polymerizable molecule may comprise any useful polymerizable moiety. The polymerizable moiety may comprise a naturally occurring or synthetic polymer (organic or inorganic) or biopolymer. The polymer may comprise one or more monomer types. In instances where more than one monomer type is used, the polymer may form an alternating copolymer structure, a periodic copolymer structure, a random copolymer structure, a block copolymer structure, a chained or grafted copolymer, or any other useful structure. The polymer may be linear or non-linear. The polymer may comprise polyethylene glycol (PEG), PEG-diacrylate, PEG-acrylate, PEG-thiol, PEG-azide, PEG-alkyne, polyacrylamide, agarose, collagen, fibrin, gelatin, chitosan, hyaluronic acid, alginate, polyvinyl alcohol, or another polymer.

In some examples, the polymerizable molecule comprises a biomolecule, e.g., a protein or peptide, a nucleic acid molecule, e.g., DNA or RNA, a carbohydrate or lipid chain. In some instances, the polymerizable molecule comprises a nucleic acid molecule, which can comprise any useful number and type of nucleotides, e.g., including canonical and noncanonical bases, and the number of nucleotides may be modulated based on the intended purpose. For example, the length of the nucleic acid molecules may be modulated to alter a property of the amino acid (e.g., volume, aspect ratio, charge, etc.) to which the polymerized molecule is tethered. The nucleic acid molecule may additionally or alternatively comprise any useful functional sequences, including but not limited to barcode sequences or other identifying sequences, UMI sequences, enzyme recognition sites (e.g., transposition sites, restriction sites), spacer sequences, sequencing primer sequences, read sequences, or primer sequences. The nucleic acid molecule may comprise canonical bases, noncanonical bases, naturally occurring bases, synthetic bases, abasic sites, or a combination thereof. In some instances, the modified amino acid or derivative thereof is generated using an iterative process, as described elsewhere herein; accordingly, the nucleic acid molecule may comprise information on the round or cycle number of the iterative process. In some instances, the nucleic acid molecule comprises a nucleic acid barcode molecule and may comprise useful information on the identity of the amino acid, temporal information, spatial information, etc.

The polymerizable molecule (e.g., a nucleic acid molecule) may be covalently or non-covalently coupled to an amino acid. The coupling may be performed using any suitable chemistries and reaction conditions and may comprise the use of a linker. In an example, a nucleic acid molecule may comprise a first reactive group, e.g., a first click chemistry moiety, as described elsewhere herein, and may be contacted with a linker comprising a second reactive group, e.g., a second click chemistry moiety that is able to react with the first reactive group. The linker may also comprise an additional reactive group that is able to tether to an amino acid (e.g., a terminal amino acid) and optionally, cleave the amino acid from a peptide. For example, the additional reactive group may be a thiocyanate conjugate, e.g., an isothiocyanate (ITC) such as phenyl isothiocyanate (PITC) or naphthylisothiocyanate (NITC), or an aldehyde group, e.g., ortho-phthalaldehyde (OPA), 2,3-naphthalenedicarboxyaldehyde (NDA), a guanidinylating agent, dinitrofluorobenzene (DNFB), dansyl chloride, or other amino acid-reactive group. The linker may be reacted with an amino acid of a peptide, e.g., the NTAA or CTAA. Use of such a linker comprising at least two reactive groups may allow for (i) tethering of the amino acid to the linker and (ii) tethering of the linker to the nucleic acid molecule (see, e.g., FIG. 4). In some instances, the linker may be provided pre-tethered to the nucleic acid molecule prior to contacting with the amino acid. In some instances, the conjugation of the polymerizable molecule to the amino acid, either via a linker or without a linker, may change the chemical structure of the amino acid. For example, if using a linker comprising an isothiocyanate moiety, the amino acid may be derivatized to a thiocarbamyl group (e.g., under alkaline conditions), a thiazolone group (e.g., under acid conditions), a thiohydantoin group, or other chemical moiety, thereby generating a modified amino acid comprising a polymerizable molecule coupled thereto.

Linkers: One or more linkers may be used to couple the polymerizable molecule to an amino acid or derivative thereof to thereby generate the modified amino acid. In some instances, the linker comprises a click chemistry moiety. The click chemistry moiety may comprise any suitable bioorthogonal moieties, as described elsewhere herein, e.g., alkenes, alkynes (e.g., alkyne, cycloalkynes such as DBCO and BCN), azides, epoxides, amines, thiols, nitrones, isonitriles, isocyanides, aziridines, activated esters, and tetrazines, and combinations, variations, or derivatives thereof.

The linker may be subjected to conditions sufficient to react the first click chemistry moiety to the second click chemistry moiety, e.g., provision of metal catalysts, appropriate solvents, pH, temperature, ionic concentration, or light/energy for any useful duration of time.

The linker may comprise an amino acid-reactive moiety. The amino acid-reactive moiety of the linker may be any useful moiety that enables the reactive moiety to conjugate to and optionally cleave an amino acid. In some examples, the third reactive moiety can react with a terminal amino acid (e.g., NTAA or CTAA). In such examples, the third reactive moiety may comprise any primary amine or carboxylic group reactive group, including but not limited to isocyanates, acyl azides, NHS esters, sulfonyl chlorides, aldehydes, glyoxals, epoxides, oxiranes, carbonates, aryl halides, imidoesters, carbodiimides, anhydrides, phenyl esters, isothiocyanates (e.g., phenyl isothiocyanate, sodium isothiocyanate, ammonium isothiocyanates (e.g., tetrabutylammonium isothiocyanate, tetrabutylammonium isothiocyanate), diphenylphosphoryl isothiocyanate), acetyl chloride, cyanogen bromide, carboxypeptidases, azide, alkyne, DBCO, maleimide, succinimide, thiol-thiol disulfide bonds, tetrazine, TCO, vinyl, methylcyclopropene, acryloyl, allyl, among others. Additional examples of amino acid reactive groups are provided in U.S. Pat. Pub. No. 2020/0217853, which is incorporated by reference herein in its entirety.

The linker may comprise any additional useful moieties. For example, the linker may comprise a releasable or cleavable moiety, which may facilitate removal of the amino acid-linker complex from the polymerizable molecule, or portion thereof, or from the substrate. Such a releasable or cleavable moiety may comprise, for example, a disulfide bond, which may be releasable by contacting with a reducing agent (e.g., DTT, TCEP). In some examples, the linker may couple to the polymerizable molecule via the releasable or cleavable moiety, alternatively or in addition to the coupling via click chemistry moieties. As such, the coupling between the polymerizable molecule and the linker may be reversible. The linker may additionally comprise any number of spacing moieties, e.g., polymers (e.g., PEG, PVA, polyacrylamide), aminohexanoic acid, nucleic acids, alkyl chains, etc. Such spacing moieties may increase the distance between any other moieties of the linker, e.g., the amino acid-reactive group and the polymerizable molecule-reactive group.

In some instances, the polymerizable molecule comprises a linker. The linker may be used, for instance, for coupling a reactive moiety to the polymerizable molecule, which reactive moiety can react with that of another linker. In one such example, a polymerizable molecule, e.g., nucleic acid molecule, may comprise a linker that comprises a click chemistry moiety. The linker comprising the click chemistry moiety may be coupled to the polymerizable molecule using any useful approach, e.g., by incorporation of a linker-conjugated nucleotide or nucleoside, and may be located at any useful position (e.g., at a 5' end, at a 3' end, in the center of the polymerizable molecule). For example, a click-functionalized nucleotide or nucleoside, e.g., ethynyl deoxyuridine, octadiynyl deoxyuridine, can be incorporated into the backbone of a DNA or RNA molecule. As such, the click chemistry moiety of the polymerizable molecule may then couple to another linker that comprises a complementary click chemistry moiety and also an amino acid reactive group (e.g., isothiocyanate, dansyl chloride, DNFB, etc.).

The linker may comprise any number of spacing moieties, e.g., alkyl chains, polymer spacers (e.g., PEG), nucleic acid or oligo spacers, or other useful spacing moieties which may be useful in modulating the size or molecular weight of the linker. For example, the linker may comprise at least 1, at least 2, at least 3, at least 4, at least 5, at least 6, at least 7, at least 8, at least 9, at least 10, or a greater number of spacing moieties (e.g., hydrocarbon units, PEG units, nucleotides or spacer sequences etc.). The linker may comprise at most about 100, at most about 10, at most about 9, at most about 8, at most about 7, at most about 6, at most about 5, at most about 4, at most about 3, at most about 2, or at most 1 spacing moieties. The linker may comprise any useful number of functional groups, e.g., for attachment to multiple molecules. The linker may comprise at least 1, at least 2, at least 3, at least 4, at least 5, at least 6, at least 7, at least 8, at least 9, at least 10, or a greater number of functional groups.

Nanopores Nanogaps: Characterization of the modified amino acid may be performed using nanoscale technologies such as nanopores, nanogaps, or nanochannels. In some instances, a nanopore, nanogap, or nanochannel may be provided on a membrane in an ionic solution. A signal may be measured from the nanopore, membrane, or surrounding solution. For example, a conductance, current, current blockage, or other parameter within the nanopore may be monitored as a function of time. As a molecule enters the nanopore, nanogap, or nanochannel, a change in the conductance, current, or other parameter may occur and provide information (e.g., size, charge, aspect ratio, volume) on the molecule. Each amino acid or modified amino acid, or a subset of amino acids or modified amino acids, may generate a unique signal that is distinguishable from other amino acids or modified amino acids. As such, the unique signal signatures may be assigned to the amino acids or modified amino acids in order to determine the identity of the amino acids, polymerizable molecules, or both.

In some instances, a modified amino acid may be analyzed numerous times, e.g., via translocation and measuring of a current or conductance of the modified amino acid, through the same or different nanopore or nanogap. For example, iterative reading of a modified amino acid may be beneficial in improving the accuracy of the reads or identification of the modified amino acid (or polymerizable molecule). In such cases, the modified amino acid may be translocated through one or more nanopores at least 2 times, at least 3 times, at least 4 times, at least 5 times, at least 6 times, at least 7 times, at least 8 times, at least 9 times, at least 10 times, at least 20 times, at least 50 times, at least 100 times, at least 200 times, or even greater. Alternatively, or additionally, the modified amino acid may be ratcheted back and forth within the nanopore, e.g., using a processive enzyme such as phi29 polymerase, e.g., as described in Cherf et al. 2012. *Nat. Biotechnol.* 30(4):344-348, which is incorporated by reference herein in its entirety.

The nanopore, nanogap, or nanochannel may be generated from an organic material, e.g., a pore-forming protein or a transmembrane protein. Such a protein may be naturally occurring, synthetic, or engineered. Examples of naturally occurring organic nanopores include wild-type aerolysin, alpha-hemolysin, mycobacterial porins (e.g., MspA porin), Phi29 connector channels, Fragaceatoxin C, Cytolysin A, Ferric hydroxyamate uptake component A, Curli specific gene G, outer membrane porin G, viral DNA packaging motors, etc. Alternatively or in addition to, the nanopore, nanochannel, or nanogap may comprise an engineered variant of a naturally occurring nanopore. In some embodiments, the nanopore, nanogap, or nanochannel is comprised of an inorganic material. For example, solid-state nanopores may be made from dielectric materials such as a silicon compound (e.g., silicon nitride, silicon dioxide), an aluminum compound (e.g., aluminum oxide), a titanium compound (e.g., titanium oxide), a molybdenum compound (e.g., molybdenum sulfate), hafnium, graphene, etc. The nanopore, nanochannel, or nanogap may assume any useful form factor or geometry, e.g., gaps or channels within membranes, capillaries, etc., and may be generated using any suitable process, e.g., ion-beam sculpting, electron beam exposure. The nanopore, nanochannel, or nanogap may comprise an elastomeric material.

In some instances, the nanopore, nanogap, or nanochannel is coupled to a protein. The protein may be a molecular motor, which may facilitate movement of the modified amino acid or portion thereof (e.g., the polymerizable material) through the nanopore. In a non-limiting example, the modified amino acid may comprise an amino acid coupled, optionally via a linker, to a nucleic acid molecule, and the nanopore may be coupled to a helicase or a molecule comprising helicase activity. The helicase may be used to translocate the nucleic acid molecule and the coupled amino acid through the nanopore. In some instances, the molecular motor may increase, decrease, or otherwise change the translocation velocity of the modified amino acid through the nanopore as compared to an unmodified amino acid. In other examples, the molecular motor may comprise a topoisomerase, a polymerase, a nuclease (e.g., endonucleases such as restriction endonucleases or Cas proteins, or exonuclease) an unfoldase, mitotic spindle protein (e.g., nuclear mitotic apparatus protein, kinesin, dynein), or other motor protein (e.g., myosin), a variant thereof, or other polymer-processing protein. In some instances, the protein comprises a protease or proteosome, which can enable "chop-n-drop" or cleaving of the modified amino acid or portion thereof prior to translocation in the nanopore.

Alternatively or in addition to, translocation of the molecules described herein (e.g., modified amino acids, polymerizable molecules, etc.) through a medium or through a nanopore or nanogap may be facilitated by application of a force. For example, a molecule may be translocated by application of pressure (e.g., pressure-driven flow), an electric field (e.g., via electrophoresis, electroosmotic flow, isoelectric focusing), a magnetic field (e.g., using a ferromagnetic fluid, magnetic particles), light (e.g., optoelectronics).

A commercially available nanopore system may be used in the methods described herein. For example, a nanopore system from Oxford Nanopore Technologies (ONT), such as the MinION, VolTRAX, GridION, PromethION, MinIT, Flongle, or Q-Line products may be used to identify and characterize the modified amino acids described herein.

Intramolecular Expansion: The modified amino acid or derivative thereof may be produced using an intramolecular expansion process, e.g., using one or more linkers and polymerizable molecules. In intramolecular expansion, individual amino acids, clusters of amino acids, or small peptides (e.g., a dipeptide, tripeptide, or quadripeptide) of a protein (e.g., a peptide or protein analyte) may be sequentially removed and re-tethered together, such that the distance between the individual amino acids or clusters of amino acids is increased. Beneficially, performing an intramolecular expansion process of one or more amino acids of a peptide may obviate or overcome several issues with nanopore sequencing of peptides. For instance, by increasing the spacing between amino acids, fewer amino acids may enter the nanopore at a given instance, thereby reducing the quantity of superimposed signals arising from the number of amino acids within the nanopore. Further, increasing the spacing between amino acids may disrupt intramolecular interactions that convolve the current blockade signal, thereby allowing for higher-accuracy signal output from the nanopore.

In an example, a method for intramolecular expansion may comprise providing a peptide comprising a plurality of amino acids, a linker (e.g., as described elsewhere herein), a polymerizable molecule (e.g., as described elsewhere herein), and a capture moiety. The linker may be configured to couple to (i) an amino acid (e.g., NTAA or CTAA) of the peptide and (ii) the polymerizable molecule. The method may further comprise contacting the linker with the amino acid and the polymerizable molecule. Alternatively, or in addition, the linker may be provided pre-tethered to the polymerizable molecule and subsequently reacted with the amino acid. The linker may couple to the amino acid of the peptide to generate an amino acid-linker complex. The amino acid-linker complex may then couple to the capture moiety via the polymerizable molecule. For example, the polymerizable molecule and the capture moieties may both comprise nucleic acid molecules, which may be coupled via hybridization, ligation, or both. In some instances, the method may further comprise, coupling the polymerizable molecule to the capture moiety, cleaving the amino acid from the peptide to yield an amino acid-linker-capture moiety (AALC) complex, and optionally repeating the process. In an example in which the process is repeated, an additional linker may be provided which is configured to couple to (i) an additional amino acid of the peptide (e.g., the n-I NTAA or n-I CTAA) and (ii) an additional polymerizable molecule. The method may further comprise contacting the additional linker with the additional amino acid to generate an additional amino acid-linker complex. The additional polymerizable molecule may be coupled to the linker prior to, during, or subsequent to the coupling of the linker to the additional amino acid. The additional polymerizable molecule may be configured to couple to the AALC complex (e.g., via the polymerizable molecule of the AALC complex). As such, in some examples, subsequent to generation of the additional linker-additional amino acid complex, the additional linker-additional amino acid complex may couple to the AALC complex, thereby generating a stacked AALC complex, and the additional amino acid may be cleaved from the peptide prior to, during, or subsequent to generation of the stacked AALC complex. A "modified amino acid" may thus refer to the amino acid-linker complex, the amino acid-linker-polymerizable molecule, the AALC complex, the stacked AALC complex (comprising two or more amino acids), or a cleaved AALC complex, or combinations or portions (e.g., just the comprised amino acid portion, just the amino acid-linker complex portion, etc.) thereof.

In some instances, intramolecular expansion of the peptide or protein may occur across a plurality of capture moieties. For instance, use of a substrate may facilitate intramolecular expansion of a substrate-bound peptide. For example, a substrate may be provided that comprises a plurality of capture moieties, and, in some instances, the capture moieties are located adjacent to the peptide or protein. A first amino acid (e.g., n NTAA or n CTAA) of the peptide or protein may be coupled to a first capture moiety (e.g., via a first linker and a first polymerizable molecule), a second amino acid (e.g., n-I NTAA or n-I CTAA) may be coupled to a second capture moiety (e.g., via a second linker and a second polymerizable molecule), and a third amino acid (e.g., n-2 NTAA or n-2 CTAA) may be coupled to a third capture moiety (e.g., via a third linker and third polymerizable molecule). In another example, a first amino acid (e.g., n NTAA) may be coupled to a first capture moiety, a second amino acid (e.g., n-I NTAA) may be coupled to the AALC complex (e.g., from the n NTAA), thereby generating a stacked AALC complex, and a third amino acid (e.g., n-2 NTAA) may be coupled to a second capture moiety. As will be appreciated, any number of amino acids (or modified amino acids) may be coupled to any number of capture moieties (or resultant AALC or stacked AALC complexes).

Capture Moieties: A capture moiety may couple to the amino acid, the linker, or the polymerizable molecule. The coupling of the amino acid, the linker, or the polymerizable molecule to the capture moiety may comprise a covalent interaction or a noncovalent interaction. The coupling may occur by interaction of binding pairs, e.g., biotin and avidin (or streptavidin), antigen or epitope and antibody or antibody fragment, cyclodextrins and small hydrophobic molecules (e.g., alkanes, benzene, polycyclics), cucurbiturils and adamantaneammonium or trimethylammoniomethyl ferrocene, cyclophane (e.g., calixarenes, cavitands, pillararenes, tetralactams), etc. In some embodiments, the coupling of the amino acid, the linker, or the polymerizable molecule to the capture moiety occurs through coupling of nucleic acid molecules (e.g., hybridization to one another or to a splint molecule).

In some instances, the capture moiety comprises an additional polymerizable molecule (e.g., a nucleic acid molecule or peptide). In one such example, both the polymerizable molecule of the modified amino acid and the capture moiety may comprise nucleic acid molecules. The nucleic acid molecules may be coupled to one another, e.g., via complementary base pairing directly or via a splint molecule and optional ligation.

The nucleic acid molecule of the capture moiety can comprise any naturally occurring, non-naturally occurring or engineered nucleotide base. For example, the nucleic acid molecule may comprise a pseudo-complementary base, a bridged nucleic acid, a xenonucleic acid, a locked nucleic acid, a peptide nucleic acid (PNA), a gamma-PNA, a morpholino, etc., as is described elsewhere herein. The capture moiety may comprise one or more functional sequences, including, but not limited to a priming sequence, sequencing sequence (e.g., P5 or P7 sequence), sequencing read sequence (e.g., R1 or R2 sequence), a mosaic end sequence, a transposase recognition sequence, a cleavage site (e.g., restriction site), a UMI, a blocking group, a spacer sequence, a barcode sequence, or other functional sequence. In some instances, the capture moiety comprises a cleavable or releasable moiety, e.g., a restriction enzyme recognition site, an abasic site, a uracil which can be cleaved using USER@ or uracil DNA glycosylase, a disulfide bond that can be releasable upon addition of a reducing agent, etc. In some instances, the capture moiety comprises a partial restriction site; e.g., the capture moiety may comprise a first partial restriction site and the polymerizable molecule may comprise a second partial restriction site; upon coupling or ligation of the polymerizable molecule to the capture moiety, the two partial restriction sites may generate a complete restriction site, such that the individual molecules (capture moiety and polymerizable molecule) are not cleavable by restriction digest individually but the ligated or coupled product is. In some instances, the capture moiety comprises a barcode sequence that comprises any useful information, e.g., the identity of the peptide that is to be analyzed, temporal information, spatial information, etc.

In some instances, the capture moiety is provided coupled to a substrate. In one example, the substrate comprises, one or more identical capture nucleic acid molecules; these identical capture nucleic acid molecules may act as a capture moiety for generating one or more AALC complexes, e.g., for a terminal amino acid, an n−1 amino acid, etc. In some instances, commercially available substrates, e.g., beads (e.g., DNA beads or barcoded beads), flow cells, or chips, e.g., Illumina® HiSeq, iSeq, MiniSeq, NextSeq, NovaSeq, etc. may be used as the substrates described herein. In some instances, the capture moieties may comprise additional useful sequences, e.g., primer sequences (e.g., P5 or P7 sequences) or read sequences (e.g., R1 or R2).

The capture moiety may be coupled to a substrate using any useful approach. In some instances, the capture moiety comprises a substrate-tethering group or linker or additional functional group. In some examples, the capture moiety comprises a nucleic acid molecule that comprises a substrate-tethering group, e.g., biotin, a click chemistry moiety such as an azide, that can couple to a substrate, e.g., a substrate comprising streptavidin or a complementary click chemistry moiety that can react with that of the substrate-tethering group. The capture moiety may additionally comprise a binding sequence, to which another nucleic acid molecule (e.g., a polymerizable molecule that is part of or coupled to the modified amino acid). In some instances, the capture moiety comprises a single-stranded oligonucleotide or a single-stranded region in which a complementary oligonucleotide can hybridize. The complementary oligonucleotide may comprise a detectable label (e.g., fluorophore) that allows for detection of the capture moiety.

Alternatively, the capture moiety may not be coupled to a substrate. For instance, the capture moiety may be directly coupled to the peptide that is to be analyzed or is undergoing intramolecular expansion. In such examples, the capture moiety may additionally comprise a nucleic acid barcode molecule that encodes the identity of the peptide or the originating sample or partition from which the peptide originated.

Cleaving: In some instances, the method further comprises cleaving the amino acid or modified amino acid from the peptide. The cleaving of the amino acid or modified amino acid may be achieved using any suitable mechanism, such as via application of a stimulus. The stimulus can be, for example, a chemical stimulus, a biological stimulus, a thermal stimulus (e.g., application of heat), a photo-stimulus, a physical or mechanical stimulus, or other type of stimulus or a combination of stimuli. In some instances, the stimulus comprises a chemical stimulus, e.g., a change in pH, application of an acid or base, addition of a lytic agent, initiating agent, radical-generating agent, reducing agent, etc. In some instances, the chemical stimulus comprises application of a Lewis acid (e.g., boron triflate, boron trifluoride etherate, boron trichloride, boron tribromide, boron triiodide, or scandium triflate). In some instances, the stimulus comprises a biological stimulus, e.g., enzyme (e.g., Edmanase, protease, endonuclease) or ribozyme or DNAzyme that can cleave or catalyze cleavage of the modified amino acid.

In some examples, the method may comprise using a linker comprising an amino acid reactive group (e.g., PITC) and coupling the amino acid reactive group of the linker with the amino acid and cleaving the amino acid from the peptide using a stimulus (e.g., change in pH, temperature). In an example, the linker comprises a PITC moiety may couple to an NTAA under mildly alkaline conditions to generate a phenylthiocarbamoyl (PTC) derivative of the NTAA, and cleavage of the NTAA from the peptide may be achieved using an Edman degradation reaction (e.g., application of an acid such as trifluoroacetic acid or boron triflate, optionally with heat), to generate a thiazolinone (ATZ) derivative or a phenylthiohydantoin (PTH) derivative. As described elsewhere herein, the linker may comprise a moiety or molecule (e.g., polymerizable molecule such as a nucleic acid molecule) that can also couple to the capture moiety such that the amino acid or modified amino acid may be coupled to the capture moiety, thereby generating the AALC complex.

Given the harsh reaction conditions of standard Edman degradation, the polymerizable molecules described herein (e.g., nucleic acid molecules, peptides, lipids) etc. may comprise alterations or modifications to render them more resistant to the reaction conditions. For example, nucleic acid molecules may comprise predominantly pyrimidines (e.g., thymines, cytosines, uracils) which are more resistant to acid degradation and heat as compared to purines (e.g., adenine and guanine). For example, a nucleic acid molecule may comprise at least 50%, at least 60%, at least 70%, at least 80%, at least 90%, or 100% thymines or cytosines. Alternatively or in addition to, canonical nucleotides may be substituted or may comprise acid-resistant nucleotide analogs, e.g., hexitol nucleic acids.

Alternative degradation chemistries may also be employed. Milder degradation under basic conditions for N-terminal amino acid removal can include the use of triethylamine acetate in acetonitrile or other solvent such as water, N, N-dimethylformamide (DMF), or a mixture of solvents. Alternatively, degradation may be achieved using a thioacylation approach, the use of milder acid reagents, e.g., trichloroacetic acid (pKa of 0.66) or dichloroacetic acid (pKa of 1.35), or alternative basic reaction conditions, e.g., using acid-base pairs such as N, N-Diisopropylethylamine (DIPEA), pyridine, acetic acid derivatives, etc.

C-terminal degradation strategies are also provided herein. C-terminal degradation may comprise Edman-like degradation approaches. C-terminal degradation may employ the use of activating reagents that react with the C-terminal carboxyl group of a peptide, and a derivatizing agent (e.g., a thiocyanate to generate a peptide-thiocyanate or peptide-thiohydantoin). Non-limiting examples of activating reagents include acetyl chloride and acetic anhydride. Alternatively, or in addition to, single-step C-terminal derivatization of a peptide to a peptidyl-thiohydantoin may be performed, e.g., using Schlack-Kumpf approach, in which a peptide is reacted with thiocyanic acid (e.g., in acetone) to generate a peptidyl-thiohydantoin. The peptide-thiohydantoin may be cleaved, e.g., using basic conditions, to generate an amino acid thiohydantoin and remaining peptide.

Cleavage of amino acids may also be achieved using enzymatic or enzyme-analog (e.g., ribozyme or DNAzyme) approaches. Example enzymatic cleavage may include the use of Edmanases (e.g., modified cruzain), aminopeptidases (e.g., Pfu aminopeptidase I, PhTET aminopeptidases, *P. horikoshii* aminopeptidases), metalloenzymatic aminopeptidases, acylpeptide hydrolases, tRNA synthetases, endopeptidases, carboxypeptidases, and the like. The enzymes or ribozymes or DNAzymes may be modified or engineered to recognize a modified amino acid, e.g., an amino acid that has a chemical moiety attached thereto (e.g., PITC, NITC, dansyl chloride, SNFB, DNP, SNP, biotin, streptavidin, nucleic acid molecules, lipids, carbohydrates, acetyl groups, acyl groups, guandinylation agents, etc.).

One or more reactions may be accelerated by application of energy or radiation, e.g., electromagnetic radiation. For example, degradation or cleavage of the terminal amino acid of a peptide may be facilitated by applying microwave energy to accelerate the reaction kinetics. For example, hydrolysis of proteins may be facilitated by application of microwave energy, e.g., as described in Margolis et al., 1991, *Journal of Automatic Chemistry*. Vol 13, No. 3, pp 93-95, which is incorporated by reference herein.

In some instances, more than one amino acid may be cleaved from the peptide per cleavage event. The cleaving may comprise cleaving 2 amino acids, 3 amino acids, 4 amino acids, 5 amino acids, 6 amino acids, 7 amino acids, 8 amino acids, 9 amino acids, 10 amino acids, or more. For example, the polymeric analyte may comprise a peptide comprising a plurality of amino acids, and single amino acids, di-peptides, tri-peptides, quadri-peptides, or larger may be cleaved in the methods described herein. In some instances, at most about 10 amino acids, at most about 9 amino acids, at most about 8 amino acids, at most about 7 amino acids, at most about 6 amino acids, at most about 5 amino acids, at most about 4 amino acids, at most about 3 amino acids, or fewer amino acids may be cleaved in a given cleavage event. In some instances, cleavage of greater than one amino acid may be mediated using an enzyme (e.g., Edmanase, protease) or ribozyme or DNAzyme that is capable of recognizing or cleaving more than a single amino acid.

Cleavage of the amino acid or modified amino acid may be conducted using a biological stimulus, such as an enzyme or ribozyme or DNAzyme. The enzyme can be any useful cleaving enzyme, e.g., a protease, such as an Edmanase, cruzain, a cleaving protein (e.g., ClpS, ClpX), Proteinase K, exopeptidase, aminopeptidase, diaminopeptidase, serine protease, cysteine protease, threonine protease, aspartic protease, aspartic protease, glutamic protease, metalloprotease, asparagine peptide lyase, pepsin, trypsin, pancreatin, Lys-C, Glu-C, Asp-N, chymotrypsin, carboxypeptidase (e.g., carboxypeptidase A, carboxypeptidase B, carboxypeptidase Y), SUMO protease, elastase, papain, endoproteinase, proteinase, TrypZean®, bromelain, collagenase, hyaluronase, thermolysin, ficin, keratinase, tryptase, fibroblast activation, enterokinase, chymotrypsinogen, chymase, clostripain, calpain, alpha-lytic protease, proline specific endopeptidase, furin, thrombin, subtilisin, genenase, PCSK9, cathepsin, prolidase, methionine aminopeptidase, cathepsin C, 1-cyclohexen-1-yl-boronic acid pinacol ester, pyroglutamate aminopeptidase, renin, kininogen, kallikrein, DPPIV/CD26, thimet oligopeptidase, prolyl oligopeptidase, leucine aminopeptidase, dipeptidylpeptidase, or other enzyme or protease, or a combination or variation (e.g., engineered mutant or variant) thereof. In some instances, the cleaving enzyme or ribozyme or DNAzyme may be configured or engineered to cleave a terminal amino acid or plurality of amino acids; alternatively, the cleaving enzyme or ribozyme or DNAzyme may be configured or engineered to cleave off-site at a non-terminal location of the peptide, e.g., at an internal amino acid at an n−1, n−2, n−3, n−4, n−5, n−6, n−7, n−8, n−9, n−10, etc. position, where n is the number of amino acids in the peptide.

In the instances of enzymatic cleavage, additional reagents may be provided to catalyze or induce the cleavage. For instance, metalloproteases, aminopeptidases, or exopeptidases may facilitate cleavage of an amino acid or plurality of amino acids in the presence of a catalyst, e.g., metal or metal ion (e.g., cobalt). Accordingly, a catalyst may be provided in order to facilitate the binding of the enzyme to an amino acid or the subsequent cleavage of the amino acid from the peptide. In some examples, cleavage may be mediated by an apo-enzyme, which is inactive in the absence of a metal catalyst of cofactor, and cleavage may be controlled by addition of metal or metal ions.

Other examples of cleaving stimuli include: a photo stimulus (e.g., application of UV, X-rays, gamma rays, or other wavelength of light), mechanical stimulus (e.g., sonication, high pressure, electromagnetic energy), thermal stimulus (e.g., application of heat), or chemical stimulus. In some instances, the peptide may comprise or be altered to comprise a cleavable or labile bond that can be cleaved upon application of the appropriate stimulus, e.g., disulfide bonds (e.g., cleavable upon application of a chemical stimulus such as a reducing agent), ester linkages (e.g., cleavable with a change of pH), a vicinal-diol linkage (e.g., cleavable with sodium periodate), a Diels-Alder linkage (e.g., cleavable upon application of heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNase)).

Similarly, in some instances, the capture moiety may be cleaved from the peptide or the substrate. The cleaving may occur at any useful or convenient step, e.g., after generation of the AALC complex or stacked AALC complex, after multiple iterations of the workflow to generate a multi-stacked AALC complex, etc. In some instances, cleavage of the capture moiety may occur subsequent to the formation of a multi-stacked AALC complex, and the cleaved product may be sequenced, e.g., using a nanopore.

FIG. 1 schematically illustrates an example workflow of generating a modified amino acid using an intramolecular expansion process, followed by nanopore sequencing. In such an example workflow 100, a peptide 103 and a capture moiety 105 are provided, which optionally are coupled to a substrate 101. The capture moiety 105 may comprise a first nucleic acid molecule (e.g., DNA molecule). In process 106, a linker 107 and polymerizable molecule 109, e.g., a second nucleic acid molecule, are provided. In some instances, the linker 107 is pre-tethered to the polymerizable molecule 109; alternatively, the linker 107 and the polymerizable molecule 109 may be provided separately. In process 106, the linker 107 may couple to an amino acid (e.g., NTAA) of the peptide 103 to generate an amino acid-linker complex. In process 110, the amino acid-linker complex may couple to the capture moiety 105. Coupling of the amino acid-linker complex to the capture moiety 105 may be mediated by the polymerizable molecule 109. Optionally, the amino acid-linker complex and the capture moiety may be covalently linked together (e.g., the polymerizable molecule 109 may be covalently linked to the capture moiety 105), using chemical (e.g., click chemistry) or enzymatic (e.g., a ligase) approaches. Alternatively, or in addition to, the polymerizable molecule 109 may comprise a first sequence that is complementary and may hybridize to a second sequence of the capture moiety 105 (not shown), or the polymerizable molecule 109 may be linked to the capture moiety 105 via a splint or bridge molecule, which may comprise sequences that are complementary to the first sequence of the polymerizable molecule 109 and the second sequence of the capture moiety 105 (not shown). In process 112, the amino acid may be removed or cleaved from the peptide 103 to generate an amino acid-linker-capture (AALC) complex 113, which comprises a modified amino acid (e.g., a NTAA that has been modified as a result of the cleavage from the peptide), the linker 107, the polymerizable molecule 109, and the capture moiety 105. Processes 106, 110, and 112 may be iterated and repeated any number of times ("rounds") using additional linkers 107 and polymerizable molecules 109, and tethering the additional polymerizable molecules together (e.g., tethering an additional polymerizable molecule to the polymerizable molecule of the AALC complex 113). Multiple rounds may continue until all or a subset of the amino acids in the peptide 103 are removed from the peptide and tethered together. For example, a modified amino acid derivative, such as a complex 115 comprising multiple modified amino acids may result from n rounds of the workflow 100 (e.g., iterations of processes 106, 110, and 112).

As described elsewhere herein, a modified amino acid may comprise an amino acid having one or more modifications. For example, with respect to FIG. 1, a modified amino acid may be used to refer to the amino acid-linker complex (e.g., resulting from process 106) or portion thereof (e.g., just the amino acid of the amino acid-linker complex), the amino acid-linker-polymerizable molecule complex, the amino acid-linker-polymerizable molecule-capture moiety complex (e.g., resulting from process 110) or portion thereof, the cleaved amino acid of the AALC complex 113 or portion thereof, or one of the amino acids of the complex 115 of AALC complexes (stacked AALC complex). It will be appreciated that the modified amino acid may comprise other additional modifications not depicted in FIG. 1, such as posttranslational modifications or chemical modifications (e.g., protecting groups), described elsewhere herein. In some instances, the modified amino acid comprises a derivatized amino acid. For instance, the linker may comprise a PITC moiety as the amino acid reactive group, and upon conjugation of PITC to an amino acid (e.g., NTAA) of a peptide under mildly basic conditions, a phenylthiocarbamoyl (PTC) derivative of the amino acid is generated. The PTC-derivatized amino acid may be treated with acid (e.g., TFA or a Lewis acid) to generate a cleaved cyclic 2-anilino-5(4)-thiazolinone (ATZ)-derivatized amino acid, leaving a new N-terminus on the remaining peptide. The ATZ-derivatized amino acid may be converted to a phenylthiohydantoin (PTH) derivative or PTC derivative.

A "derivative" of the modified amino acid may generally refer to a molecule that is derived from the modified amino acid. A derivative may be a product of a reaction (e.g., chemical, enzymatic) or interaction of the modified amino acid with another molecule. For example, referring to FIG. 1, the modified amino acid may be an amino acid of the amino acid-linker complex (e.g., resulting from process 106), and a derivative of the modified amino acid may refer to all or a portion of: (i) the amino acid-linker complex (e.g., resulting from the process 110) coupled to the capture moiety, (ii) the AALC complex 113, or (iii) the complex 115 of AALC complexes (stacked AALC complex). Further processing of the modified amino acid may optionally be performed to arrive at the "derivative thereof." For example, further chemical or enzymatic treatment, cleavage of the capture moiety, an extension or amplification reaction, removal from a substrate, physical processes such as mechanical shearing or fragmentation may be performed on the modified amino acid to obtain a derivative of the amino acid.

Substrates: One or more molecules described herein may be coupled to a substrate. The one or more molecules coupled to the substrate may be the same type of molecule or different types of molecules. For example, a capture moiety (e.g., a nucleic acid molecule) and a peptide may be coupled to the substrate, either via covalent or non-covalent interaction. The capture moiety and peptide can be coupled to the substrate using any suitable chemistry, e.g., click chemistry moieties (e.g., alkyne-azide coupling), photoreactive groups (e.g., benzophenone), 1-ethyl-3-(3-dimethylaminopropyl)carbodiimide hydrochloride (EDC) (e.g., to couple amino-oligos or peptides), N-hydroxysulfosuccinimide (NHS), Sulfo-NHS, or NHS-esters (e.g., to couple sulfhydryl oligos), maleimides, thiols, biotin-streptavidin interactions, cystamine, gluteraldehyde, formaldehyde, SMCC, Sulfo-SMCC, silane (e.g., amino silanes), combinations thereof, etc. In some instances, the substrate may be functionalized to comprise a coupling chemistry to couple the peptide or the capture moiety. In one non-limiting example, a substrate (e.g., bead or surface) may comprise an alkyne such as dibenzocyclooctyne (DBCO), which may be configured to react to an amine (e.g., DBCO-alcohol, DBCO-Boc), a carboyxl or carbonyl (e.g., DBCO, DBCO-silane), a sulfhydryl, etc. An azide-functionalized nucleic acid or protein may react with DBCO to link the nucleic acid or protein to the DBCO substrate. In other examples, linkers such as bifunctional linkers may be used to attach a molecule to a substrate; such bifunctional linkers may comprise the same reactive moiety on both ends or a different moiety at each end (e.g., heterobifunctional linker).

Referring again to FIG. 1, the complex 115 of AALC complexes (stacked AALC complex) may be further processed to prepare the complex 115 for further characterization, e.g., via sequencing. For example, in instances where the capture moiety 105 is tethered to a substrate 101, the complex 115 may be removed from the substrate. For instance, the capture moiety 105 may comprise a releasable or cleavable moiety, e.g., a restriction site that is recognized by a restriction enzyme, a chemically cleavable linkage, e.g., a disulfide bond, a photosensitive linkage that is cleavable upon application of a photostimulus, etc., as is described elsewhere herein. Alternatively, or in addition, the capture moiety 105 may comprise a primer binding site, such that stack of polymerizable molecules (e.g., nucleic acid molecules) may be copied or amplified, e.g., using a primer extension reaction, for downstream analysis or sequencing. Additional operations may be performed, such as purification or enrichment, cleanup, nucleic acid reactions (e.g., ligation, extension, amplification, tagmentation, restriction enzyme cleavage), fragmenting, barcoding, addition of adapters (e.g., sequencing adapters, read sequences, etc.), enzymatic treatment, etc.

Nanopore sequencing: the modified amino acid or derivative thereof may be subjected to nanopore sequencing to determine the identity of an amino acid (e.g., as one of the proteinogenic, naturally occurring amino acids) and optionally, the polymerizable molecule. The nanopore sequencing may be performed using a commercially available nanopore system, e.g., Oxford Nanopore Technologies, Genia Technologies, NobleGen, or Quantum Biosystem. Nanopore sequencing may be performed to determine the identity of different components of the modified amino acids; for example, a modified amino acid comprising a derivatized amino acid (e.g., a thiocyanate-conjugated amino acid or a thiocarbamyl, thiazolinone, or thiohydantoin derivative) coupled to a polymerizable molecule (e.g., a nucleic acid molecule) may be subjected to nanopore sequencing, which may output the identity of which amino acid type (e.g., which of the 20 proteinogenic amino acids or post-translationally modified amino acids) the modified amino acid comprises or is derived from and, optionally, the identity of individual monomers of the polymerizable molecule (e.g., the nucleic acid sequence of the nucleic acid molecule). In instances where the polymerizable molecule comprises a nucleic acid molecule that encodes additional information (e.g., comprises barcode sequences, UMIs, cycle information, spatial information etc.), the sequencing of both the derivatized amino acid and the nucleic acid molecules may generate multiplexed information.

Multiplexed sequencing: Beneficially, the use of nanopore sequencing to analyze a peptide using the methods provided herein may result in a streamlined process for generation of multiplexed data. For example, the methods provided herein may allow for identification of amino acid residues and the polymerizable molecules (e.g., identification of individual monomers, nucleic acid sequences of nucleic acid molecules). As described herein, a modified amino acid may comprise a polymerizable molecule (e.g., a nucleic acid molecule) and an amino acid or derivative thereof. The polymerizable molecule may comprise multiple types of information. For example, the polymerizable molecule, e.g., a nucleic acid molecule, may comprise sequences that encode cycle or other temporal information, as described above, as well as spatial information. In one such example, an array of peptides and capture moieties may be provided on a substrate. The array may comprise a plurality of individually addressable units, in which each (or a subset of) individually addressable units of the array comprises a peptide to be sequenced and a capture moiety. Linkers may be provided across the array, which may be capable of linking to an amino acid of the peptides. Prior to, during, or subsequent to the provision of the linkers, a plurality of polymerizable molecules may be provided. The plurality of polymerizable molecules may comprise spatial information (e.g., spatial barcode sequences) which uniquely identify the individually addressable units and thus the location of the array. Alternatively, or in addition to, the polymerizable molecules or capture moieties may comprise information on the peptide, e.g., a barcode that identifies the peptide, a partition, sample, population of cells, etc. from which the peptide originates. The polymerizable molecules or capture moieties may additionally comprise temporal information (e.g., a cycle barcode that indicates the round or iteration in which the polymerizable molecule or capture moiety is provided). Subsequent sequencing may be used to reveal the spatial or temporal information (e.g., the originating location in the array of a peptide or amino acid, the cycle or timing in which a polymerizable molecule or capture moiety is provided, etc.). Alternatively or in addition to, the capture moiety may comprise multiplexed information (e.g., a barcode sequence, e.g., for identification of the peptide or the sample or partition from which the peptide originated, spatial information, temporal information, a UMI, etc.).

Similarly, binding agents may be used, which can add additional multiplexed analytical approaches to peptide sequencing. The use of binding agents coupled to a modified amino acid may be useful in modulating the translocation of the modified amino acid through a nanopore. The binding agents may comprise additional information that can be read out using nanopore sequencing. For example, different binding agents may be used that recognize specific amino acid residues (or modified amino acids, or amino acid-linker complexes); the different binding agents, alone or in combination with the modified amino acids to which they are coupled, may each be associated with a unique current signature when translocated through the nanopore and thus may be useful in identifying particular residues. In some instances, the binding agents may further comprise additional coding information, e.g., via conjugated barcode molecules or detectable tags. For example, the binding agents may have a barcode nucleic acid molecule coupled thereto, which barcode may identify the binding agent or the binding partner of the binding agent (e.g., an amino acid residue). Alternatively or in addition to, the binding agents may comprise spatial or temporal information, as described above. Accordingly, when the modified amino acids comprising binding agents associated therewith are translocated through the nanopore, multiple sets of information may be obtained, e.g., spatial, temporal, encoded barcode information from the binding agent, the amino acid or modified amino acid, the polymerizable molecule, the capture moiety, or a combination thereof.

Advantageously, the methods provided herein may yield multiplexed information in a streamlined workflow that obviates the need for multiple analytical instruments. As such, obtaining multiplexed data may occur substantially simultaneously. For example, using nanopore sequencing, the identity of an amino acid (or modified amino acid) and the identity of a polymerizable molecule coupled thereto may be obtained on the order of at most about 5 minutes, about 1 minute, about 50 seconds, about 40 seconds, about 30 seconds, about 20 seconds, about 10 seconds, about 1 second, about 900 milliseconds, about 800 milliseconds, about 700 milliseconds, about 600 milliseconds, about 500 milliseconds, about 400 milliseconds, about 300 milliseconds, about 200 milliseconds, about 100 milliseconds, about 900 microseconds, about 800 microseconds, about 700 microseconds, about 600 microseconds, about 500 microseconds, about 400 microseconds, about 300 microseconds, about 200 microseconds, about 100 microseconds, about 900 nanoseconds, about 800 nanoseconds, about 700 nanoseconds, about 600 nanoseconds, about 500 nanoseconds, about 400 nanoseconds, about 300 nanoseconds, about 200 nanoseconds, about 100 nanoseconds, or less.

Arrays: The methods and systems provided herein may include the use of arrays, e.g., for massively parallel sample processing or sequencing. In an example, a substrate may comprise an array of individually addressable units comprising a plurality of peptide analytes. In some instances, a subset of the individually addressable units comprises a single peptide analyte. The individually addressable units may additionally comprise a single or plurality of capture moieties. In some instances, the subset of the individually addressable units comprising a single peptide each comprise at least one capture moiety. The array may be patterned (e.g., individually addressable units are arranged in a pattern), or they may be random (e.g., individually addressable units are randomly distributed across the substrate).

An array may comprise any useful number of individually addressable units. For example, an array may have at least 5, at least 10, at least 100, at least 1,000, at least 10,000, at least 100,000, at least 1,000,000, at least 10,000,000, at least 100,000,000, at least 1,000,000,000 or greater number of individually addressable units. Alternatively, an array may have at most about 1,000,000,000, at most about 100,000,000, at most about 10,000,000, at most about 1,000,000, at most about 100,000, at most about 10,000, at most about 1,000, at most about 100, at most about 10, or at most about 5 individually addressable units. The array may have a range of number of individually addressable units, e.g., from about 1,000 to about 100,000, or from about 50,000 to about 1,000,000 individually addressable units.

Binding agents: In some embodiments, the methods, compositions, systems, and kits provided herein may include the use of a binding agent. A binding agent may be or comprise a protein or peptide (e.g., an antibody, antibody fragment, nanobody), a nucleic acid molecule (e.g., aptamer), a polymer, an inorganic compound, a small molecule, or derivatives (e.g., engineered variants) or combinations thereof. The binding agent can bind to a modified amino acid or portion thereof. The use of binding agents may be useful in the identification of individual amino acids (or modified amino acids) of a peptide or to modulate the translocation of a modified amino acid through a nanopore or nanogap. The binding agent may comprise a recognition site that specifically recognizes an amino acid, modified amino acid, or a derivatized (and optionally modified) amino acid. For example, the binding agent may be configured to recognize a moiety of a modified amino acid, such as a specific amino acid residue, the residue-linker complex, or derivatized amino acid (e.g., a thiocarbomyl-derivatized residue, a thiazolone-derivatized residue, a thiohydantoin-derivatized residue, etc.), or a portion of a modified amino acid. In some instances, the binding agent may be derived or engineered from a naturally-occurring enzyme, e.g., an aminopeptidase or tRNA synthetase.

In some instances, a binding agent may be provided as part of the intramolecular expansion process; for example, the binding agent may specifically recognize and bind to a modified amino acid (e.g., an AALC complex, an amino acid coupled to a polymerizable molecule) or a portion thereof. In some instances, the binding agent may recognize and bind to a moiety of the modified amino acid, e.g., the amino acid-linker conjugate or derivative thereof (e.g., an isothiocyanate-amino acid or a thiocarbamyl, thiazolone, or thiohydantoin derivative thereof). The binding agent may comprise a detectable moiety (e.g., fluorophore, barcode molecule, radioisotope, or other tag), which may facilitate detection and identification of individual amino acids. Alternatively, or in addition to, the binding agent may be recognized by an additional binding agent (e.g., a secondary antibody) comprising a detectable moiety; binding of the additional binding agent to the binding agent may be representative of the presence of the modified amino acid.

Figure 2:
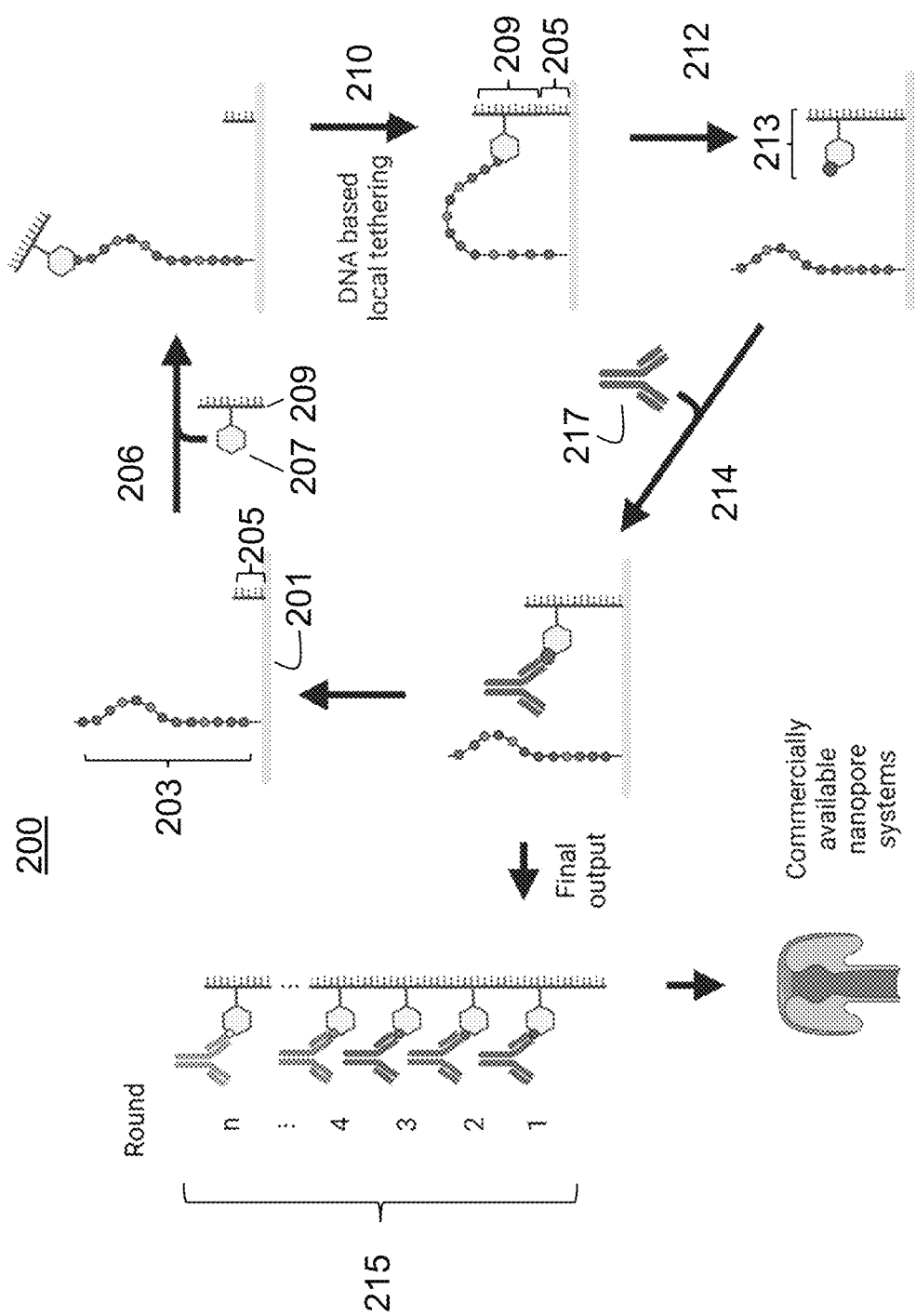
FIG. 2 schematically illustrates another example workflow for peptide sequencing disclosed herein.

FIG. 2 schematically illustrates another example workflow of intramolecular expansion of a peptide, including the use of binding agents. In workflow 200, a peptide 203 and a capture moiety 205 are provided, which optionally are coupled to a substrate 201. The capture moiety 205 may comprise a first nucleic acid molecule (e.g., DNA). In process 206, a linker 207 and polymerizable molecule 209, e.g., a second nucleic acid molecule are provided. In some instances, the linker 207 is pre-tethered to the polymerizable molecule 209; alternatively, the linker 207 and the polymerizable molecule 209 may be provided separately. In process 206, the linker 207 may couple to an amino acid (e.g., NTAA) of the peptide 203 to generate an amino acid-linker complex. In process 210, the amino acid-linker complex may couple to the capture moiety 205. Coupling of the amino acid-linker complex to the capture moiety 205 may be mediated by the polymerizable molecule 209. Optionally, the amino acid-linker complex and the capture moiety may be covalently linked together (e.g., the polymerizable molecule 209 may be covalently linked to the capture moiety 205), using chemical (e.g., click chemistry) or enzymatic (e.g., a ligase) approaches. Alternatively, or in addition to, the polymerizable molecule 209 may comprise a first sequence that is complementary and may hybridize to a second sequence of the capture moiety 205 (not shown), or the polymerizable molecule 209 may be linked to the capture moiety 205 via a splint or bridge molecule, which may comprise sequences that are complementary to the first sequence of the polymerizable molecule 209 and the second sequence of the capture moiety 205 (not shown). In process 212, the amino acid may be removed from the peptide 203 to generate an amino acid-linker-capture (AALC) complex 213, which comprises a modified amino acid (e.g., a NTAA that has been modified as a result of the cleavage from the peptide), the linker 207, the polymerizable molecule 209, and the capture moiety 205. In process 214, a binding agent 217 (e.g., an antibody, binding protein, etc.) may be contacted with the AALC complex 213. The binding agent may be configured to recognize all or a portion of the AALC complex 213. For example, the binding agent may recognize a residue of the modified amino acid, or the binding agent may recognize a residue and all or a portion of the linker 207. In one example, the linker may comprise a PITC moiety, and the binding agent may recognize the PITC-amino acid, or a derivative thereof, e.g., a phenylthiocarbamyl, a thiazolone, or a phenylthiohydantoin. In some instances, the binding agent 217 may comprise a detectable moiety (not shown) or may be contacted with an additional binding agent (e.g., a secondary antibody) which may optionally comprise a detectable moiety (not shown).

Processes 206, 210, 212, and 214 may be iterated and repeated any number of times ("rounds") using additional linkers 207 and polymerizable molecules 209 (optionally comprising cycle/round information), and tethering the additional polymerizable molecules together (e.g., tethering an additional polymerizable molecule to the polymerizable molecule of the AALC complex 113). Multiple rounds may continue until all or a subset of the amino acids in the peptide 203 are removed from the peptide and tethered together. For example, a modified amino acid derivative, such as a complex 215 comprising multiple modified amino acids may result from n rounds of the workflow 200 (e.g., iterations of processes 206, 210, 212, and optionally, 214).

Figure 3:
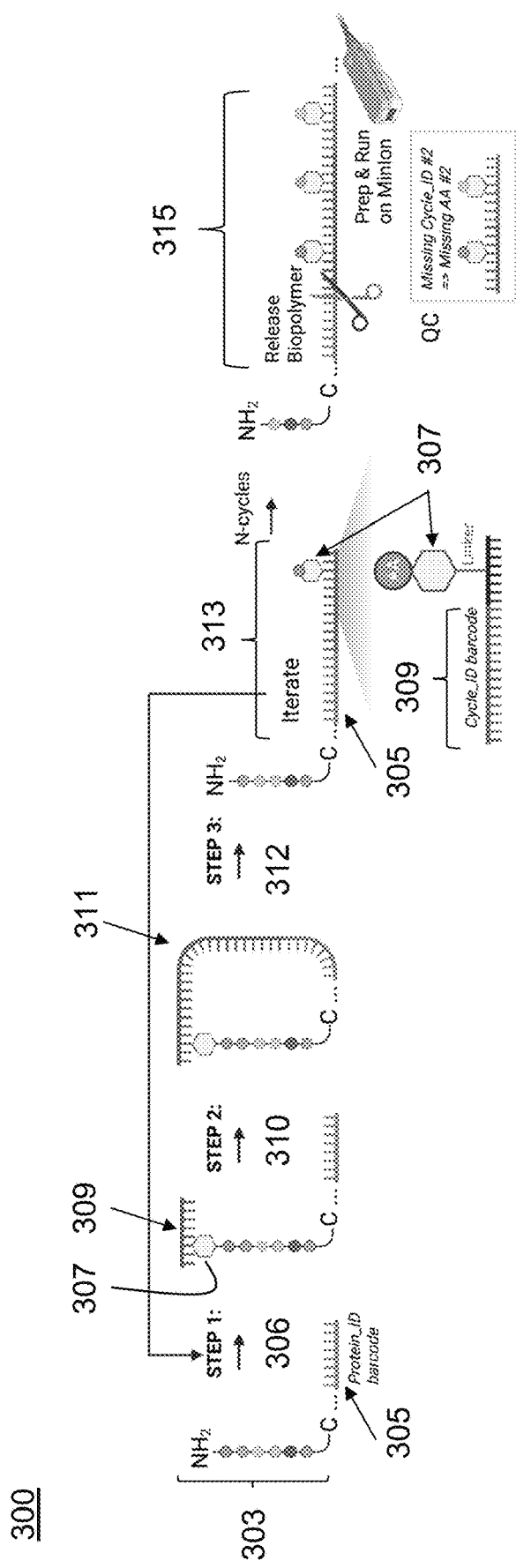
FIG. 3 schematically illustrates another example workflow for peptide sequencing disclosed herein.

Intramolecular expansion may be performed in solution or using substrate-free approaches. FIG. 3 schematically illustrates another example workflow of generating a modified amino acid using an intramolecular expansion process in solution, followed by nanopore sequencing. In such an example workflow 300, a peptide 303 and a capture moiety 305 are provided. The capture moiety 305 may comprise a first nucleic acid molecule (e.g., DNA molecule) and may comprise identifying information of the peptide 303, e.g., a peptide-identifying barcode sequence. The capture moiety 305 may additionally comprise a releasable or cleavable moiety. In process 306, a linker 307 and polymerizable molecule 309, e.g., a second nucleic acid molecule, are provided. In some instances, the linker 307 is pre-tethered to the polymerizable molecule 309; alternatively, the linker 307 and the polymerizable molecule 309 may be provided separately. The polymerizable molecule 309 may comprise identifying temporal information, e.g., the cycle or round in which it is provided. In process 306, the linker 307 may couple to an amino acid (e.g., NTAA) of the peptide 303 to generate an amino acid-linker complex. In process 310, the amino acid-linker complex may couple to the capture moiety 305. Coupling of the amino acid-linker complex to the capture moiety 305 may be mediated by the polymerizable molecule 309 and optionally an additional polymerizable molecule 311. Optionally, the amino acid-linker complex and the capture moiety may be covalently linked together (e.g., via ligation). Alternatively, or in addition to, the polymerizable molecule 309 may comprise a first sequence that is complementary and may hybridize to a second sequence of the capture moiety 305 (not shown), or the polymerizable molecule 309 may be linked to the capture moiety 305 via a splint or bridge molecule, which may comprise sequences that are complementary to the first sequence of the polymerizable molecule 309 and the second sequence of the capture moiety 305 (not shown). In process 312, the amino acid may be removed or cleaved from the peptide 312 to generate an amino acid-linker-capture (AALC) complex 313, which comprises a modified amino acid (e.g., a NTAA that has been modified as a result of the cleavage from the peptide), the linker 307, the polymerizable molecule 309, and the capture moiety 305. Processes 306, 310, and 312 may be iterated and repeated any number of times ("rounds") using additional linkers 307 and polymerizable molecules 309, and tethering the additional polymerizable molecules together (e.g., tethering an additional polymerizable molecule to the polymerizable molecule of the AALC complex 313). Multiple rounds may continue until all or a subset of the amino acids in the peptide 303 are removed from the peptide and tethered together. For example, a modified amino acid derivative, such as a complex 315 comprising a stacked AALC complex that comprises multiple modified amino acids, may result from n rounds of the workflow 300 (e.g., iterations of processes 306, 310, and 312). After any useful number of rounds, the completed, stacked AALC complex may be cleaved from the or at the capture moiety 305, e.g., using the cleavable moiety. The cleaved product may then be sequenced using a nanopore or nanogap approach.

In some instances, the polymerizable molecule 309 comprises temporal information on the cycle in which it is provided; as such, the temporal information may be used for conducting quality control. For example, if a missing cycle number is missing, then it can be inferred that an amino acid is missing or was not present in the peptide, that cleavage of the amino acid did not occur, or other error.

It will be appreciated that the order of the operations and processes provided herein are listed for example purposes only, and that any of the operations and processes may be performed at any convenient or useful step or time. For example, the polymerizable molecule may be provided pre-coupled to the linker (e.g., as shown in process 106 of FIG. 1, 206 of FIGS. 2, and 306 of FIG. 3), or the polymerizable molecule may be provided prior to or subsequent to provision of the linker. Similarly, the coupling of the polymerizable molecule to the capture moiety may occur prior to, during, or subsequently to the coupling of the linker to the amino acid. In another example, the removal (e.g., cleavage) of the amino acid from the peptide may occur prior to, during, or subsequently to the coupling of the polymerizable molecule to the capture moiety. In yet another example, in instances where a binding agent and intramolecular expansion are performed, the binding agent may be introduced prior to, during, or subsequent to the intramolecular process. For example, the operations of workflows 100, 200 and 300 may be performed and the stacked AALC complexes (115, 215, and 315) may be contacted with a plurality of binding agents that have specificity to individual or oligomers (e.g., dipeptides or tripeptides) of different modified amino acids (e.g., 10, 20, or greater different binding agents, each with specificity to a different amino acid or modified amino acid). The plurality of binding agents may comprise a detectable label which may be used for amino acid identification (e.g., using single-molecule imaging); alternatively or in addition to, the complex of AALC complexes and binding agents may be introduced into a nanopore or nanogap for sequencing.

Additional operations to the methods described herein are also contemplated. For example, referring to FIGS. 1-3, the AALC complex 113, 213, or 313 or a portion of the AALC complex may, in some instances, be cleaved or removed from the substrate or peptide (e.g., via cleavage, enzymatic digestion, chemical dissociation) prior to iteration of the workflow 100, 200, or 300. In such an example, the cleaved molecule (e.g., comprising the modified amino acid and optionally the polymerizable molecule) may be translocated through a nanopore for protein sequencing. In another example, additional cleaving or dissociation reactions may be performed to separate the amino acid from the polymerizable molecule. In such instances, the separated polymerizable molecule or the amino acid may be translocated through the nanopore. Additional useful operations, methods, systems, and compositions for processing or using peptides, linkers, polymerizable molecules, etc. can also be found in PCT/US2023/017954, which is incorporated by reference herein in its entirety.

Any of the operations described herein may occur under any useful physical conditions. For instance, one or more operations described herein may occur at an elevated or lowered temperature, either of which may aid in reaction speeds, reaction completion, translocation velocity or dwell time of a molecule through the nanopore or nanogap, etc. In some instances, the nanopore or nanogap sequencing system may be performed on ice or lowered temperature, which can beneficially increase the measured signal-to-noise ratio of the current signal, modulate the translocation velocity of the molecules through the nanopore or nanogap, or otherwise improve readout or detection.

Detection: Additional methods and devices for sequencing peptides and/or polymerizable molecules may be used alternatively or in addition to nanopore or nanogap sequencing. For example, the methods provided herein may utilize one or more imaging systems for identifying a molecule (e.g., a modified amino acid or a polymerizable molecule). Examples of optical imaging systems and methods include but are not limited to: epifluorescence microscopy, confocal microscopy, total internal reflection fluorescence (TIRF) microscopy, expansion microscopy, two-photon microscopy, integrated correlative microscopy, stimulated emission depletion (STED) microscopy, stochastic optical reconstruction microscopy (STORM), reversible saturable optically linear fluorescence transitions (RESOLFT), spatially modulated illumination, spectral precision distance microscopy (SPDM), photoactivated localization microscopy (PALM), fluorescence PALM (FPALM), structured illumination microscopy (SIM), saturated SIM (SSIM), among others.

In some instances, imaging may be used to identify a modified amino acid or polymerizable molecule. For example, referring to FIG. 2, a binding agent (e.g., antibody) may carry a fluorophore or other optically detectable tag, and the binding agent may selectively bind to a particular residue of a modified amino acid (e.g., in process 217). The fluorophore may identify the binding agent, such that presence of the fluorophore indicates the presence of the binding agent (and thus the amino acid residue to which the binding agent binds). Alternatively, a secondary binding agent (e.g., a secondary antibody) carrying a fluorophore or other detectable agent may bind to the binding agent (e.g., a primary antibody) to indicate the presence of the binding agent (and thus the amino acid residue to which the primary antibody binds). Similarly, with respect to the polymerizable molecule (e.g., a nucleic acid molecule), the sequence of the nucleic acid molecule may be determined using any suitable imaging technique, e.g., fluorescence in situ hybridization, or sequencing by synthesis.

Alternatively or in addition to, other proteomic tools may be used to identify the modified amino acids and polymerizable molecules. For example, a modified amino acid (e.g., an amino acid that has been contacted with a PITC linker coupled to a DNA molecule) may be analyzed using mass spectrometry, immunochemistry (e.g., via ELISA, fluorescence imaging), or other analytical technique. In some instances, further processing of the modified amino acid may be performed prior to analysis. For example, such further processing may include detachment of the modified amino acid from a substrate, enrichment or purification, or addition of tags or other moieties. In some instances, the modified amino acid may be subjected to a separation technique prior to analysis, e.g., chromatography (e.g., liquid chromatography, HPLC, nano-LC), electrophoretic separation (e.g., electrophoresis, isoelectric focusing, electroosmotic flow), filtration, evaporation, distillation, or other separation technique.

In another aspect of the present disclosure, disclosed herein is a method for analyzing an analyte, comprising: (a) providing a polymerizable molecule (e.g., a nucleic acid molecule) coupled to the analyte, (b) sequencing the polymerizable molecule (e.g., nucleic acid molecule) and (c) identifying the analyte, in which (b) and (c) are performed substantially simultaneously.

The analyte may comprise a non-nucleic acid biomolecule (e.g., a protein or peptide, a lipid, a carbohydrate, a combination thereof) or a component thereof. In some instances, the analyte is a peptide comprising at least two amino acids. In some instances, the analyte comprises a modified amino acid, as described elsewhere herein (e.g., a modified amino acid generated from a peptide via intramolecular expansion and the use of linkers). In some instances, the analyte comprises the modified amino acid, the linker, and the polymerizable molecule (e.g., nucleic acid molecule), as described elsewhere herein.

As described herein, the analysis method may comprise the use of nanopores or nanogaps for sequencing or identification. The nanopore or nanogap sequencing approach can be useful in generation of multiplexed data, such as (i) sequencing of a polymerizable molecule (e.g., sequencing a nucleic acid molecule to generate sequencing reads) and (ii) identification of the analyte (e.g., identification of an amino acid residue). Such generation of multiplexed data may occur substantially simultaneously, e.g., within about 5 minutes, about 1 minute, about 1 second, about 1 millisecond, about 1 microsecond, about 1 picosecond, or less. Alternatively, or in addition to, the sequencing and identification may not occur substantially simultaneously, but rather signal generation from the polymerizable molecule and the amino acid may occur substantially simultaneously. For example, the modified amino acids or derivatives thereof (e.g., AALC complex, stacked AALC complexes, or portions thereof) may be translocated through a nanopore. As the modified amino acids or derivatives thereof translocate through the nanopore, one or more signals (e.g., current signal) generated from both the polymerizable molecule and the amino acid may be generated and collected. Such one or more signals may then be deconvolved using computational approaches to determine the identity of the polymerizable molecules (e.g., nucleic acid sequences) and the amino acid types of the modified amino acids or derivatives thereof. Beneficially, the use of nanopore or nanogap sequencing for generation of multiplexed data may obviate the need for multiple analysis techniques or instruments.

Systems, Kits, Compositions: Also provided herein are systems, kits, and compositions for characterizing analytes (e.g., peptides). The systems, kits, and compositions provided herein may be useful in implementing any of the described methods or may be provided in complement to the described methods.

In one aspect, a kit of the present may comprise a substrate, a capture moiety, a linker, a polymerizable molecule, a peptide-conjugation reagent, an enzyme (e.g., a polymerizing or ligating enzyme, a cleaving enzyme, a restriction enzyme, a nicking enzyme, an exonuclease, a repair enzyme such as a uracil DNA glycosylase), a detection or labeling agent, or any combination thereof. The kits may comprise buffers, reagents, binding agents, catalysts, or other chemicals or biological molecules (e.g., enzymes) necessary for conducting a chemical or enzymatic reaction. The kits of the present disclosure may further comprise instructions for using the components of the kit or for implementing any of the methods and processes described herein. For example, the kit may comprise instructions for conjugating a peptide onto a substrate using a peptide-conjugation reaction. The kit may comprise instructions for conjugating a capture moiety to a substrate, or alternatively, the substrate may comprise the capture moieties coupled thereto. Similarly, the kit may comprise instructions for performing intramolecular expansion, as described herein, e.g., to generate a modified amino acid comprising a polymerizable molecule (e.g., DNA) coupled thereto, an amino acid-linker complex, an AALC complex, etc.

In another aspect, disclosed herein are compositions that may be used to characterize an analyte (e.g., peptide). A composition may comprise a linker covalently attached to a polymerizable molecule (e.g., a nucleic acid molecule), which may, for example, be useful in intramolecular expansion of a peptide for peptide sequencing. In an example, a composition may comprise (A) a linker comprising (i) a first moiety that can couple to an amino acid (e.g., a CTAA or NTAA of a peptide), (ii) a second moiety that can couple to a nucleic acid molecule (e.g., DNA), and, optionally, (iii) a releasable or cleavable moiety, which may be the same or different moiety as (ii), and also optionally, (iv) a spacer moiety, and (B) a nucleic acid molecule. In another example, the composition may comprise a linker that is covalently coupled to a nucleic acid molecule; such a linker may comprise a moiety that can couple to and optionally cleave an amino acid (e.g., a CTAA or NTAA of a peptide), and the covalently coupled nucleic acid molecule may be configured to tether to another nucleic acid molecule (e.g., a capture moiety), which may in some instances, be provided attached to a substrate.

Figure 4:
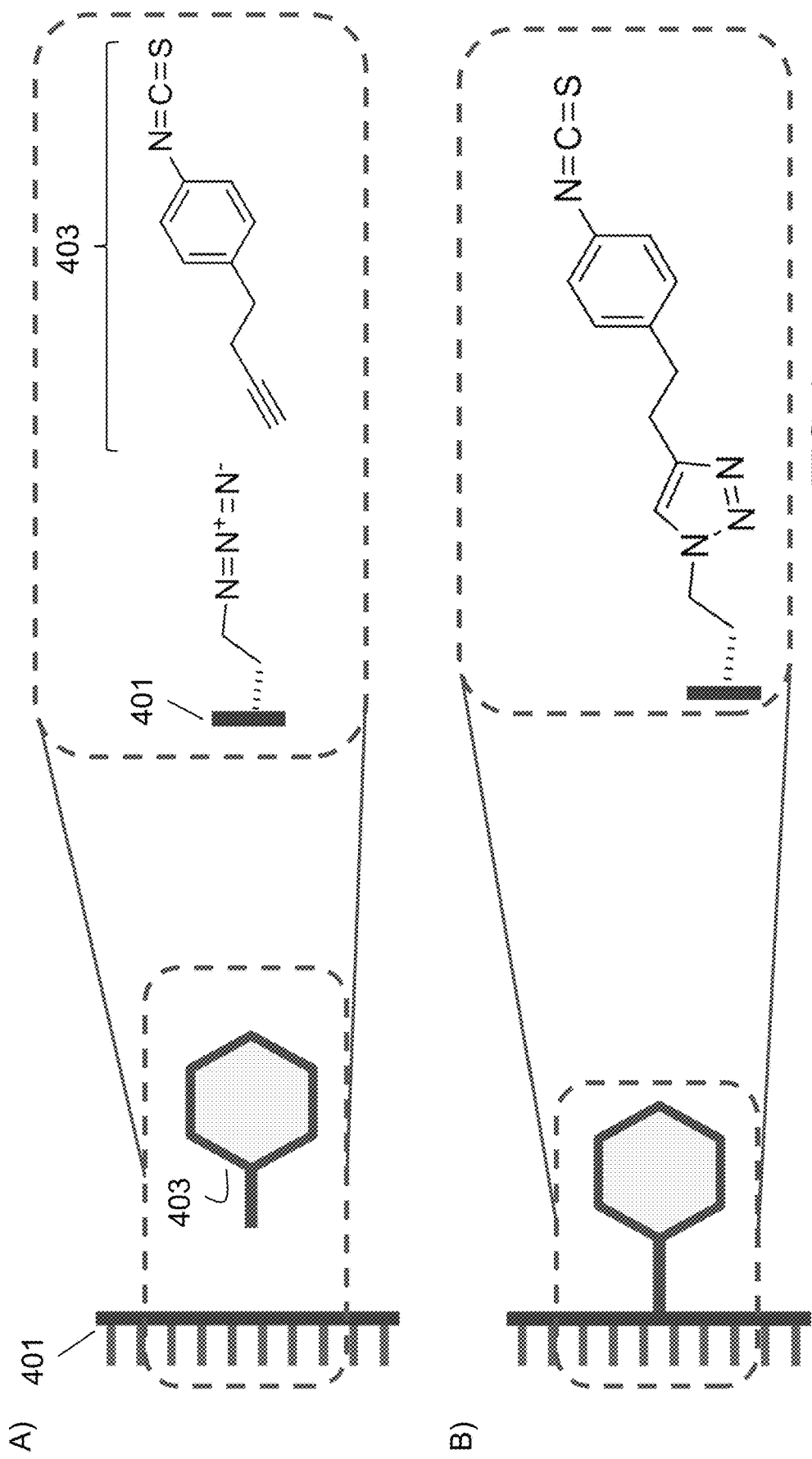
FIG. 4 schematically illustrates an example composition comprising a linker and a polymerizable molecule.

FIG. 4 schematically illustrates an example composition described herein. FIG. 4 Panel A shows a linker 403 that may be coupled to a polymerizable molecule 401 (e.g., a DNA molecule). The polymerizable molecule 401 may comprise a first reactive group such as an azide moiety (denoted as N=N$^+$=N$^-$), which may be attached to the polymerizable molecule 401 at any useful position e.g., for a DNA molecule, at a 5' end, a 3' end, or at an internal position of the DNA molecule. The linker 403 may comprise (i) an amino acid-reactive moiety, e.g., a thiocyanate (e.g., as shown N=C=S) or a PITC, and (ii) a second reactive group (e.g., an alkyne) that is capable of reacting with the first reactive group (e.g., azide) of the polymerizable molecule 401. FIG. 4 Panel B shows an example of a polymerizable molecule that is covalently coupled to a linker. The first reactive group (e.g., azide) of the polymerizable molecule may be reacted with the second reactive group (e.g., alkyne) of the linker, thereby generating a covalently-linked structure comprising the polymerizable molecule and the linker, which may be capable of reacting and tethering to an amino acid. As described herein, the amino-acid reactive group (e.g., ITC, PITC) may also be capable of cleaving the amino acid from a peptide. In some instances, the first reactive group is attached to the polymerizable molecule via an additional linker. For example, the additional linker may comprise nucleic acid linker that comprises a modified nucleobase or sugar backbone such as a nucleoside, nucleoside monophosphate, nucleoside diphosphate, or nucleoside triphosphate that can be incorporated into a nucleic acid molecule. The additional linker may also comprise the first reactive group, e.g., click chemistry moiety. In some examples, the additional linker comprises an ethynyl deoxyuridine or octadiynyl deoxyuridine.

Systems, compositions, kits: Also provided herein are systems, compositions, and kits for processing peptides or for generating or processing modified amino acids. A system of the present disclosure may comprise a sequencing instrument that is configured to receive a modified amino acid or derivative thereof, as described herein, and to provide sequencing reads of the modified amino acid or derivative thereof. Alternatively, or in addition to, a system of the present disclosure may be configured to process, prepare, or sequence a modified amino acid. The system may be configured to provide the peptide, the capture moiety, and a linker comprising a polymerizable molecule; couple the linker to an amino acid of the peptide; cleave the amino acid from the peptide; and optionally, iterate one or more operations or processes. Accordingly, systems of the present disclosure may comprise any useful apparatuses or tools, including but not limited to mixers, liquid handlers, vortexes, centrifuges, heating or cooling elements, mechanical stages, microfluidic chambers or devices and fluidic controls.

A system of the present disclosure may comprise a nanopore or nanochannel sequencing system that is configured to sequence or analyze a modified amino acid. The modified amino acid may comprise or be coupled to a polymerizable molecule, as is described elsewhere herein. As such, the system may be configured to output multiplexed data regarding the modified amino acid (e.g., which of the 20 proteinogenic amino acid residues a modified amino acid is or is derived from), and the polymerizable molecule (e.g., a nucleic acid sequence). A system of the present disclosure may comprise a substrate, a capture moiety, a linker, a polymerizable molecule, a peptide-conjugation reagent, an enzyme (e.g., a polymerizing or ligating enzyme, a cleaving enzyme, a restriction enzyme, a nicking enzyme, an exonuclease, a repair enzyme such as a uracil DNA glycosylase), a detection or labeling agent, buffers, reagents, binding agents, catalysts, or other chemicals or biological molecules (e.g., enzymes) necessary for conducting a chemical or enzymatic reaction, or any combination thereof. The system may further comprise one or more detection (e.g., imaging or mass spectrometry) systems, separation systems (e.g., HPLC), or other analytical instrument.

A composition of the present disclosure may comprise any useful items or reagents for processing or sequencing a peptide or for generating the modified amino acids or derivatives thereof. A composition may comprise a capture moiety configured to couple to a polymerizable molecule. The composition may comprise a linker (e.g., to couple to an amino acid), which linker may comprise a polymerizable molecule, a cleaving agent, a ligating agent (e.g., ligase), a capture moiety, reagents for conducting a reaction, or a combination thereof. In some instances, a composition comprises a linker comprising (e.g., covalently attached thereto) a nucleic acid barcode molecule, wherein the linker comprises an amino acid-reactive group. The nucleic acid barcode molecule may comprise any useful barcode sequences, e.g., spatial, temporal, peptide-identifying, partition-identifying, sample-identifying sequences, a UMI, or other functional sequence.

Kits of the present disclosure may comprise any useful reagents for processing, analyzing, or sequencing a peptide. A kit may comprise a reagent for providing the peptide and a capture moiety, a reagent for coupling the peptide and capture moiety to a substrate, a reagent for cleaving an amino acid, a reagent for coupling the peptide to a linker comprising an amino acid reactive group and either an additional reactive group or a polymerizable molecule, a reagent for coupling the capture moiety to the polymerizable molecule, a reagent for providing a binding agent, a cleaving reagent, a stabilizing reagent, a wash buffer, or a combination thereof. The kit may further comprise reagents for removing or decoupling an amino acid from the peptide, or from removing or decoupling an AALC complex from a substrate or from the capture moiety. In some instances, the kit may further comprise reagents for removing or decoupling an AALC complex or stacked AALC complex from a substrate, or the kit may comprise reagents for conducting a nucleic acid extension reaction. The kit may include any relevant reagents, e.g., buffers, detergents, chelating agents, cofactors, enzymes, ribozymes or DNAzymes, acids, bases, salts, metal ions, primers, nucleic acid molecules, nucleotides, proteins, polynucleotides, binding agents (e.g., antibodies, aptamers, nanobodies, antibody fragments), lipids, carbohydrates, ribozymes, riboswitches, probes, fluorophores, oxidizing agents, reducing agents, nuclease or protease inhibitors, dyes, organic molecules, inorganic molecules, emulsifiers, surfactants, stabilizers, polymers, water, small molecules, therapeutics, radioactive materials, preservatives, or other useful reagent. The kits of the present disclosure may also provide instructions for the use of the contents of the kit.

Substrate Conjugation

The present disclosure provides methods for coupling molecules (e.g., polymeric analytes, e.g., biomolecules such as nucleic acid molecules, peptides, lipids, carbohydrates, etc.) to a substrate. The substrate may be functionalized to allow for covalent or noncovalent coupling of the molecules to a substrate. The substrate may comprise any useful functional moiety, e.g., a reactive moiety, that can couple or conjugate to a molecule or another reactive moiety. In a non-limiting example, a reactive moiety may comprise a click chemistry moiety, such as an azide, alkyne, nitrone, alkene (e.g., a strained alkene), tetrazine, methyltetrazine, triazole, tetrazole, phosphite, phosphine, etc. A click chemistry moiety may be reactive in copper-catalyzed Huisgen cycloaddition or the 1,3-dipolar cycloaddition between an azide and a terminal alkyne, a Diels-Alder reaction (e.g., a cycloaddition between a diene and a dienophile), or a nucleophilic substitution reaction in which one of the reactive species is an epoxy or aziridine. A molecule that is to be coupled to a substrate may comprise a complementary click chemistry moiety to that of the substrate; for example, the substrate may comprise an alkyne moiety and the molecule to be coupled may comprise an azide moiety, which can react with the alkyne moiety of the substrate to generate a covalent linkage. In one such example, the substate may comprise dibenzocyclooctyne (DBCO) moieties to which azide-comprising molecules (e.g., azide-DNA, azide-polymers, azide-peptides) can react and conjugate.

Alternatively, or in addition to, the reactive moiety may comprise a photoreactive moiety that may be activated when exposed to a photostimulus (e.g., light such as UV or visible light). Examples of photoreactive moieties include aryl (phenyl) azides (e.g., phenyl azide, ortho-hydroxyphenyl azide, meta-hydroxyphenyl azide, tetrafluorophenyl azide, ortho-nitrophenyl azide, meta-nitrophenyl azide), diazirines, azido-methyl-coumarins, benzophenones, anthraquinones, diazo compounds, diazirines, psoralen, 3-cyanovinylcarbazole phosphoramidite (CNVK), and analogs or derivatives thereof.

The reactive moiety may comprise a carboxyl-reactive crosslinker group, such as diazo compounds such as diazomethane and diazoacetyl, carbonyldiimidazole, carbodiimides (e.g., 1-ethyl-3-(3-dimethylaminopropyl)carbodiimide hydrochloride (EDC)), dicyclohexylcarbodiimide (DCC)), or an amine-reactive group (e.g., N-hydroxysulfosuccinimide (NHS), Sulfo-NHS, or NHS-esters). The reactive group may comprise a crosslinking agent, which may comprise an NHS group, an EDC group, a maleimide (e.g., for coupling with a Michael acceptor), a thiol, a cystamine, an aldehyde, a succinimidyl group, an epoxide, an acrylate. Examples of crosslinking agents include, for example, NHS (N-hydroxysuccinimide); sulfo-NHS (N-hydroxysulfosuccinimide); EDC (1-Ethyl-3-[3-dimethylaminopropyl]); carbodiimide hydrochloride; SMCC (succinimidyl 4-(N-maleimidomethyl)cyclohexane-1-carboxylate); sulfo-SMCC; DSS (disuccinimidyl suberate); DSG (disuccinimidyl glutarate); DFDNB (1,5-difluoro-2,4-dinitrobenzene); BS3 (bis(sulfosuccinimidyl)suberate); TSAT (tris-(succinimidyl)aminotriacetate); BS(PEG)5 (PEGylated bis(sulfosuccinimidyl)suberate); BS(PEG)9 (PEGylated bis(sulfosuccinimidyl) suberate); DSP(dithiobis(succinimidyl propionate)); DTSSP (3,3'-dithiobis(sulfosuccinimidyl propionate)); DST(disuccinimidyl tartrate); BSOCOES (bis(2-(succinimidooxycarbonyloxy)ethyl)sulfone); EGS (ethylene glycol bis(succinimidyl succinate)); DMA (dimethyl adipimidate); DMP (dimethyl pimelimidate); DMS (dimethyl suberimidate); DTBP (Wang and Richard's Reagent); BM(PEG)2 (1,8-bismaleimido-diethyleneglycol); BM(PEG)3 (1,11-bismaleimido-triethyleneglycol); BMB (1,4-bismaleimidobutane); DTME (dithiobismaleimidoethane); BMH (bismaleimidohexane); BMOE (bismaleimidoethane); TMEA (tris(2-maleimidoethyl)amine); SPDP (succinimidyl 3-(2-pyridyldithio)propionate); SMCC (Succinimidyl trans-4-(maleimidylmethyl)cyclohexane-1-Carboxylate); SIA (succinimidyl iodoacetate); SBAP (succinimidyl 3-(bromoacetamido)propionate); STAB (succinimidyl (4-iodoacetyl) aminobenzoate); Sulfo-SIAB (sulfosuccinimidyl (4-iodoacetyl) aminobenzoate); AMAS (N-α-maleimidoacetoxysuccinimide ester); BMPS (N—O-maleimidopropyl-oxysuccinimide ester); GMBS (N-γ-maleimidobutyryl-oxysuccinimide ester); Sulfo-GMBS (N-γ-maleimidobutyryl-oxysulfosuccinimide ester); MBS (m-maleimidobenzoyl-N-hydroxysuccinimide ester); Sulfo-MBS (m-maleimidobenzoyl-N-hydroxysulfosuccinimide ester); SMCC (succinimidyl 4-(N-maleimidomethyl)cyclohexane-1-carboxylate); Sulfo-SMCC (sulfosuccinimidyl 4-(N-maleimidomethyl)cyclohexane-1-carboxylate); EMCS (N-E-malemidocaproyl-oxysuccinimide ester); Sulfo-EMCS (N-s-maleimidocaproyl-oxysulfosuccinimide ester); SMPB (succinimidyl 4-(p-maleimidophenyl)butyrate); Sulfo-SMPB (sulfosuccinimidyl 4-(N-maleimidophenyl)butyrate); SMPH (Succinimidyl 6-((beta-maleimidopropionamido)hexanoate)); LC-SMCC (succinimidyl 4-(N-maleimidomethyl) cyclohexane-1-carboxy-(6-amidocaproate)); Sulfo-KMUS (N-κ-maleimidoundecanoyl-oxysulfosuccinimide ester); SPDP (succinimidyl 3-(2-pyridyldithio)propionate); LC-SPDP (succinimidyl 6-(3(2-pyridyldithio)propionamido) hexanoate); LC-SPDP (succinimidyl 6-(3(2-pyridyldithio)propionamido)hexanoate); Sulfo-LC-SPDP (sulfosuccinimidyl 6-(3'-(2-pyridyldithio)propionamido) hexanoate); SMPT (4-succinimidyloxycarbonyl-alpha-methyl-u(2-pyridyldithio)toluene); PEG4-SPDP (PEGylated, long-chain SPDP crosslinker); PEG12-SPDP (PEGylated, long-chain SPDP crosslinker); SM(PEG)2 (PEGylated SMCC crosslinker); SM(PEG)4 (PEGylated SMCC crosslinker); SM(PEG)6 (PEGylated, long-chain SMCC crosslinker); SM(PEG)8 (PEGylated, long-chain SMCC crosslinker); SM(PEG)12 (PEGylated, long-chain SMCC crosslinker); SM(PEG)24 (PEGylated, long-chain SMCC crosslinker); BMPH (N—O-maleimidopropionic acid hydrazide); EMCH (N-ε-maleimidocaproic acid hydrazide); MPBH (4-(4-N-maleimidophenyl)butyric acid hydrazide); KMUH (N-κ-maleimidoundecanoic acid hydrazide); PDPH (3-(2-pyridyldithio)propionyl hydrazide); ATFB-SE (4-Azido-2,3,5,6-Tetrafluorobenzoic Acid, Succinimidyl Ester); ANB-NOS (N-5-azido-2-nitrobenzoyloxysuccinimide); SDA (NHS-Diazirine) (succinimidyl 4,4'-azipentanoate); LC-SDA (NHS-LC-Diazirine) (succinimidyl 6-(4,4'-azipentanamido)hexanoate); SDAD (NHS-SS-Diazirine) (succinimidyl 2-((4,4'-azipentanamido)ethyl)-1,3'-dithiopropionate); Sulfo-SDA (Sulfo-NHS-Diazirine) (sulfosuccinimidyl 4,4'-azipentanoate); Sulfo-LC-SDA (Sulfo-NHS-LC-Diazirine) (sulfosuccinimidyl 6-(4,4'-azipentanamido) hexanoate); Sulfo-SDAD (Sulfo-NHS-SS-Diazirine) (sulfosuccinimidyl 2-((4,4'-azipentanamido)ethyl)-1,3'-dithiopropionate); SPB (succinimidyl-[4-(psoralen–8-yloxy)]-butyrate); Sulfo-SANPAH (sulfosuccinimidyl 6-(4'-azido-2'-nitrophenylamino)hexanoate); DCC (dicyclohexylcarbodiimide); EDC (1-ethyl-3-(3-dimethylaminopropyl)carbodiimide hydrochloride); gluteraldehyde; formaldehyde; and combinations or derivatives thereof.

Molecules may also be attached to substrates using linkers. The linkers can have any useful number of functional groups or reactive groups and may be uni-functional (having one functional group), bi-functional, tri-functional, quadri-functional, or comprise a greater number of functional groups. In some instances, a molecule (e.g., nucleic acid molecule, peptide, or polymer) may be attached to a substrate using a heterobifunctional linker. The heterobifunctional linker may comprise any useful functional group, as described herein. Non-limiting examples of heterobifunctional linkers include: p-Azidobenzoyl hydrazide (ABH), N-5-Azido-2-nitrobenzoyloxysuccinimide (ANB-NOS), N-[4-(p-Azidosalicylamido)butyl]-3'-(2'-pyridyldithio) propionamide (APDP), p-Azidophenyl Glyoxal monohydrate (APG), Bis[B-(4-azidosalicylamido)ethyl]disulfide (BASED), Bis[2-(Succinimidooxycarbonyloxy)ethyl] Sulfone (BSOCOES), BMPS, 1,4-Di [3'-(2'-pyridyldithio) propionamido] Butane (DPDPB), Dithiobis(succinimidyl Propionate) (DSP), Disuccinimidyl Suberate (DSS), Discuccinimidyl Tartrate (DST), 3,3'-Dithiobis(sulfosuccinimidyl Propionate (DTSSP), EDC, Ethylene Glycol bis (succinimidyl succinate) (EGS), N-(E-maleimidocaproic acid hydrazide (EMCH), N-(E-maleimidocaproyloxy)-succinimide ester (EMCS), N-Maleimidobutyryloxysuccinimide ester (GMBS), Hydroxylamine-HCl, MAL-PEG-SCM, m-Maleimidobenzoyl-N-hydroxysuccinimide Ester (MBS), N-Hydroxysuccinimidyl-4-azidosalicylic acid (NHS-ASA), PDPH, N-Succinimidyl bromoacetate (SBA), SIA, Sulfo-SIA, Succinimidyl-4-(N-maleimidomethyl)cyclohexane-1-carboxylate (SMCC), Succinimidyl 4-(p-maleimidophenyl) Butyrate (SMPB), Succinimidyl-6-[β-maleimidopropionamido]hexanoate (SMPH), N-Succinimidyl 3-[2-pyridyldithio]-propionate (SPDP), Sulfo-LC-SPDP, N-(p-Maleimidophenyl isocyanate (PMPI), N-Succinimidyl(4-iodoacetyl) Aminobenzoate (SIAB), Sulfo-MBS, Sulfo-SANPAH, Sulfo-SMCC, Sulfo-DST, Sulfo-EMCS, Sulfo-GMBS, N-Hydroxysulfosuccinimidyl-4-azidobenzoate (Sulfo-HSAB), Sulfosuccinimidyl (4-azidophenyl)-1,3 dithio propionate (Sulfo-SADP), Sulfosuccinimidyl 2-(m-azido-o-nitrobenzamido)-ethyl-1,3'-dithio propionate (Sulfo-SAND), Sulfosuccinimidyl-2-(p-azidosalicylamido)ethyl-1,3-dithio-propionate (Sulfo SASD), Sulfo-SIAB, Sulfo-SMCC, Sulfo-SMPB, and the like.

Additional examples of conjugation reactions that may be used to attach molecules to substrates include an Ullmann reaction, Heck reaction, Negishi reaction, Stille reaction, Suzuki reaction, Buchwald-Hartwig coupling, Castro-Stevens coupling, Glaser coupling, Kumada coupling, Larock indole synthesis, Miyaura borylation, Sonagashira cross-coupling, a Grubbs reaction.

More than one type of molecule may be coupled to the substrate. For example, a substrate may be coupled to nucleic acid molecules and peptides. Alternatively, a substrate may be coupled to only one type of molecule (e.g., only nucleic acid molecules, only peptides, only lipids, only carbohydrates, etc.). A substrate may be coupled to any useful combination of molecules, linkers, reactive moieties or functional groups, which may be coupled at any useful density, as described elsewhere herein. For example, a multifunctional linker may be used to attach both a nucleic acid barcode molecule and a peptide to the substrate. Alternatively, the substrate may comprise a plurality of bifunctional linkers that can conjugate to different molecules. In another example, a substrate may comprise a linker and reactive sites; the linker may be used to attach one type of molecule (e.g., peptides or nucleic acid molecules), whereas the reactive sites may be used to attach another type of molecule (e.g., nucleic acid molecules or peptides).

Linkers can comprise other functional portions, such as spacers (e.g., polymer chains, e.g., PEG, alkyl chains, etc.), cleavage sites (e.g., disulfide bridges that are cleavable upon application of a chemical stimulus, photocleavable or thermocleavable moieties, etc.), enzyme recognition sites, etc.

The proximity of a molecule coupled to a substrate to its nearest neighbor (e.g., another molecule) may be controlled using a variety of approaches, e.g., self-assembling monolayers, patterning approaches, linking moieties, etc. In some instances, it may be advantageous to have two molecules in close proximity (e.g., two polymerizable molecules, such as a peptide and a nucleic acid molecule, or two nucleic acid molecules). For instance, with respect to the sequencing approaches described herein, capture moieties may be used to couple a monomer of a polymeric analyte, and subsequent to monomer cleavage, an additional polymerizable molecule or plurality of polymerizable molecules may be required to be in proximity to the capture moiety to allow for transfer of information encoded by polymerizable molecules of binding agents. The proximity of the molecules (e.g., capture moiety and polymerizable molecules) may be mediated using tethering molecules, such as nucleic acid molecule "staples" or multi-functional linkers.

Nucleic acid molecules may be coupled to a substrate by direct coupling. In such instances, the substrate or the nucleic acid molecules may comprise functional moieties that can interact. For example, the substrate and nucleic acid molecules may comprise a complementary click chemistry pair, e.g., alkyne and azide. In one such example, a substrate may comprise alkyne moieties (e.g., DBCO), which can be reacted with azide-functionalized nucleic acid molecules. The nucleic acid molecules may be reacted with the alkyne moieties in a click chemistry reaction to covalently link the substrate to the nucleic acid molecules. In another example, the substrate may comprise avidin or streptavidin moieties, to which biotinylated nucleic acid molecules may interact and bind non-covalently. Alternatively, or in addition to, the substrate may comprise a nucleic acid molecule to which additional nucleic acid molecules (e.g., nucleic acid analytes, nucleic acid linkers) are conjugated using hybridization, ligation, click chemistry, crosslinking (e.g., photocrosslinking such as CNVK).

Alternatively, or in addition to, the nucleic acid molecules may be coupled to a substrate using a linker, e.g., as described elsewhere herein. The linker may comprise at least two functional groups (e.g., a heterobifunctional linker) that can couple to both the substrate and the nucleic acid molecules. In an example, the substrate may comprise an amine group, and alkyne-functionalized DNA primers (e.g., DBCO-DNA primers) may be attached using a linker such as azidoacetic acid NHS ester. In another example, amine-functionalized substrates may be coupled to azide-functionalized DNA primers using a DBCO-NHS ester or DBCO-PEG-NHS ester linker. As described elsewhere herein, the linkers may comprise additional functional moieties (e.g., cleavage sites, spacers such as polymer or alkyl chains).

Similarly, peptides may be coupled to a substrate by direct coupling or by using a linker. A peptide may be coupled to a substrate at a terminus of the peptide (e.g., C terminus or N terminus), at an internal residue or amino acid of the peptide, or at multiple locations along the peptide. In examples of direct coupling, a peptide may be functionalized with a moiety that can interact with a moiety of the substrate (e.g., click chemistry pair, avidin-biotin). For example, the substrate and peptides may comprise a complementary click chemistry pair, e.g., alkyne and azide, or binding partners such as avidin and biotin. In one example of a click chemistry pair, a substrate may comprise alkyne moieties (e.g., DBCO), which can be reacted with azide-functionalized peptides. The peptides may be reacted with the alkyne moieties in a click chemistry reaction to covalently link the substrate to the peptides. In another example, the substrate may comprise avidin or streptavidin moieties, to which biotinylated peptides may interact and bind non-covalently.

Alternatively, or in addition to, the peptides may be coupled to a substrate using a linker, e.g., as described elsewhere herein. The linker may comprise at least two functional groups (e.g., a heterobifunctional linker) that can couple to both the substrate and the nucleic acid molecules. In an example, the substrate may comprise an amine group, and alkyne-functionalized peptides may be attached using a linker such as azidoacetic acid NHS ester. In another example, amine-functionalized substrates may be coupled to azide-functionalized peptides using a DBCO-NHS ester or DBCO-PEG-NHS ester linker. In yet another example, substrates comprising an amine group may be coupled to an azide-functionalized peptide using EDC and Sulfo-NHS.

A peptide may be functionalized with a functional moiety to enable attachment or coupling of the peptide to the substrate. The functional moiety may comprise a silane, e.g., aminosilane (e.g., APTES), amino-PEG-silane, click chemistry moiety or other linking moiety and can be attached to the peptide at a peptide terminus (N-terminus or C-terminus), at an internal amino acid, or at multiple locations (e.g., multiple internal amino acids, one or both termini, etc.). Chemical approaches to functionalize peptides can include C-terminal-specific conjugation (e.g., via C-terminal decarboxylative alkylation) using photoredox catalysis, e.g., as described by Bloom et al, *Nature Chemistry* 10, 205-211. 2018. and Zhang et al, *ACS Chem. Biol.* 2021, 16, 11, 2595-2603, each of which is incorporated by reference herein in its entirety, or amide coupling to an amine-functionalized surface. N-terminal attachment may comprise amide coupling of the N-terminus amine group to a carboxylic group functionalized surface or using 2-pyridinecarboxaldehyde variants. Alternatively, or in addition to, functionalization of terminal ends of peptides may be achieved enzymatically or using enzyme analogs such as ribozymes or DNAzymes. In an example of enzymatic functionalization and attachment, carboxypeptidases or amidases are used for C-terminal functionalization (e.g., as described in Xu et al, *ACS Chem Biol.* 2011 Oct. 21; 6(10): 1015-1020; Zhu et al, *Chinese Chemical Letters.* 2018, Vol 29 Issue 7, Pages 1116-1118; and Zhu et al, *ACS Catal.* 2022, 12, 13, 8019-8026, each of which is incorporated by reference herein in its entirety), which can allow for the addition of a click chemistry moiety to the peptide. The click chemistry-functionalized peptides may then be directly attached to the substrate via another clickable group (e.g., BCN-azide or DBCO-azide coupling), or, in other instances, may be reacted with another linker or polymerizable molecule (e.g., a bait nucleic acid molecule with a clickable group) that can then link to the substrate directly or indirectly (e.g., using a capture nucleic acid molecule and hybridizing the bait nucleic acid molecule). Additional examples of enzymes that can be used for functionalization or attachment include Sortase A, subtiligase, Butelase I, or trypsiligase. In some examples, ubiquitin ligase can be used to attach ubiquitin proteins with linker moieties to substrates. These linker moieties can then be used to chemically attach proteins to ubiquitin-coupled substrates. In some examples, glycosylating enzymes may be used to conjugate functionalized sugar groups (e.g., click chemistry functionalized sugars, polymer-conjugated sugars, biotinylated sugars) to amino acid residues, which can allow for attachment to a substrate (e.g., via click chemistry, polymer crosslinking or nucleic acid hybridization, avidin-biotin interactions), etc. Internal amino acid residues or post-translationally modified residues may be coupled to substrates using, for example, thiol labeling, amide coupling using EDC/NHS chemistry or DMT-MM to glutamate or aspartate residues, esterifying glutamate or aspartate residues, alkylation or disulfide bridge labeling of cysteines, or amide coupling to lysine residues.

A peptide may be treated prior to, during, or subsequent to coupling of the peptide to a substrate. In some instances, a peptide is conjugated with a tag that enables attachment to the substrate, e.g., using His tags, SNAP-tags, CLIP-tags, SpyCatcher, SpyTag, nucleic acid tags (e.g., bait oligos which can attach to capture oligos of the substrate).

In some examples, it may be advantageous to block or protect primary amines or carboxyl groups and optionally, de-block or de-protect the N-terminus primary amine or C-terminus carboxy group in order to facilitate attachment of the N-terminus or C-terminus to a substrate. In an example, single-point (e.g., C-terminal) selective attachment of peptides can be achieved by reacting the peptide with a linker comprising an amine-reactive group (e.g., isothiocyanates such as PITC) and a reactive group (e.g., click chemistry group). The linker can be, for example, PITC-conjugated click chemistry moieties such as PITC-azide, PITC-alkyne, optionally with spacer moieties in between, e.g., PITC-alkyl-azide, PITC-PEG-azide, PITC-alkyl-alkyne, PITC-PEG-azide). The linker reacts with and "blocks" the primary amines (e.g., modifies lysines), including the N-terminus. Subsequent cleavage of the N-terminal amino acid (e.g., using an Edman reagent, such as acid), can be performed, and one of the remaining modified lysines may be attached to a substrate (e.g., using the click chemistry moiety coupled to the amine-reactive group). Optionally, the peptide may be treated with a protease, e.g., LysC, which cleaves peptides such that a remaining peptide has a C-terminal lysine and such that the remaining peptide comprises a primary amine only at the C-terminal lysine residue and the N-terminus; such a cleavage may be performed prior to reacting the amine-reactive group, e.g., as shown by Xie et al. *Langmuir* 2022, 38, 30, 9119-9128, which is incorporated by reference herein in its entirety.

Similarly, carboxylic groups can be reacted in a way to enable C-terminal or internal residue attachment. In an example of C-terminal conjugation, carboxyl groups may be labeled with a C-terminal sequencing reagent, such as isothiocyanate, when treated with an activating reagent (e.g., acetic anhydride) to generate a peptide-thiohydantoin (at the C-terminus) and "blocked" carboxyl groups on the aspartic acid and glutamic acid residues. The thiohydantoin may then be reacted to couple to a substrate. Alternatively, cleavage of the C-terminal amino acid via a single round of C-terminal sequencing degradation, or via a protease, exposes only a single reactive carboxylic group at the C-terminal amino acid. The single reactive C-terminal carboxylic group can then be used as a reactive moiety for a single attachment site.

In another approach, a peptide or protein can be attached via the N-terminus using the specific reactivities of the N-terminus amine group. Amine-based reactions, such as amide coupling, can be carried out at low pH where only the N-terminal amine group is active. In addition, 2-pyridinecarboxyaldehyde and variants can be used to react to the N-terminal amine group.

In some instances, a peptide may be conjugated to a substrate using a polymerization reaction, e.g., a free radical polymerization, such as using PEGylated peptides, methacrylamide-modified peptides, Michael-type addition of maleimide-terminated oligo-NIPAAM-conjugated peptides; photocrosslinking of azophenyl-conjugated peptides, or other polymerization reactions with monomer-conjugated peptides, e.g., as described by Krishna et al. Biopolymers. 2010; 94(1): 32-48, which is incorporated by reference herein in its entirety.

Multiple types of molecules may be attached to a substrate. The substrate may comprise, coupled thereto, any combination of molecules, including but not limited to peptides, proteins (e.g., enzymes, ribozymes, DNAzymes, antibodies, nanobodies, antibody fragments), nucleic acid molecules, lipids, carbohydrates or sugars, metabolites, small molecules, polymers, metals, viral particles, biotin, avidin, streptavidin, neutravidin, etc. The multiple types of molecules may be attached simultaneously to the substrate or in a sequential manner. For example, a substrate may be treated to conjugate nucleic acid molecules and subsequently treated to conjugate peptides, or alternatively, the substrate may be treated to conjugate peptides prior to the nucleic acid molecules. Any number of conjugation or attachment chemistries may be used. For example, in instances where multiple types of molecules are attached to the substrate, any number of conjugation chemistries may be used for each type of molecule.

A substrate, or portion thereof, may be subjected to conditions sufficient to passivate the substrate or portion thereof. Passivation of a substrate may be useful for a variety of purposes, such as preventing nonspecific binding of binding agents, altering the surface density of a molecule (e.g., increasing the density of nucleic acid molecules or peptides), blocking reactive sites (e.g., blocking available click chemistry moieties subsequent to conjugation of the molecules on the substrate), etc. Passivation may be achieved using chemical approaches, e.g., deposition of blocking agents such as proteins (e.g., albumin), Tween-20, polymers, metals or metal oxides, or biochemical approaches, e.g., using metal microbes. Substrates comprising reactive moieties may also be passivated following molecule conjugation (e.g., coupling of nucleic acid molecules, peptides, etc.) by reacting any unreacted sites with an appropriate molecule. For example, a substrate comprising click chemistry moieties, e.g., DBCO beads, may be coupled to molecules of interest (e.g., polymerizable molecules, such as nucleic acid molecules, peptides) at a useful density using click chemistry (e.g., azide-nucleic acid molecules, azide-peptides). Unreacted sites may be passivated by providing and reacting complementary click-chemistry molecules, e.g., azide-polymers (e.g., PEG-azide), which may reduce downstream nonspecific interactions.

Substrate passivation may occur at any useful time or step. For instance, passivation to block unreacted DBCO sites may be performed prior to, during, or subsequent to conjugation of analytes or other molecules of interest (e.g., peptides and nucleic acid molecules). The passivation may be controlled by stoichiometry or densities of the passivating agent relative to the molecules of interest, or by physical approaches, e.g., photopatterning, self-assembling monolayers, etc.

Sample Processing

The present disclosure also provides for methods of processing samples. One or more methods for processing samples may comprise preparation of biological samples for analysis, which, in some instances, includes partitioning of cells for conducting single-cell analysis. A method for processing a biological sample may comprise extraction or isolation of one or more peptides or proteins from the biological sample for further processing and analysis, as is described elsewhere herein.

Preparation of Cell Suspensions for Single-Cell Analysis: The methods described herein may involve preparation of single cell suspensions from a biological sample. Single cell suspensions may be prepared from biological samples by dissociating cells and optionally, culturing them in a liquid medium. In some instances, biological samples comprise a liquid sample. For example, a biological sample may comprise a bacterial liquid culture, a mammalian liquid culture, a blood, plasma, or serum sample. Processing of such liquid samples may include centrifugation (e.g., to isolate cells), resuspension of cells in a suitable medium, such as Dulbecco's Phosphate Buffered Saline (DPBS), and optional culturing of the isolated cells.

A biological sample may comprise cultured cells, e.g., cell cultured in suspension, or cells adhered to a solid surface, such as petri dishes or tissue culture dishes. Cultured adherent cells samples may be treated to generate a cell suspension, e.g., via a protease such as trypsin, to detach the cells from the surface. A biological sample may comprise a tissue or biopsy sample. A tissue or biopsy sample may be processed mechanically or enzymatically to generate a cell suspension. Such processing may include sonication (mechanical treatment) or enzymatic treatment, such as the use of pronase, collagenase, hyaluronidase, metalloproteinases, trypsin, or other enzymes that digest extracellular matrix components. The dissociated cells can then be stored in a suitable buffer, such as DPBS.

Cell Sorting: A biological sample or a cell suspension may be subjected to sorting to isolate a cell of interest. Sorting may be performed to select or isolate a cell based on a quality or characteristic of the cell, e.g., expression of a protein target, size, deformability, fluorescence or other optical property, or other physical property of the cell. Sorting may be accomplished using any number of approaches, e.g., using immunosorting (e.g., fluorescence activated cell sorting (FACS) or magnetic activated cell sorting (MACS)), electrophoretic approaches, chromatography, microfluidic approaches (e.g., using inertial focusing, cell traps, electrophoresis, isoelectric focusing), acoustic sorting, optical sorting (e.g., optoelectronic tweezers), mechanical cell picking (e.g., using manual or robotic pipettes) or passive approaches (e.g., gravitational settling).

Partitioning: Cells of a biological sample or cell suspension may be partitioned into individual partitions such that at least a subset of the individual partitions comprises a single cell. The individual partitions may comprise a barcode molecule (e.g., fluorophore or set of fluorophores, nucleic acid barcode molecules, etc.). Barcode molecules may be unique to the partition, such that each individual partition comprises a different barcode sequence than other partitions. The barcode molecules may be loaded into the individual partitions at any useful ratio of barcode molecules to sample species (e.g., cells, proteins, nucleic acid molecules). The barcode molecules may be loaded into partitions such that about 0.0001, 0.001, 0.1, 1, 2, 3, 4, 5, 6, 7, 8, 9, 10, 20, 50, 100, 500, 1000, 5000, 10000, or 200000 barcodes are loaded per sample species. In some cases, the barcodes are loaded into partitions such that more than about 0.0001, 0.001, 0.1, 1, 2, 3, 4, 5, 6, 7, 8, 9, 10, 20, 50, 100, 500, 1000, 5000, 10000, or 200000 barcodes are loaded per sample species. In some cases, the barcodes are loaded in the partitions so that less than about 0.0001, 0.001, 0.1, 1, 2, 3, 4, 5, 6, 7, 8, 9, 10, 20, 50, 100, 500, 1000, 5000, 10000, or 200000 barcodes are loaded per sample species.

A partition may assume any useful geometry such as a droplet, a microwell, a solid substrate, a gel (e.g., a cell encapsulated in a gel bead), a bead, a flask, a tube, a spot, a capsule, a channel, a chamber, or other compartment or vessel. A partition may be part of an array of partitions, e.g., a droplet in a microfluidic device, a microwell of a microwell plate, a spot on a multi-spot array, etc.

Lysis, Permeabilization, and Analyte Extraction: Single cells (e.g., in partitions) may be processed to obtain one or more analytes contained therein. A method for processing a single cell may comprise lysing the cell to release the contents into the individual compartment or partition. Lysis may be performed using a detergent (e.g., Triton-X 100, sodium dodecyl sulfate, sodium deoxycholate, CHAPS), RIPA buffer, a change in temperature (e.g., elevated or lower temperature, freezing, freeze-thawing), enzymes, ribozymes, DNAzymes, mechanical lysis (e.g., sonication, application of mechanical force), electrical lysis, or a combination thereof. Lysis may be performed in the presence of protease inhibitors to prevent degradation or digestion of the proteins from the cell. The contents may optionally be further processed, e.g., subjected to purification or extraction, denaturation of proteins or peptides, enzyme or chemical digestion, etc. In some instances, the contents may be subjected to enzymatic digestion to remove nucleic acid molecules, e.g. using nucleases such as DNAse or RNAse. Alternatively or in addition to, a cell may be fixed (e.g., using a fixative) and/or permeabilized. Examples of fixatives include aldehydes (e.g., glutaraldehyde, formaldehyde, paraformaldehyde), alcohols (e.g., methanol, ethanol), acetone, acids (e.g., acetic acid, Davidson's AFA), oxidizing agents (e.g., osmium tetroxide, potassium dichromate, chromic acid, permanganate salts), Zenker's fixative, picrates, Hepes-glutamic acid buffer-mediated organic solvent protection effect (HOPE), or Karnovsky fixative. Cell permeabilization may be achieved mechanically (e.g., using sonication, electroporation, shearing) or chemically (e.g., using an organic solvent such as methanol or acetone or detergents such as saponin, Tween-20, Triton X-100).

Protein Processing: The biological sample (or single cell suspensions or partitioned cells) may be further processed to enable proteomic analysis. For example, de-aggregation of proteins in the sample may be performed, e.g., using chemical or mechanical approaches. Chemical de-aggregation methods can include but are not limited to sodium dodecyl (SDS), Triton-X 100, 3-((3-cholamidopropyl) dimethylamminio)-1-proppanesulfonate (CHAPS), ethylene carbonate, or formamide. Mechanical de-aggregation methods can include but are not limited to sonication or high temperature treatment. The biological sample (or single cell suspensions or partitioned cells) may be subjected to conditions sufficient to denature one or more proteins. Denaturation may be achieved using heat, chemicals (e.g., SDS, urea, guanidine, formamide, metal organic compounds), reducing agents (e.g., dithiothreitol (DTT), beta mercaptoethanol, TCEP), urea, chaotropes, enzymes (e.g., ClpX, ClpS, unfoldases), ribozymes or DNAzymes. Similarly, the peptides or proteins may be subjected to conditions to solubilize the peptides or proteins in a solution, e.g., using detergents, organic solvents, spermidine, or tagging the peptides or proteins with polyionic tags (e.g., DNA, PEG, or other polymers). Alternatively, or in addition, the peptides or proteins may be enriched or purified; in an example, the peptides or proteins of interest may be precipitated using trichloroacetic acid, chloroform, TRIzol, or other chemical reagent. Other biological or chemical agents may be included during the protein processing, e.g., lysozymes, papain, cruzain, trypsin, protease inhibitors, nucleases or nuclease-containing proteins (e.g., DNAse, RNAse, DNA glycosylases, restriction endonucleases, transposases, micrococcal nucleases, Cas proteins). In some instances, minimal protein processing is performed, e.g., to maintain native states or conformations of the proteins.

Peptides or proteins may be fragmented prior to analysis. Fragmenting proteins may be useful in reducing the size of the proteins and allow for efficient processing of peptides, as is described elsewhere herein. Fragmentation may be performed using proteases, e.g., trypsin, chymotrypsin, pepsin, Lys-C, Glu-C, Proteinase K, furin, thrombin, endopeptidase, papain, subtilisin, elastase, enterokinase, genenanse, endoproteinase, metalloproteases, or with chemical treatment, e.g., cyanogen bromide, hydrazine, hydroxylamine, formic acid, BNPS-skatole, iodosobenzoic acid, 2-nitro-5-thiocyanobenzoic acid, etc. Alternatively or in addition to, fragmentation may be performed using mechanical methods, such as sonication, vortexing, mechanical stirring, using temperature changes (e.g., freeze/thaw, heating), or other fragmentation approach.

Enrichment of proteins or peptides in a biological sample may be performed, e.g., for separating proteins and peptides from cellular debris or other types of analytes (e.g., nucleic acids, lipids, carbohydrates, metabolites). Such enrichment may include, for example, the use of affinity columns (e.g., ion exchange), size exclusion columns, affinity precipitation (e.g., immunoprecipitation), chemical precipitation (e.g., using trichloroacetic acid, chloroform, TRIzol), chromatography (e.g., HPLC), or electrophoresis. In instances where cells are partitioned prior to enrichment, the enrichment may be performed using microbeads, affinity microcolumns, affinity beads, etc. In some instances, fractionation may be performed on the proteins or peptides, which may be used to separate the proteins by size, hydrophobicity, charge, affinity, size, mass, density, etc.

Peptides may be barcoded, in bulk or in partitions. Peptides may be barcoded with any useful type of barcode molecule, e.g., spectral or fluorescent barcodes, mass tags, nucleic acid barcode molecules, etc. The barcode molecules may allow for identification of an originating peptide, a partition, a sample, a cell, or cell compartment. For example, a cell sample may be partitioned such that a partition comprises at most one cell; the partition may comprise a unique barcode molecule (e.g., nucleic acid barcode molecule) that identifies the partition and thus the cell. Subsequent labeling of the peptides within the partition (e.g., by permeabilizing or lysing the cell) with the barcode molecules may be useful in identifying the peptides as arising or originating from the same cell or partition. In other examples, a substrate may comprise nucleic acid molecules comprising a unique barcode sequence that differs from barcode sequences of other substrates. As such, the barcode sequence may be used to identify the substrate. In some instances, barcoded substrates may be partitioned with cell samples, such that at least a subset of the partitions comprise a single cell and a single barcoded substrate. As such, the peptides arising from the single cell and transferred to the barcoded substrate may all be identifiable as originating from the single cell. Barcode molecules may comprise additional useful functional sequences, e.g., UMIs, primer sites, restriction sites, cleavage sites, transposition sites, sequencing sites, read sites, etc.

Attachment of barcode molecules to peptides may be achieved using any suitable chemistry. For example, C-terminal conjugation of nucleic acid barcode molecules may be achieved by amide coupling of amine-conjugated DNA barcode molecules to peptides or by thiol alkylation, e.g., reacting a thiolated peptide with an alkylated (e.g., iodoacetamide) DNA barcode molecule. N-terminal conjugation can be achieved, for instance, using 2-pyridinecarboxyaldehyde labeling of a DNA barcode and reacting with the N-terminus of a peptide. Internal residues, e.g., glutamate, can also be labeled with amine-conjugated DNA barcode molecules or carboxylated DNA barcodes (e.g., to react with primary amines in lysine).

Individual peptides may be barcoded at multiple locations for a given peptide. A peptide may be labeled at multiple sites with the same or different barcode sequences. For example, a peptide may be partitioned into a partition comprising a plurality of identical barcode molecules that comprise a barcode sequence that is unique to the partition. The peptide may be labeled at a single or multiple sites with the unique partition barcode sequence, optionally each comprising a unique molecular identifier (UMI), such that subsequent downstream analysis (e.g., sequencing) may be attributable to the same peptide using the barcode sequence. In some instances, a terminus of the peptide (e.g., N-terminus or C-terminus) or an internal amino acid may be labeled with a barcode. In some instances, the peptide may be fragmented prior to analysis or sequencing; accordingly, upstream attachment of multiple identical barcode molecules to the same peptide may allow for attribution of the sequence analysis back to a single peptide. Barcoding of peptides may occur prior to, during, or subsequent to fragmentation. Peptides may be labeled with barcodes (e.g., nucleic acid barcode molecules) using any suitable chemistry, e.g., as described above, or using bifunctional or trifunctional linkers comprising multiple linking moieties, e.g., as described elsewhere herein, such as click chemistry moieties, NHS-esters, EDC, etc. For example, C-terminal attachment may comprise amide coupling to C-terminus carboxylic group or photoredox tagging of C-terminus carboxylic group (e.g., to add an electrophile tag). N-terminal attachment may comprise amide coupling to N-terminus amine group, where specific attachment can occur at low pH, or using 2-pyridinecarboxaldehyde variants for specific attachment to N-terminus. Internal attachment may comprise, for example, amide coupling using EDC/NHS chemistry or DMT-MM to Glutamate or Aspartate; alkylation or disulfide bridge labeling of cysteines; or amide coupling to lysine residues.

In some examples, a peptide may be labeled with different barcode molecules, which can be indexed by proximity to one another, e.g., using primers that can anneal to adjacent barcode molecules. In one such approach, after a protein has been labeled with a plurality of barcodes with different barcode sequences, proximity-based polymerase extension may be used to copy and associate the sequence of adjacent barcodes. For example, each barcode molecule may comprise a primer binding site, to which a dual-primer linker sequence comprising two sequences is annealed. The dual primer linker sequence can bind to the primer binding sites of two adjacent barcodes. An extension reaction, e.g., using a polymerase, may extend and copy the barcode sequences of the adjacent barcodes. Subsequently, the dual primer linker sequence, which now has copies of the two adjacent barcodes, may be removed and sequenced. From the sequencing reads, an adjacency matrix of barcode sequences may be generated (e.g., to correspond barcode sequences on a single dual primer linker as spatially adjacent). Accordingly, each of the barcode sequences may be associated with a nearby adjacent barcode sequences, and as such, peptide portions may be aligned or attributed as being adjacent. Such an approach may be useful in instances where the peptide is fragmented, such that individual fragments of a peptide may be corresponded with the nearest neighbor using the barcode sequences.

In another example, a peptide may be barcoded at multiple locations for a given peptide using bridge amplification. In such an approach, a peptide or protein may be labeled at multiple sites with a nucleic acid primer. A nucleic acid barcode molecule may be provided, which can anneal to the nucleic acid primer (not shown) or be ligated to the nucleic acid primer. Subsequent rounds of bridge amplification may be performed in order to copy the nucleic acid barcode molecule to the other primers located at other sites of the given peptide. In some examples, a peptide may be tagged with multiple copies of the nucleic acid primer, and barcode sequences may be provided sparsely, such that only one nucleic acid primer per peptide is extended by polymerase extension. Subsequent rounds of bridge amplification can result in a peptide having the same barcode sequence at each nucleic acid primer. Subsequent fragmenting of peptides may be performed, such that peptide fragments comprise on average, a single barcode. Accordingly, in some cases, the output such an amplification approach may be peptides with individual barcodes generated from fragmenting multi-labeled proteins where peptides from the same protein have the same barcodes.

A sample of cells may be partitioned into individual partitions or compartments (e.g., droplets, microwells) such that at least a subset of the partitions comprise a single cell. The partitions may then be treated with a lysing agent to lyse the cells and release the proteins from the cells into the partition. The proteins may then be labeled with a partition-specific barcode (e.g., using a barcode bead), such that all peptides or proteins arising from a single compartment comprises the same barcode. In some examples, the barcodes comprise nucleic acid barcode molecules, and the barcode sequence can be used in downstream processing, e.g., via sequencing, to identify the partition or cell from which a peptide originated. The nucleic acid barcode molecule may comprise any additional useful sequences, e.g., UMIs, primer sequences, etc.

Bulk Processing: A biological sample may be processed in bulk. For example, a biological sample may be processed to obtain a suspension of cells, which may be directly lysed in the suspension, without partitioning of cells in individual compartments. Cells may be lysed in bulk using any useful approach, e.g., as described above and optionally subjected to further processing, e.g., homogenization, protease inhibition, denaturation, protein processing (e.g., chemical treatment, fragmentation), or a combination thereof. A biological sample may be subjected to pre-processing prior to cell lysis or protein extraction. Such pre-processing may include removal of debris, purification, filtration, concentration, or sorting.

Spatial barcoding: A biological sample may comprise a tissue sample comprising multiple cells. Tissue samples may be processed using an approach to retain spatial information (e.g., to identify peptides from individual cells), e.g., using spatial barcodes. For instance, a 2-D or 3-D tissue sample may be provided, and individual cells or locations within a tissue sample may be contacted with a plurality of spatial barcodes (e.g., nucleic acid barcode molecules) comprising different barcode sequences. The different barcode sequences may be attributed to a particular location in the 2-D or 3-D tissue sample, which may correspond with a location of a cell. For example, spatial barcodes may be provided using deterministic methods such as two-photon patterning, or stochastic methods such as PCR, to assign different segments of the 2-D or 3-D tissue sample with unique spatial barcodes. Accordingly, peptides that are labeled with spatial barcodes may be attributed back to a single location within a tissue sample, or back to a single cell.

In another example of a workflow of spatial barcoding of a tissue sample, the tissue sample comprising multiple cells (illustrated as a 2×2 array of cells) may be provided. The tissue sample may be subjected to lysis or fixation and permeabilization to provide access to the proteins contained within the multiple cells. Spatial barcodes, e.g., nucleic acid barcode molecules, may be provided. The spatial barcodes may comprise coordinate or location information. In an example, each cell may be contacted with a different spatial barcode, or portions of cells may be contacted with different spatial barcodes, which may optionally be pre-indexed (e.g., using imaging, or deterministic spatial barcoding approaches). Further processing of the peptides may be performed, as described elsewhere herein. As the peptides are labeled with the spatial barcodes, each peptide having a spatial barcode may be attributed back to its originating coordinate or location, which can help identify the originating cell from which a peptide arises.

In an example, a spatial barcode array may be provided on a substrate (e.g., a glass microscope slide, a hydrogel mesh). In some instances, the spatial barcodes may be directly conjugated to the substrate, or they may be provided on barcoded beads. In an example, a plurality of beads each comprising different barcode sequences may be arranged in an array on a substrate. Each bead may comprise a spatial barcode comprising a spatial barcode sequence, and optionally, a unique molecular identifier (UMI). A tissue sample (e.g., a fixed tissue sample) may be placed adjacent to (e.g., overlayed onto) the spatial barcode array. The tissue sample may then be subjected to conditions sufficient to transfer the peptides or proteins to the spatial barcode array. For example, the peptides or proteins may be transferred via passive transport, e.g., diffusion or Brownian motion, or via active transport, e.g., electrophoresis, pressure-driven flow, etc. The peptides or proteins may be attached to the spatial barcodes, e.g., using a linker (e.g., comprising amine-reactive groups, or click chemistry groups such as azide, alkyne, or other functional moieties such as aldehyde groups or NHS or carboxylic groups), conjugation chemistry, or an anchoring agent. Examples of anchoring agents include fixatives, such as formaldehyde, paraformaldehyde, glutaraldehyde, or monomers for incorporation into a hydrogel, e.g., Acryloyl-X, acrylamide, N-(3-Aminopropyl)methacrylamide, or N-(3-Aminoethyl)methacrylamide, or benzophenone. Anchoring agents may also comprise multi-functional linkers, e.g., Acryloyl-X, Biotin-NHS, Biotin-PEG-Amine, DBCO-NHS, DBCO-amine. For bead arrays, the plurality of beads may be collected from the sample for further processing.

Computer Systems

Figure 5:
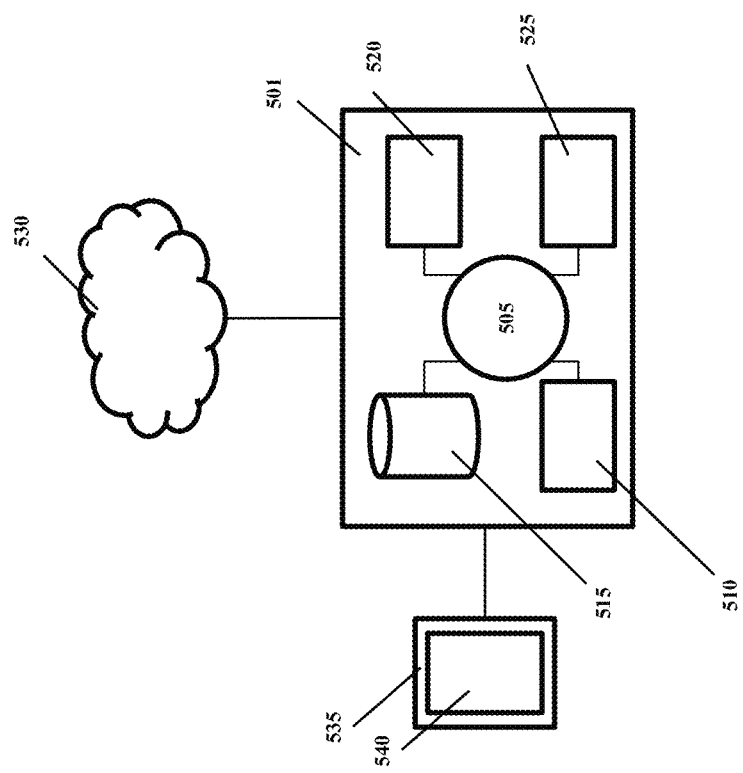
FIG. 5 shows a computer system that is programmed or otherwise configured to implement methods provided herein.

The present disclosure provides computer systems that are programmed to implement methods of the disclosure. FIG. 5 shows a computer system 501 that is programmed or otherwise configured to receive sequencing data and to output information on an identity of a polymerizable molecule or amino acid residues of modified amino acids. The computer system 501 can regulate various aspects of generating sequencing reads of the present disclosure, such as, for example, receiving one or more sets of sequencing data, using an algorithm to process the sequencing data, and outputting one or more sequencing results. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung@ Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine-readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, sequencing data results, the identity of the modified amino acids, the identity of the polymerizable molecules, or the nucleic acid sequence of a nucleic acid molecule. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, process the sequencing data (e.g., nanopore or nanogap ion current signals), to generate one or more sequencing outputs (e.g., identification of an amino acid or a monomer of a polymerizable molecule, e.g., a nucleic acid sequence of a nucleic acid molecule).

EXAMPLES

Example 1—Preparation of a Linker for Coupling a Polymerizable Molecule to an Amino Acid As described herein, a linker may comprise two functional components. The first functional component may be a moiety capable of reacting to amino acids. This moiety can be, for example, an isothiocyanate (e.g., PITC), dinitrofluorobenzene, dansyl chloride, or other amino acid-reactive groups. The second functional component may, in some instances, comprise a reactive group capable of coupling to a polymerizable molecule, which can be nucleic acid molecule (e.g., DNA, RNA, LNA, PNA), a peptide, or a synthetic organic compound. In the case of a DNA based polymerizable group, the DNA can comprise sequences for primers, sites for enzymatic ligation and chemical conjugation, barcode sequences, or a combination thereof. In some instances, the linker may be pre-functionalized to comprise the polymerizable molecule (e.g., as shown in FIG. 4 Panel B), as follows:

Method 1: Preparing a Linker-DNA Sequence Conjugate

A DNA sequence ranging from 15-150 bp in length is synthesized with either an internal Azide modification (e.g., Azide-dT modification, Integrated DNA Technologies) or an external Azide modification on the 5' or 3' ends. A linker comprising (i) a PITC moiety (amino acid-reactive group) and (ii) an alkyne moiety may be conjugated to the DNA sequence via Copper-Catalyzed Click Chemistry as follows: 100 µM linker and 10 µM of the DNA sequence are prepared in a reaction buffer consisting of 200 µM Tris((1-benzyl-1H-1,2,3-triazol-4-yl)methyl)amine (TBTA), 500 µM TCEP, and 200 µM CuSO4 in 1× PBS, pH 7.86. The reaction is incubated for 2 hours at room temperature. The linker-DNA sequence conjugate is then purified from the reaction using reverse-phase High Pressure Liquid Chromatography (HPLC). Method 2: Preparing a linker-peptide conjugate A peptide sequence (ranging from 10-50aa in length) may be synthesized with an internal cysteine residue. The peptide may be alkylated with iodoacetamide azide as follows: the peptide is reduced by preparing it at 1 mg/ml in a solution with 1% SDS and 100 mM ammonium bicarbonate (pH 8.0). To this solution, Tris(2-carboxyethyl) phosphine hydrochloride (TCEP-HCl) is added at a final concentration of 10 mM and incubated for 1 hour at 55 degrees C. Subsequently, iodoacetamide azide is added to a final concentration of 10 mM and incubated for 1 hour at room temperature. The alkylated peptide is then purified by buffer exchanging twice using a buffer exchange column. The alkylated peptide is then reacted with a linker comprising (i) a PITC moiety (amino-acid reactive group) and (ii) an alkyne moiety via Copper-Catalyzed Click chemistry. 100 µM of the linker and 10 µM of the alkylated peptide sequence are prepared in a reaction buffer consisting of 200 µM Tris((1-benzyl-1H-1,2,3-triazol-4-yl)methyl)amine (TBTA), 500 µM TCEP, and 200 µM CuSO4 in 1× PBS, pH 7.86. The reaction is incubated for 2 hours at room temperature. The Linker (linker-peptide sequence conjugate) is then purified from the reaction using reverse-phase High Pressure Liquid Chromatography (HPLC).

Figure 6A:
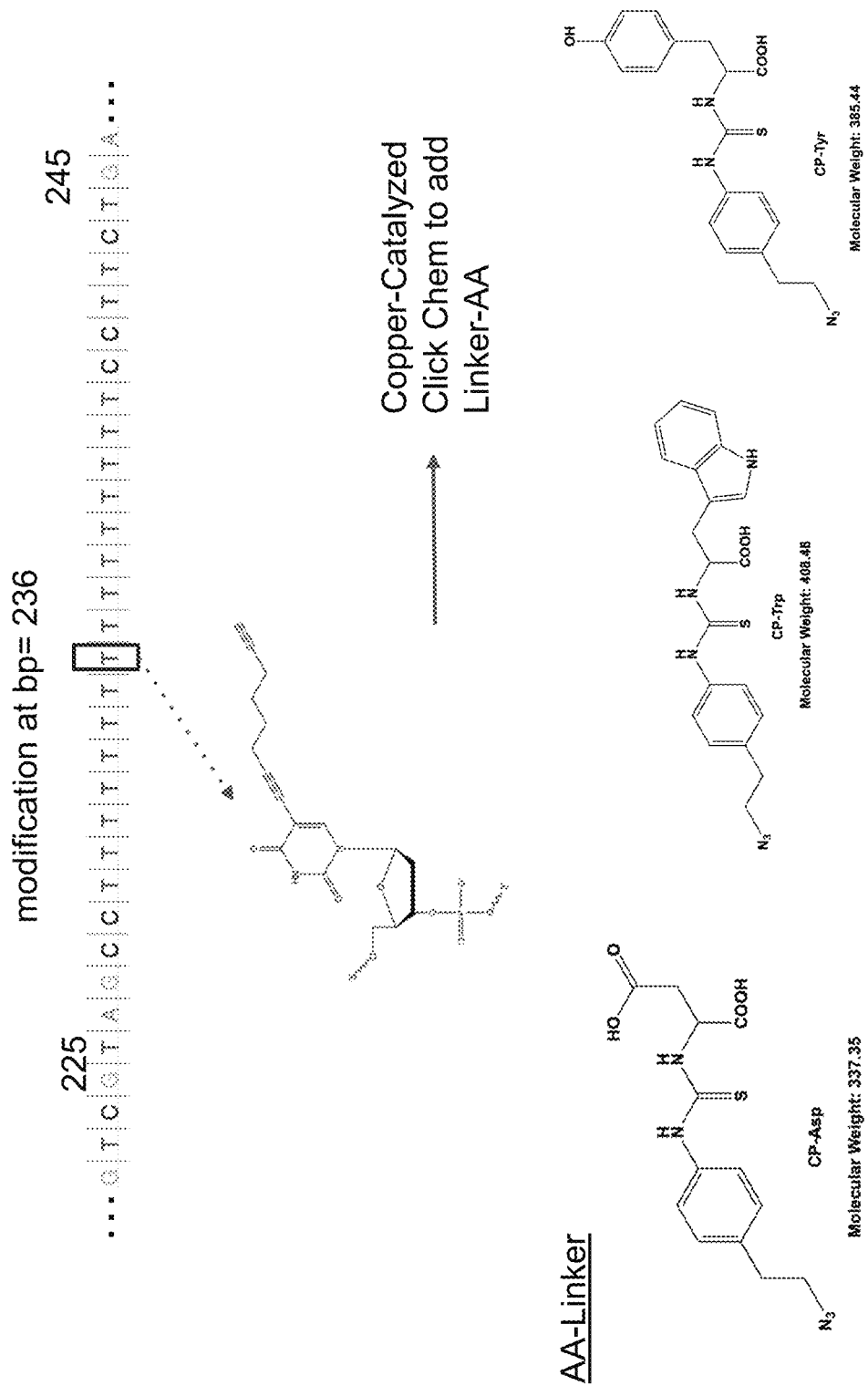
FIG. 6A shows a schematic of an example modified amino acid or derivative thereof comprising a polymerizable molecule and amino acid-linker complexes for three different amino acid types (Asp, Trp, and Tyr). Figure discloses SEQ ID NO: 2.

Example 2—Nanopore Detection of Amino Acids Conjugated to Polymerizable Molecules To determine whether nanopore detection of a modified amino acid or derivative thereof, e.g., an AALC complex or stacked AALC complex, or portion thereof, is possible, an amino acid-linker-polymerizable molecule complex is generated and translocated through a nanopore sequencing system. The amino acid-linker-polymerizable molecule complex is generated by coupling a polymerizable molecule to an amino acid-linker complex. The polymerizable molecule comprises an alkyne-linked DNA molecule. More specifically, the polymerizable molecule comprises an alkyne linker to a T236 position within a 16 nt poly-dT (SEQ ID NO: 1) DNA oligo scaffold located in the middle of one strand of a 450 nt dsDNA backbone, as schematically illustrated in FIG. 6A. The amino acid-linker complex is generated using a bifunctional linker, 1-(2-azidoethyl)-4- isothiocyanatobenzene, which comprises (1) a PITC moiety (amino acid reactive group) and (2) an azide moiety that is capable of reacting with the alkyne of the polymerizable molecule. The bifunctional linker is reacted with three different amino acids: Asp, Trp, and Tyr via the PITC moiety, thereby generating an amino acid-linker complex, also shown in the bottom panel of FIG. 6A. The amino acid-linker complexes are then reacted with the alkyne-linked DNA molecule, thereby generating an amino acid-linker-polymerizable molecule conjugate.

Figure 6B:
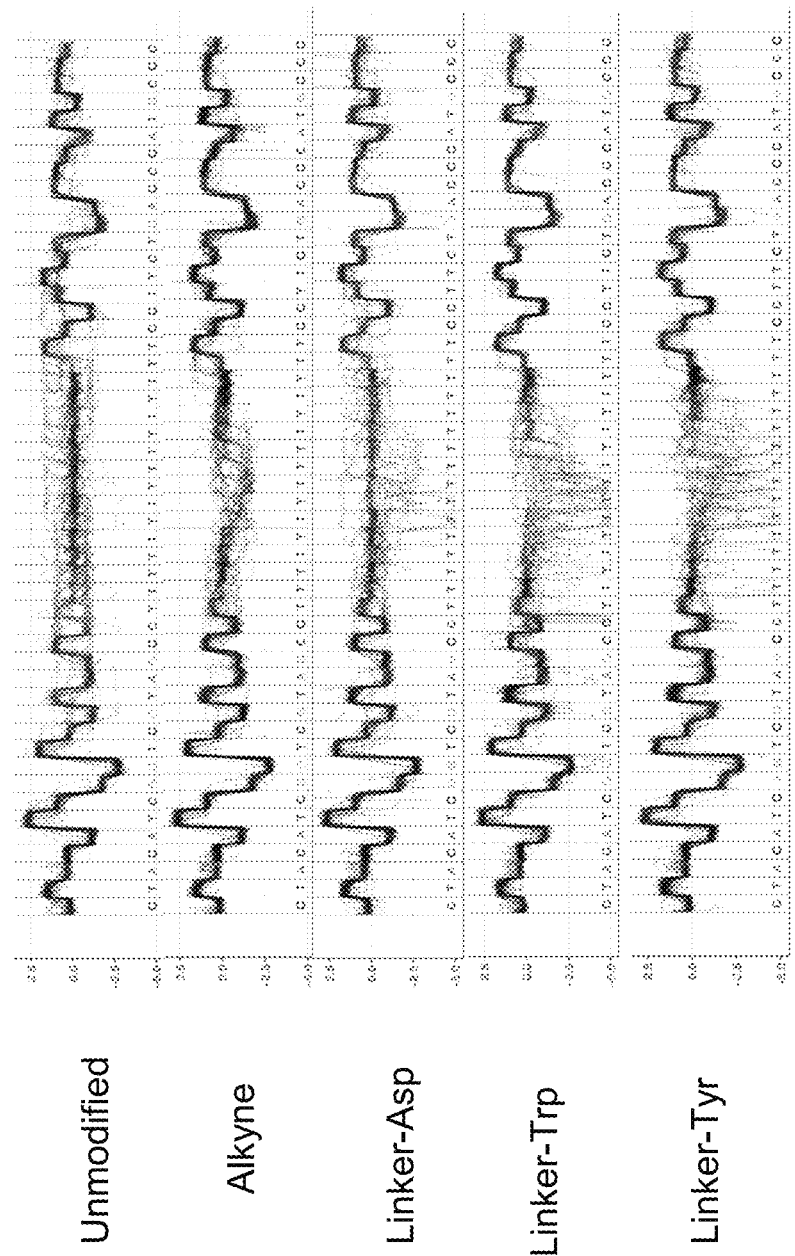
FIG. 6B shows example current traces obtained from a nanopore sequencing system of two control molecules and three amino acid-linker-polymerizable molecule complexes. Figure discloses SEQ ID NOS 3, 3, 3, 3, and 3, respectively, in order of appearance.
Figure 6C:
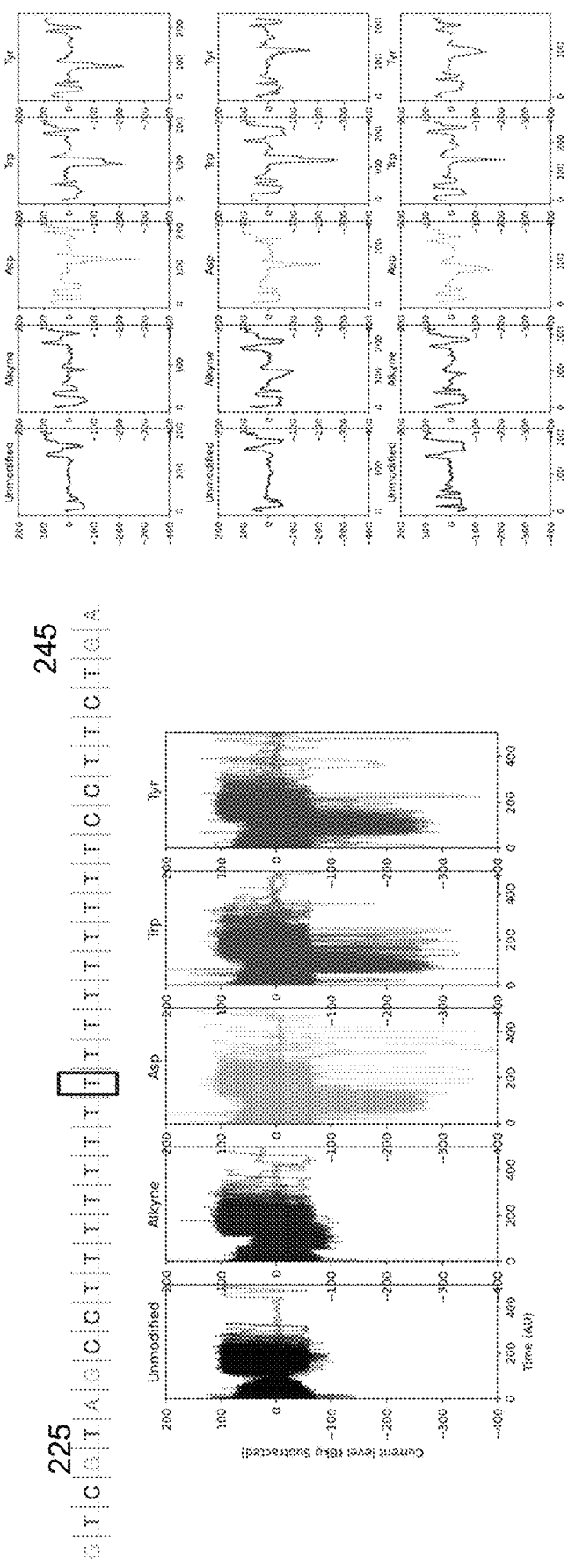
FIG. 6C shows example current traces as a function of time. Figure discloses SEQ ID NO: 2.
Figure 6D:
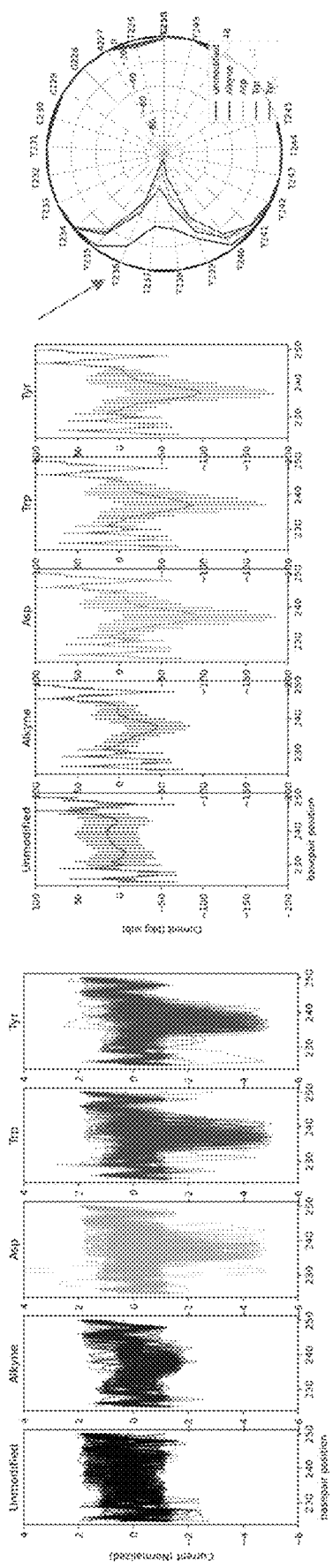
FIG. 6D shows example current traces as a function of base pair position. Figure discloses SEQ ID NO: 4.
Figure 6E:
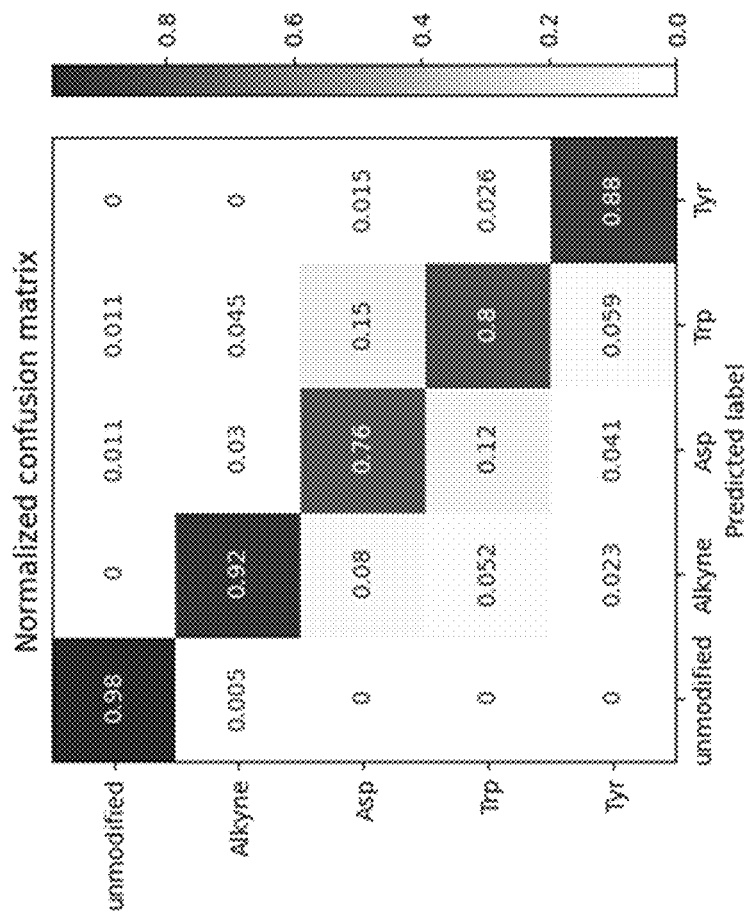
FIG. 6E shows example analyzed data of classification of the different molecule types.

Next, the amino acid-linker-polymerizable molecule conjugates are run through a nanopore sequencing system (Oxford Nanopore Technologies MinION) to interrogate whether the generated current signal can be assigned back to the amino acid type. The DNA backbone without modifications ("Unmodified") is used a baseline control, and the alkyne-linked DNA molecule ("Alkyne") is used as a control for the alkyne linker-specific current blockage. FIG. 6B shows the current traces and assigned nucleotide sequence of the DNA backbone. Of note, all of the different molecules do pass through the nanopore, and a discernible qualitative difference or perturbation in the current signal can be visualized from the amino acid-linker-polymerizable molecule conjugates (labeled as "Linker-Asp", "Linker-Trp", or "Linker-Tyr" that is not present in the current signal of the control molecules. FIG. 6C shows the current traces (measured current signal) as a function of time for the five conditions: Unmodified, Alkyne, Linker-Asp, Linker-Trp, and Linker-Tyr. All the combined overlayed traces for all of the reads from the nanopores in the device are shown on the left and the right shows three representative individual traces. FIG. 6D shows the current traces (measured current signal) as a function of base pair (nucleotide) position for the five samples: Unmodified, Alkyne, Linker-Asp, Linker-Trp, and Linker-Tyr. The combined overlayed traces for all of the reads from the nanopores in the device are shown on the left and the middle shows the mean signal and the error bars represent the standard deviation. The right-hand radial plot indicates the base or nucleotide position (along the radial axis) and the measured median current for each of the five tested conditions. Interestingly, the presence of the amino acid-linker complexes on the polymerizable molecules influences the current signal 2nt prior and 5nt after the conjugation site, suggesting that, in order to minimize the interference from neighboring amino acids, the polymerizable molecule spacing of the amino acid-linkers should be >8nt. Next, to determine how distinct the current traces for the amino acid-linker-polymerizable molecule complex are from the control molecules, a custom machine-learning algorithm model is used. FIG. 6E shows a normalized confusion matrix of the classified molecule (Unmodified, Alkyne, Linker-Asp, Linker-Trp, and Linker-Tyr) on the x-axis and the actual molecule on the y-axis. As can be visualized, classification of the correct molecule is achieved with modest accuracy.

Figure 7A:
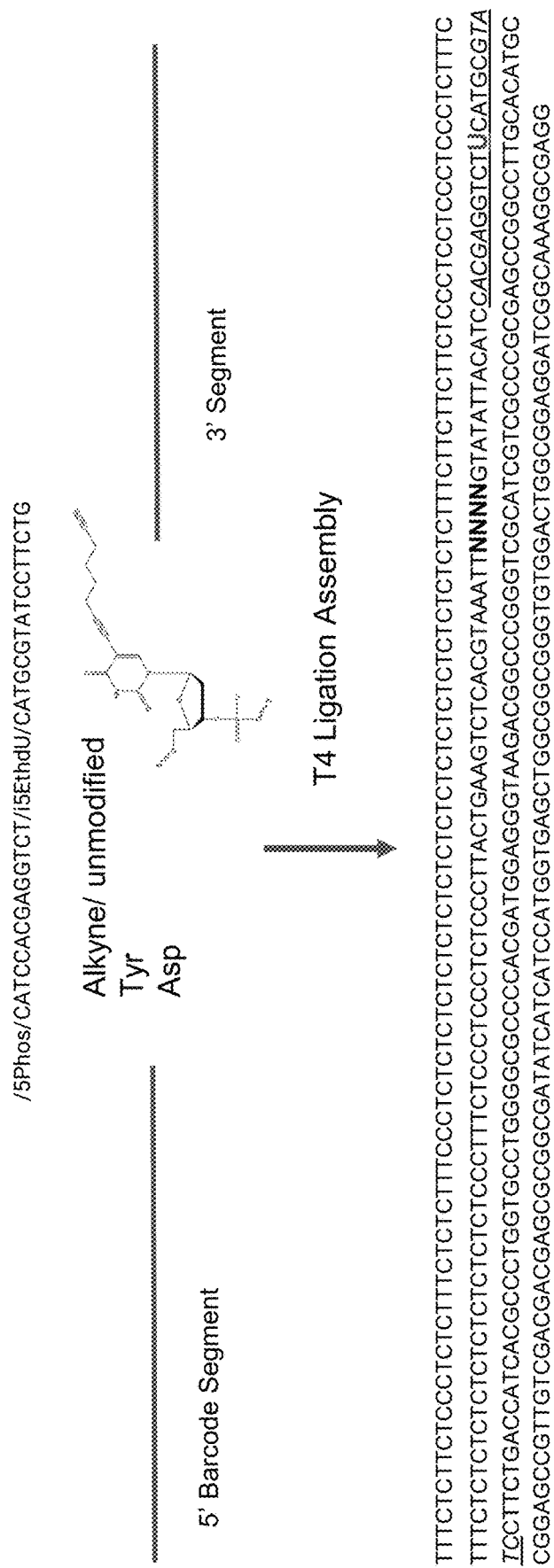
FIG. 7A shows a schematic of another example modified amino acid or derivative thereof comprising a polymerizable molecule. Figure discloses SEQ ID NOS 5 and 6, respectively, in order of appearance.

Example 3—Multiplexed Readout of Amino Acids Conjugated to Barcoded Polymerizable Molecules To determine whether nanopore detection of multiplexed information, e.g., of a modified amino acid or derivative thereof comprising a barcoded polymerizable molecule (e.g., nucleic acid barcode molecule) is possible, an amino acid-linker-barcoded polymerizable molecule complex is generated in a similar method as described above. The barcoded polymerizable molecule comprises a 4-nt barcode sequence that is located 5' of an alkyne linker that is located at a T236 position within a 450 nt ssDNA backbone, as schematically illustrated in FIG. 7A. Two types of ssDNA backbones are tested: the first comprises a poly-dT region, as described above and shown schematically in FIG. 6A, and the second comprises a mixed-base region, as shown in FIG. 7A. Next, an amino acid-linker complex is generated using a bifunctional linker, 1-(2-azidoethyl)-4-isothiocyanatobenzene, which comprises (1) a PITC moiety (amino acid reactive group) and (2) an azide moiety that is capable of reacting with the alkyne of the polymerizable molecule. The bifunctional linker is reacted with two different amino acids: Asp and Tyr via the PITC moiety, thereby generating an amino acid-linker complex (the same as those shown in FIG. 6A). The amino acid-linker complexes are then reacted with the alkyne-linked DNA molecules, thereby generating amino acid-linker-polymerizable molecule complexes.

Figure 7B:
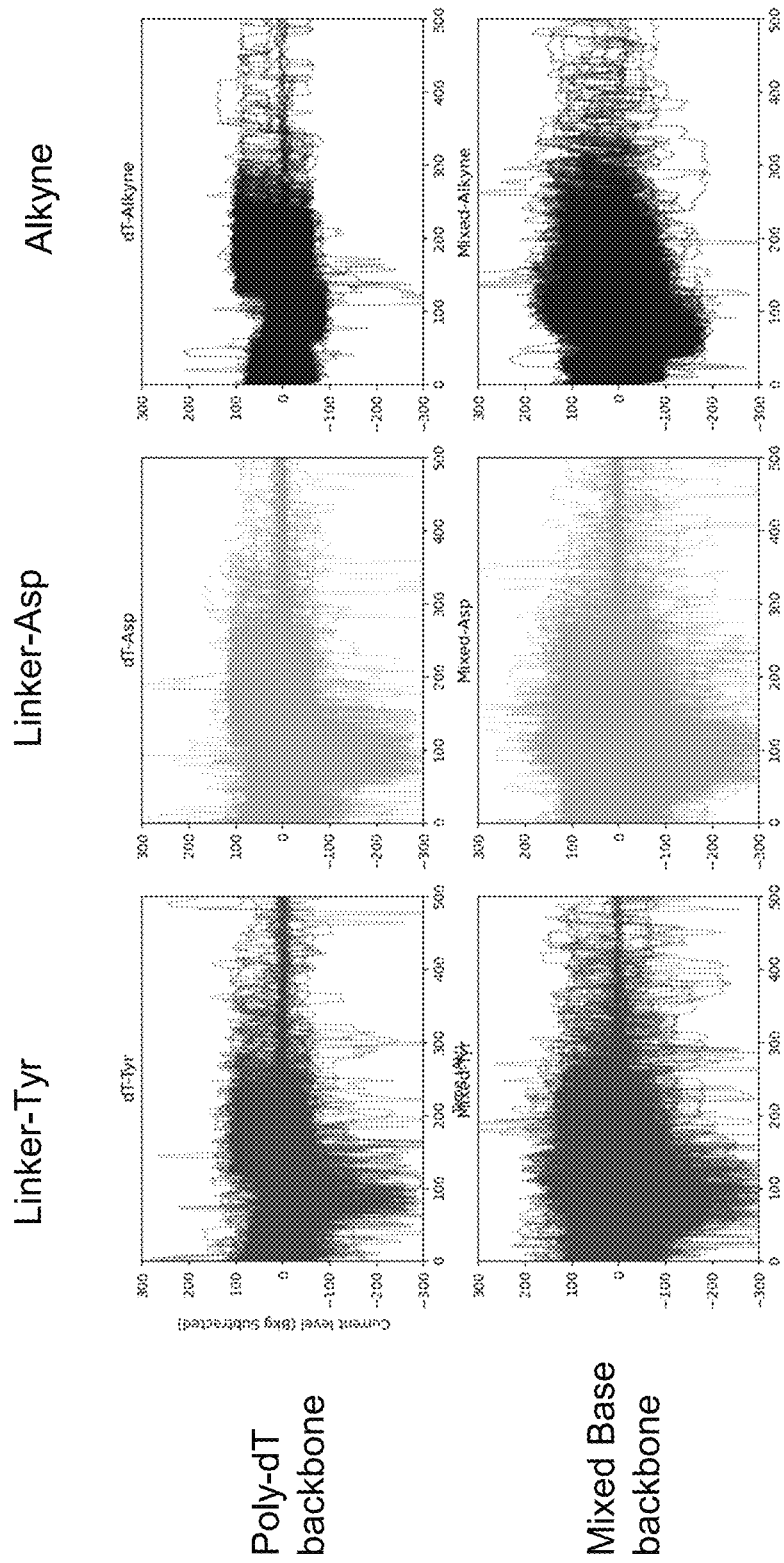
FIG. 7B shows example current traces as a function of time.
Figure 7C:
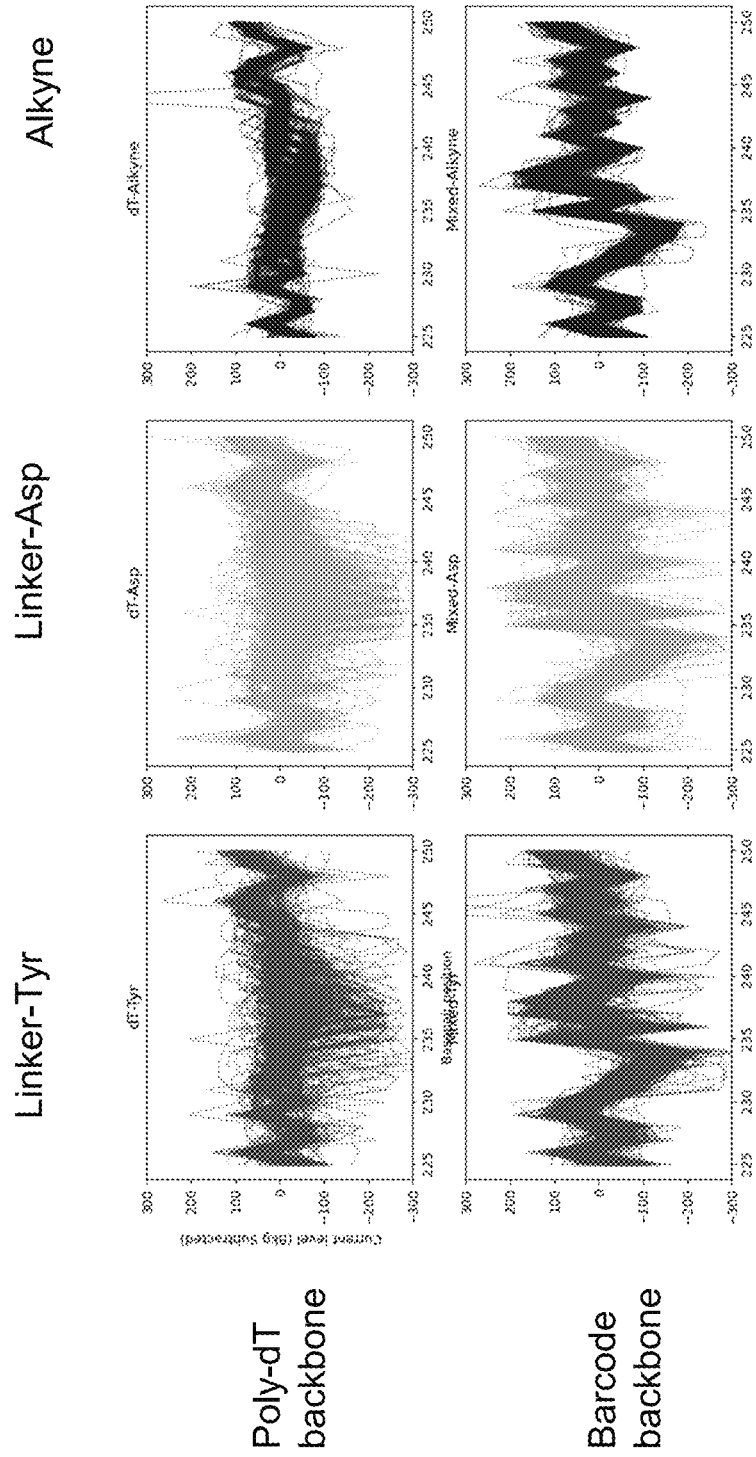
FIG. 7C shows example current traces as a function of base pair position.

Next, the amino acid-linker-polymerizable molecule complexes are run through a nanopore sequencing system (Oxford Nanopore Technologies MinION) to interrogate whether the generated current signal can be assigned back to the amino acid type (Asp or Tyr) and also if the barcode sequences of the barcoded polymerizable molecules are distinguishable. The alkyne-linked DNA molecule ("Alkyne") without an amino acid-linker complex is used as a control for the alkyne linker-specific current blockage. FIG. 7B shows the current traces (measured current signal) as a function of time (ms) of the amino acid-linker-polymerizable molecule complexes for the barcoded polymerizable molecules comprising the poly-dT sequence ("Poly-dT backbone") and the mixed-base sequence ("Mixed Base backbone"). A discernible difference or perturbation in the current signal can be visualized from the amino acid-linker-polymerizable molecule conjugates ("Linker-Asp" and "Linker-Tyr") for both types of polymerizable molecules. FIG. 7C shows the current traces (measured current signal) as a function of base (nucleotide) position for the three conditions: Linker-Tyr, Linker-Asp, and Alkyne (control) for both types of polymerizable molecules. Interestingly, the mixed-base polymerizable molecules result in more discernible current traces as compared to the poly-dT polymerizable molecules, suggesting that using mixed base polymerizable molecules instead of repeat nucleotide sequences may result in more distinguishable current traces. These results also suggest that multiplexed readout of both the DNA sequence and amino acid type is possible.

Figure 8A:
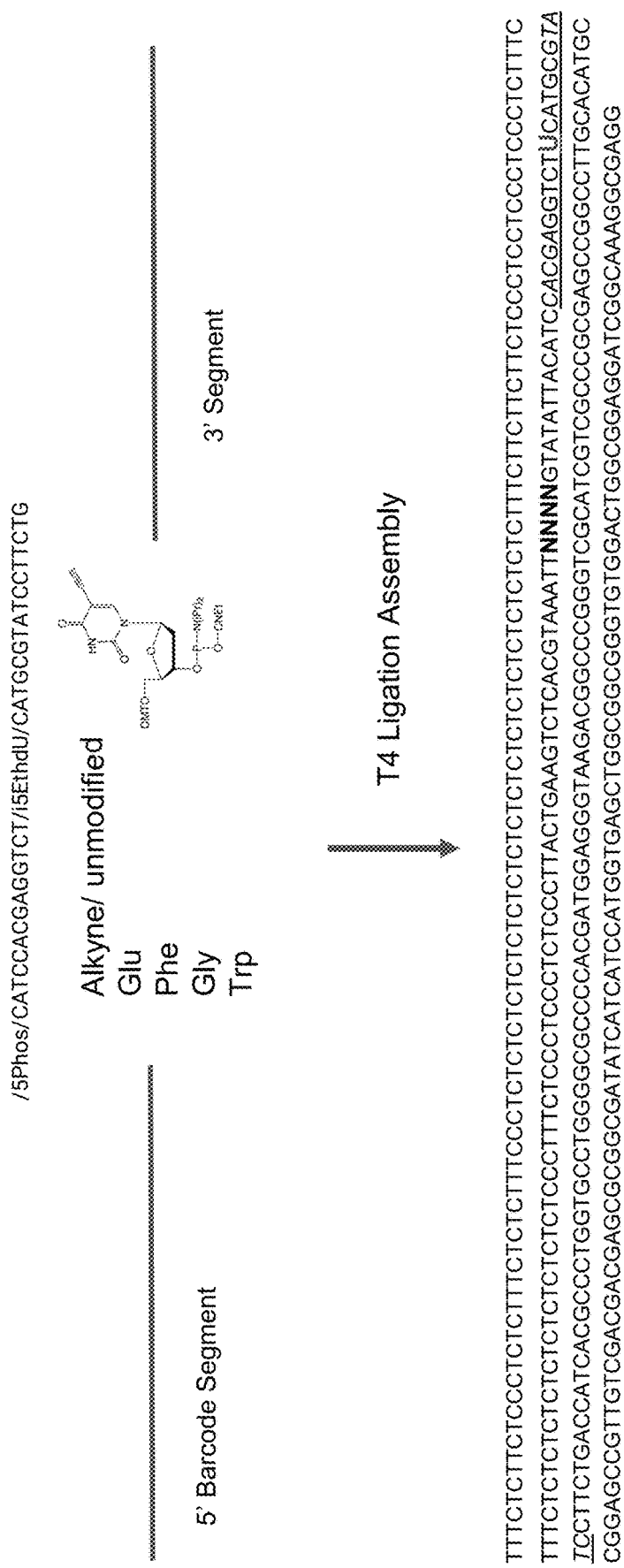
FIG. 8A shows a schematic of another example modified amino acid or derivative thereof comprising a polymerizable molecule. Figure discloses SEQ ID NOS 5 and 6, respectively, in order of appearance.

Example 4—Effect of Linker Length of Polymerizable Molecule on Nanopore Current Readout of Amino Acids Conjugated to Polymerizable Molecules As described herein, the polymerizable molecules of the modified amino acids or derivatives thereof (e.g., the AALC complexes or stacked AALC complexes or portions thereof) may comprise a linker that comprises a click chemistry moiety, which may couple to an amino acid-linker complex or to another linker comprising (i) a complementary click chemistry moiety and (ii) an amino acid reactive group. To determine whether the intramolecular distance between the click chemistry moiety and the polymerizable molecule (i.e., the linker length) can affect nanopore detection of a modified amino acid or derivative thereof, e.g., an amino acid-linker-polymerizable complex, two different amino acid-linker-polymerizable complexes are generated. The first amino acid-linker-polymerizable complex comprises an octadiynyl dU linker, as shown in FIG. 7A, and the second amino acid-linker-polymerizable complex comprises an ethynyl dU linker, as shown in FIG. 8A. Both of the amino acid-linker-polymerizable complexes comprise the same DNA backbone, which includes a 4-nt barcode sequence that is located 5' of the modified nucleotide (octadiynyl dU or ethynyl dU), which modified nucleotide is located at the 199nt position within a 400 nt DNA backbone. An amino acid-linker complex is generated using a bifunctional linker, 1-(2-azidoethyl)-4-isothiocyanatobenzene, which comprises (1) a PITC moiety (amino acid reactive group) and (2) an azide moiety that is capable of reacting with the alkyne of the polymerizable molecule. The bifunctional linker is reacted with two different amino acids: Asp and Tyr via the PITC moiety, thereby generating an amino acid-linker complex (the same as those shown in FIG. 6A). The amino acid-linker complexes are then reacted with the alkyne-linked DNA molecule via copper-catalyzed click chemistry, thereby generating an amino acid-linker-polymerizable molecule complex.

Figure 8B:
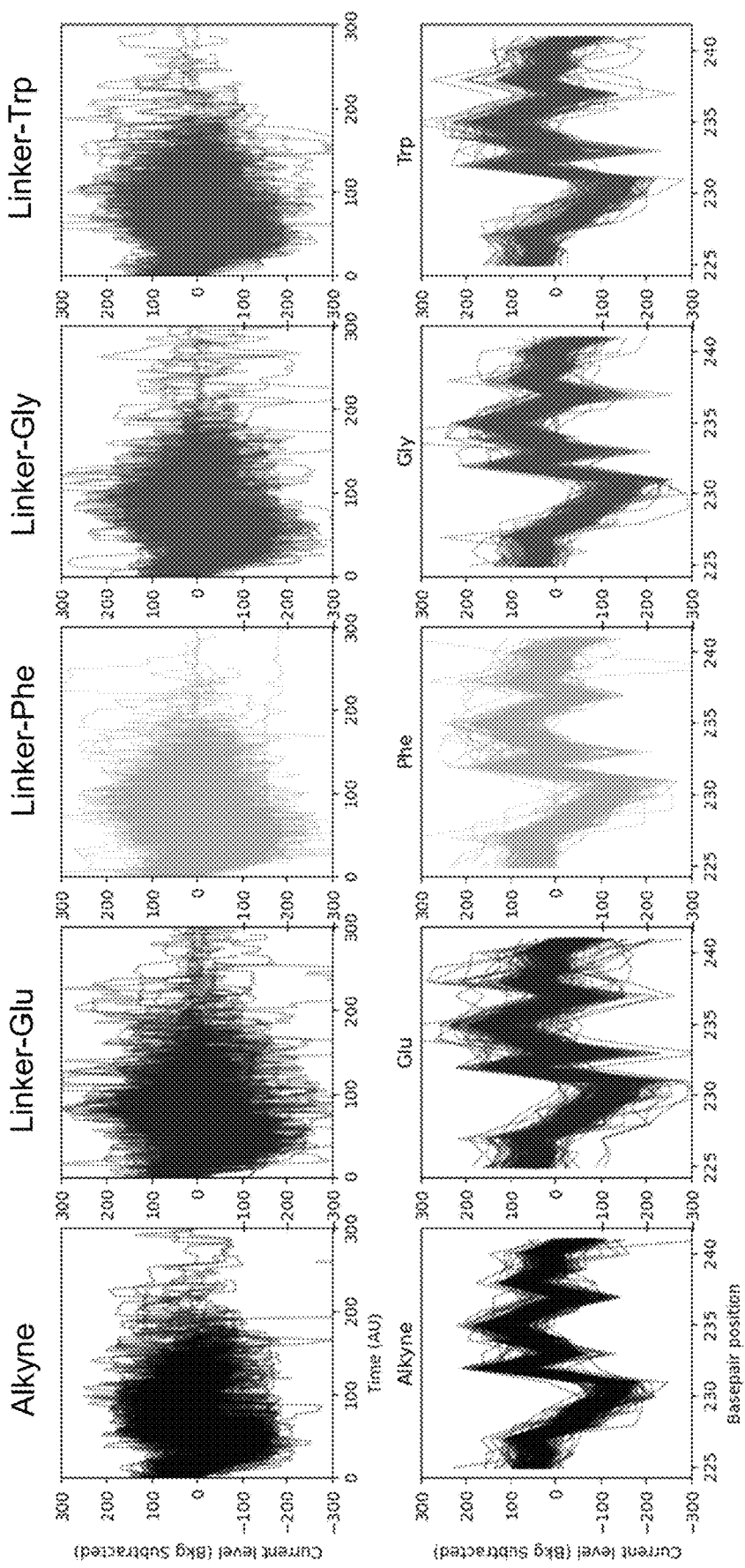
FIG. 8B shows example current traces as a function of time and base pair position.

FIG. 8B shows the current traces (measured current signal that is background subtracted) as a function of time (top) or base pair (nucleotide) position (bottom) of the amino acid-linker-polymerizable molecule complexes comprising the ethynyl dU linker for five different molecules: the control polymerizable molecule having the ethynyl dU linker but that does not comprise an amino acid-linker complex ("Alkyne"), and the amino acid-linker-polymerizable molecule complexes including Linker-Glu, Linker-Phe, Linker-Gly, and Linker-Trp. The current traces of the complexes comprising amino acids (Linker-Glu, Linker-Phe, Linker-Gly, and Linker-Trp) show a visible difference as compared to the control molecule that does not comprise an amino acid-linker complex.

Figure 8C:
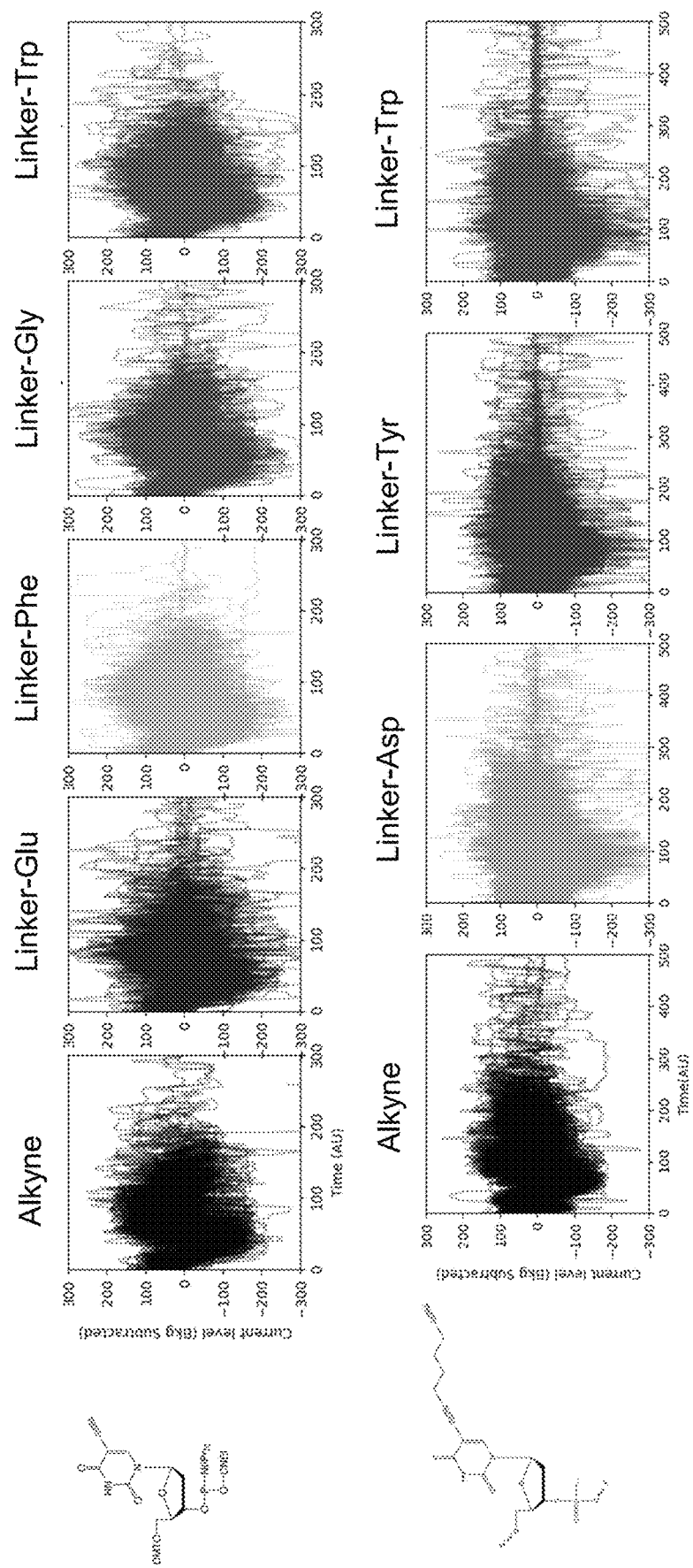
FIG. 8C shows example current traces as a function of time comparing two polymerizable molecules comprising different linkers.

FIG. 8C shows the current traces (measured current signal) as a function of time for the amino acid-linker-polymerizable molecule complexes comprising either the ethynyl dU linker (top) or the octadiynyl dU linker (bottom) for four or five different molecules: the control polymerizable molecule having the ethynyl dU linker or octadiynyl dU but that does not comprise an amino acid-linker complex ("Alkyne"), and the amino acid-linker-polymerizable molecule complexes including Linker-Glu, Linker-Phe, Linker-Gly, Linker-Trp (for the ethynyl dU linker) or Linker-Asp, Linker-Tyr, or Linker-Trp (for the octadiynyl dU linker). The current traces seem to suggest that the longer linker size (the octadiynyl dU) generates a greater contrast between the modified molecules (amino acid-linker-polymerizable molecule complexes) and unmodified control molecules (polymerizable molecules without an amino acid-linker complex coupled thereto).

Figure 8D:
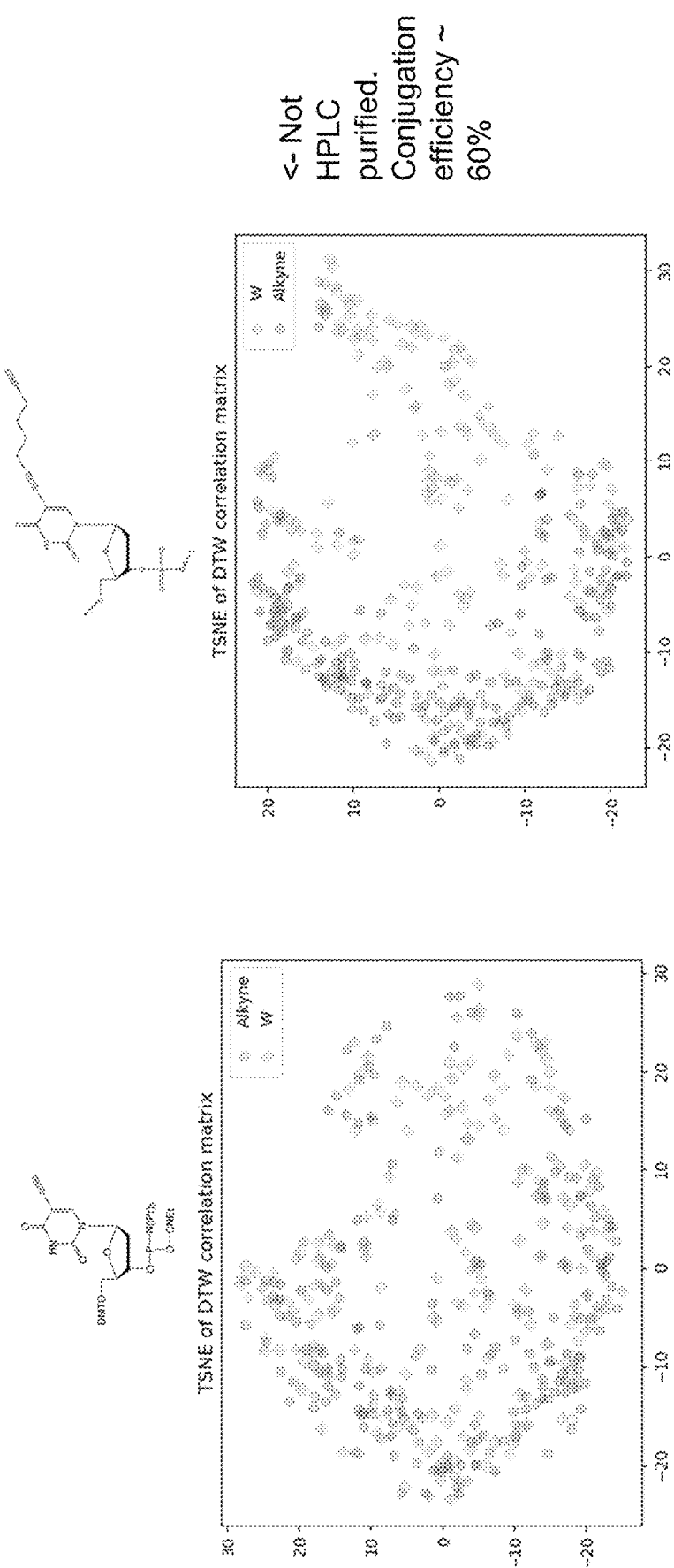
FIG. 8D shows a t-SNE plot of a dynamic-time warped correlation matrix.

FIG. 8D shows a shows t-SNE plots of a Dynamic-time warping (DTW) correlation matrix comparing the nanopore current traces of the amino acid-linker-polymerizable molecule complexes comprising either the ethynyl dU linker (left) or the octadiynyl dU (right) linker, as compared to a control polymerizable molecule having the ethynyl dU linker or octadiynyl dU linker but not an amino acid-linker complex ("Alkyne"). The amino acid-linker-polymerizable molecule conjugates for Linker-Trp ("W") are shown. The t-SNE plot indicates that the longer linker size (the octadiynyl dU) generates a greater contrast between the modified (amino acid-linker-polymerizable molecule complexes, "W") and unmodified control molecules (polymerizable molecules without an amino acid-linker complex coupled thereto, "Alkyne").

Figure 9:
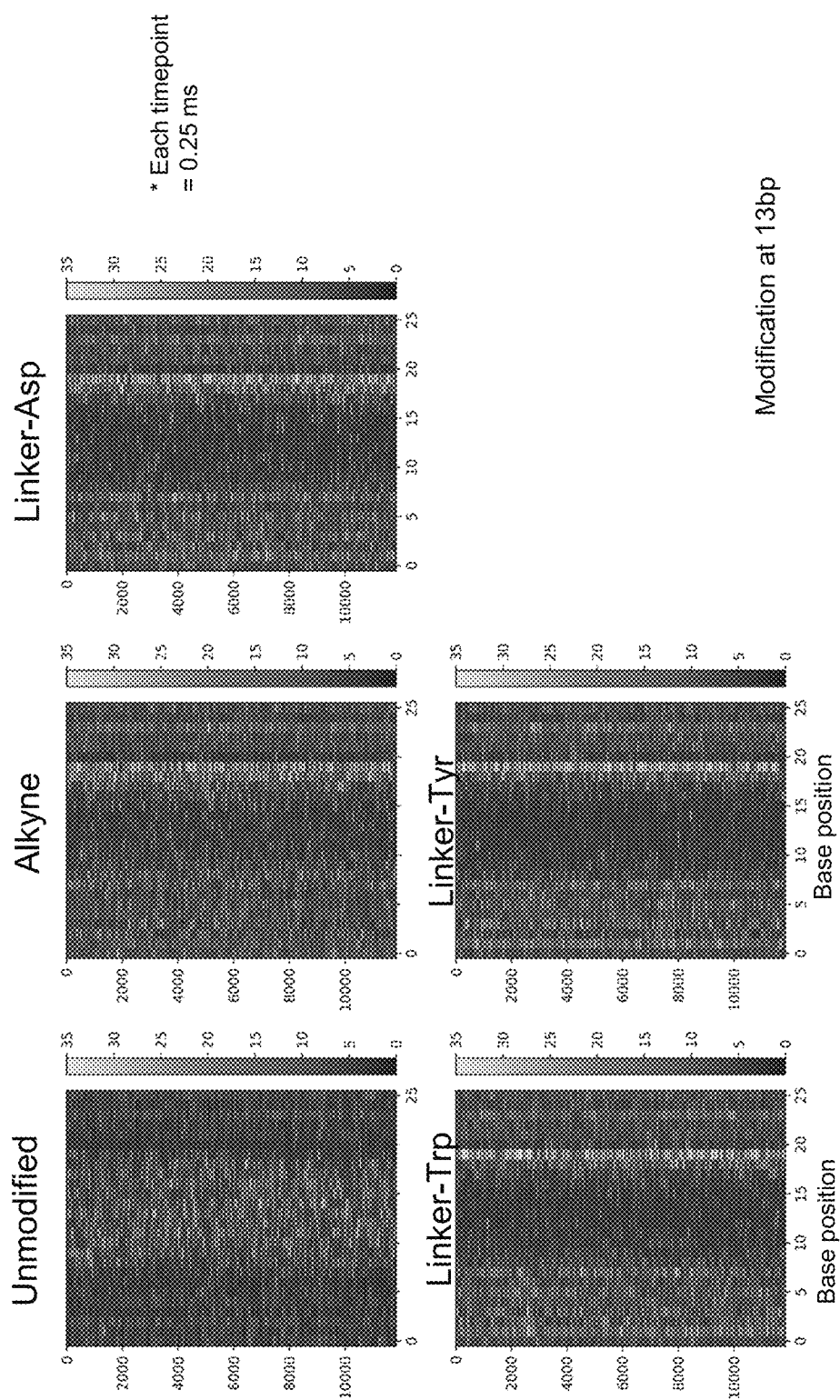
FIG. 9 shows example data on the dwell time of two control molecules and three amino acid-linker-polymerizable molecule complexes.

Example 5—Effect of Modified Amino Acids or Derivatives Thereof on Translocation Velocity To determine the effect of the modified amino acids or derivatives thereof (e.g., amino acids comprising polymerizable molecules, AALC complexes, stacked AALC complexes, or portions thereof) on the readout of a nanopore sequencer, the dwell time is measured. The dwell time of a base is the duration of time that a single base resides in the nanopore and corresponds to the translocation velocity of the molecule through the nanopore. Several amino acid-linker-barcoded polymerizable molecule conjugates are measured. The amino acid-linker-polymerizable molecules are synthesized, as described above, using an octadiynyl dU linker on the polymerizable molecule, as described above in illustrated schematically in FIG. 6A. The amino acid-linker-polymerizable molecule conjugates are run through a nanopore sequencing system (Oxford Nanopore Technologies MinION) to interrogate whether modifications to the polymerizable molecules, e.g., addition of an amino acid-linker complex, influences the translocation velocity. The DNA backbone without modifications ("Unmodified") is used a baseline control, and the alkyne-linked DNA molecule ("Alkyne") is used as a control for the alkyne linker-specific current blockage. FIG. 9 shows a heat map of the measured dwell times of the control molecules and three different amino acid-linker-polymerizable molecule complexes (labeled as "Linker-Asp", "Linker-Trp", or "Linker-Tyr"). The x-axis represents the base pair position, which is truncated to show the 25 nt region that comprises and flanks the poly-dT sequence, with the alkyne linker present on the 13nt position. The y-axis represents each of the individual current traces. The relative intensity of each time point indicates the relative dwell time in timepoints (each corresponding to 0.25 ms). Notably, the measured dwell time is different across the amino acid-linker-polymerizable molecule complexes, as compared to the control molecules. Interestingly, the modification (addition of an alkyne linker or an alkyne linker that is conjugated to an amino acid-linker complex) seems to affect the dwell time of the DNA backbone at several locations, including at base pair positions 0-5 and 10-25 that flank the modification site, suggesting that some molecular stretching and contraction may occur and that the presence of the AALC might affect a large window of nucleotides around the modifications site.

Example 6—Nanopore Sequencing of Stacked Amino Acid-Polymerizable Complexes

Figure 10A:
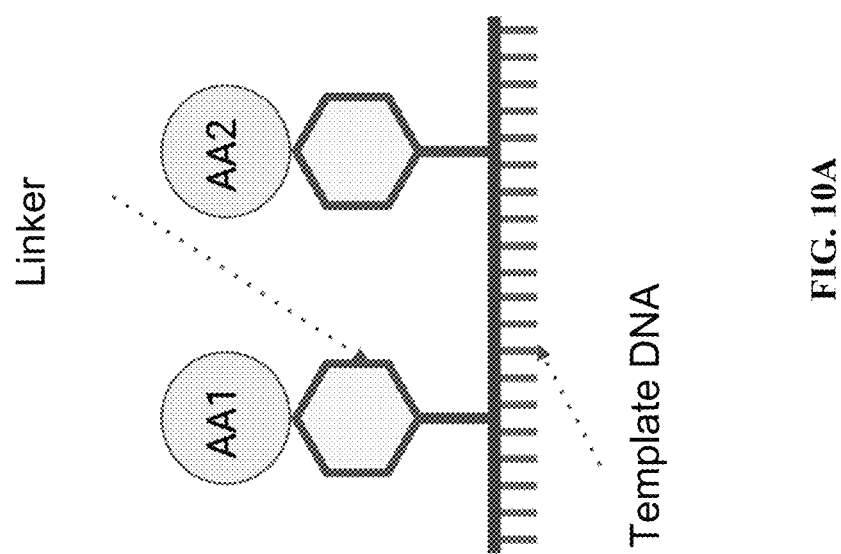
FIG. 10A shows a schematic of a stacked amino acid-linker-polymerizable molecule complex described herein.
Figure 10B:
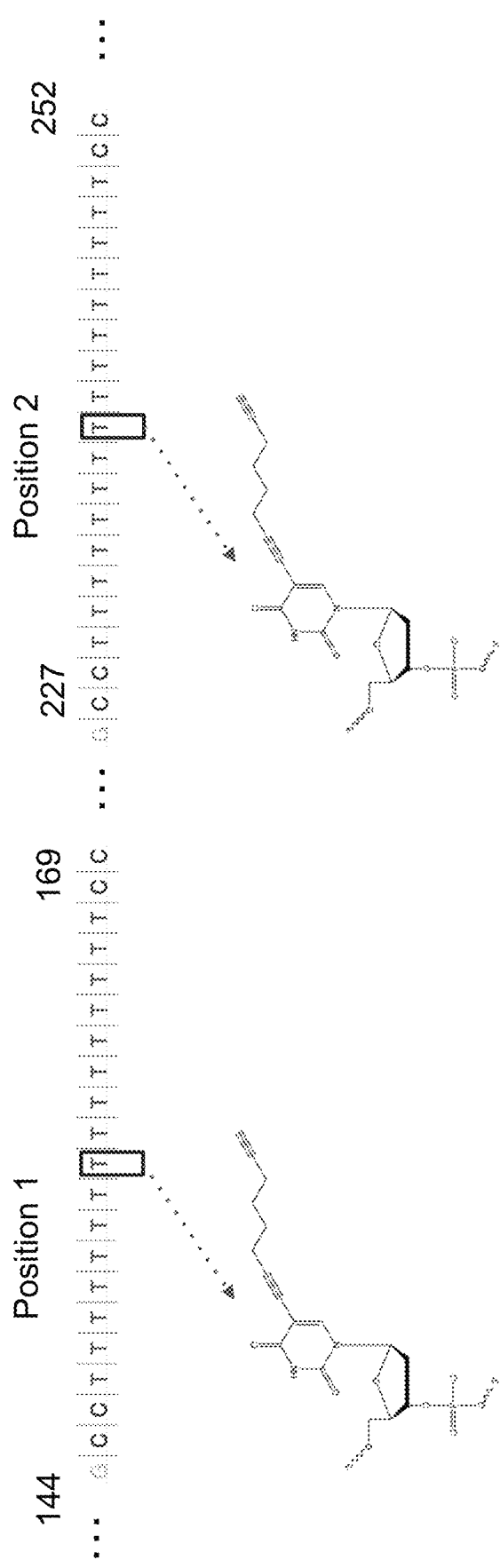
FIG. 10B shows a schematic of an example model stacked amino acid-linker-polymerizable molecule complex. Figure discloses SEQ ID NOS 7 and 7, respectively, in order of appearance.

To determine whether nanopore detection of a modified amino acid or derivative thereof, e.g., a stacked AALC complex or portion thereof, is possible, an amino acid-linker-polymerizable molecule conjugate comprising two amino acids is first generated, as illustrated schematically in FIG. 10A. The polymerizable molecule comprises an alkyne linker (octadiynyl dU) at two positions within a 252-nt DNA backbone, as shown in FIG. 10B. Next, amino acid-linker complexes are generated using a bifunctional linker, 1-(2-azidoethyl)-4-isothiocyanatobenzene, which comprises (1) a PITC moiety (amino acid reactive group) and (2) an azide moiety that is capable of reacting with the alkyne of the polymerizable molecule. The bifunctional linker is reacted with three different amino acids: Asp, Trp, and Tyr via the PITC moiety, thereby generating an amino acid-linker complex, also shown in the bottom panel of FIG. 6A. The amino acid-linker complexes are then reacted with the alkyne-linked DNA molecules, thereby generating a dual-amino acid-linker-polymerizable molecule complexes comprising a pair of amino acids. FIG. 10C shows a table of the different pairs of amino acids conjugated at the first linker position or the second linker position. The DNA backbone without modifications ("Unmodified") is used a baseline control, and the alkyne-linked DNA molecule ("Alkyne") is used as a control for the alkyne linker-specific current blockage.

Figure 10D:
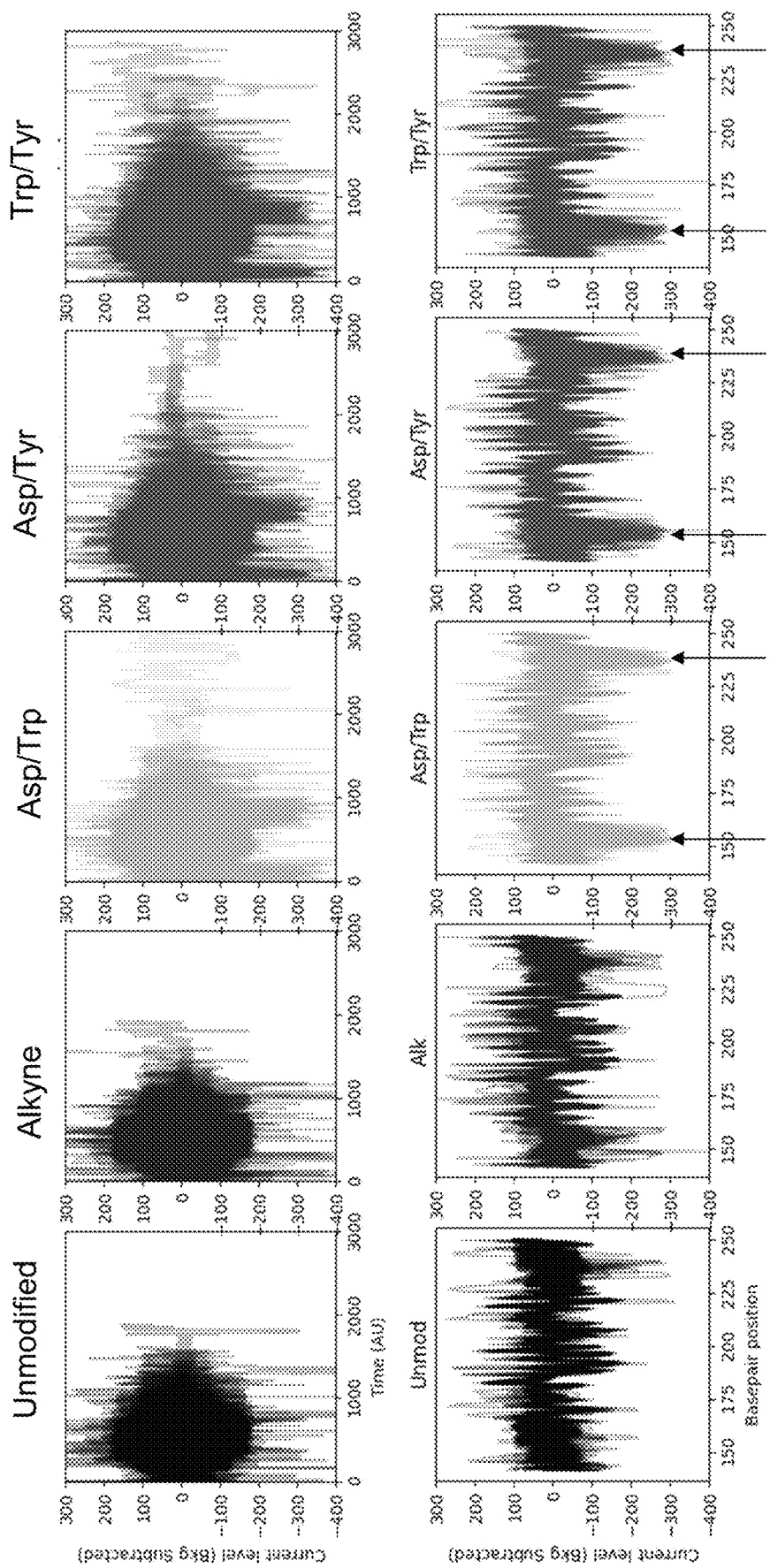
FIG. 10D shows example current traces as a function of time and base pair position.
Figure 10E:
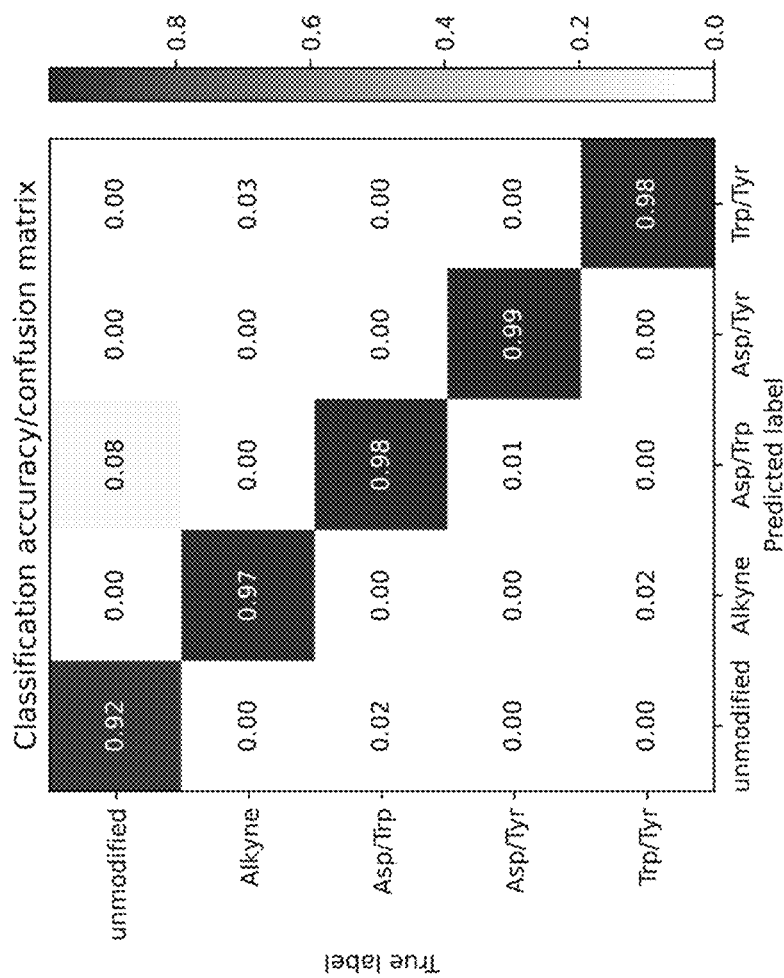
FIG. 10E shows example classification data of the different molecule types.

Next, the dual-amino acid-linker-polymerizable molecule conjugates are run through a nanopore sequencing system (Oxford Nanopore Technologies MinION) to interrogate whether the generated current signal can be assigned back to the two amino acid types present in the dual-amino acid-linker-polymerizable molecule complexes. FIG. 10D shows the current traces (measured current signal) as a function of time (top) or base pair position (bottom). Similar to the amino acid-linker-polymerizable molecule complexes comprising a single amino acid, the dual-amino acid-linker-polymerizable molecule complexes comprising two amino acids pass through the nanopore, and a discernible difference or perturbation in the current signal can be visualized from each amino acid at their respective positions (indicated with arrows) within the dual-amino acid-linker-polymerizable molecule conjugates (labeled as "Asp/Trp", "Asp/Tyr", or "Trp/Tyr") that is not present in the current signal of the control molecules. Next, to determine how distinct the current traces for the dual-amino acid-linker-polymerizable molecule complexes comprising two amino acids is from the control molecules, a custom machine-learning algorithm model is used. FIG. 10E shows a normalized confusion matrix of the predicted molecule (Unmodified, Alkyne, Asp/Trp, Asp/Tyr, Trp/Tyr) on the x-axis and the actual molecule on the y-axis. As can be visualized, classification of the correct molecule is achieved with high accuracy, ranging from 92% to 98%. Altogether, these results indicate that processing of amino acids to generate modified amino acids comprising polymerizable molecules may be a viable approach for conducting highly accurate peptide sequencing using a nanopore or nanochannel approach.

Example 7—Temperature Modulation for Improving Current Signal-to-Noise Ratio

As described herein, a translocation velocity of a modified amino acid or derivative thereof may differ from that of an unmodified amino acid, and similarly, a translocation velocity of a modified amino acid or derivative thereof comprising a polymerizable molecule may differ from that of the polymerizable molecule without an amino acid coupled thereto. In one hypothesis, the translocation velocity of a molecule through a nanopore may be lowered by decreasing the temperature of the environment. To test this hypothesis, a polymerizable molecule without modifications (does not comprise an amino acid-linker complex) can be run through a nanopore sequencing system at ambient (room) temperature or on ice.

Figure 11A:
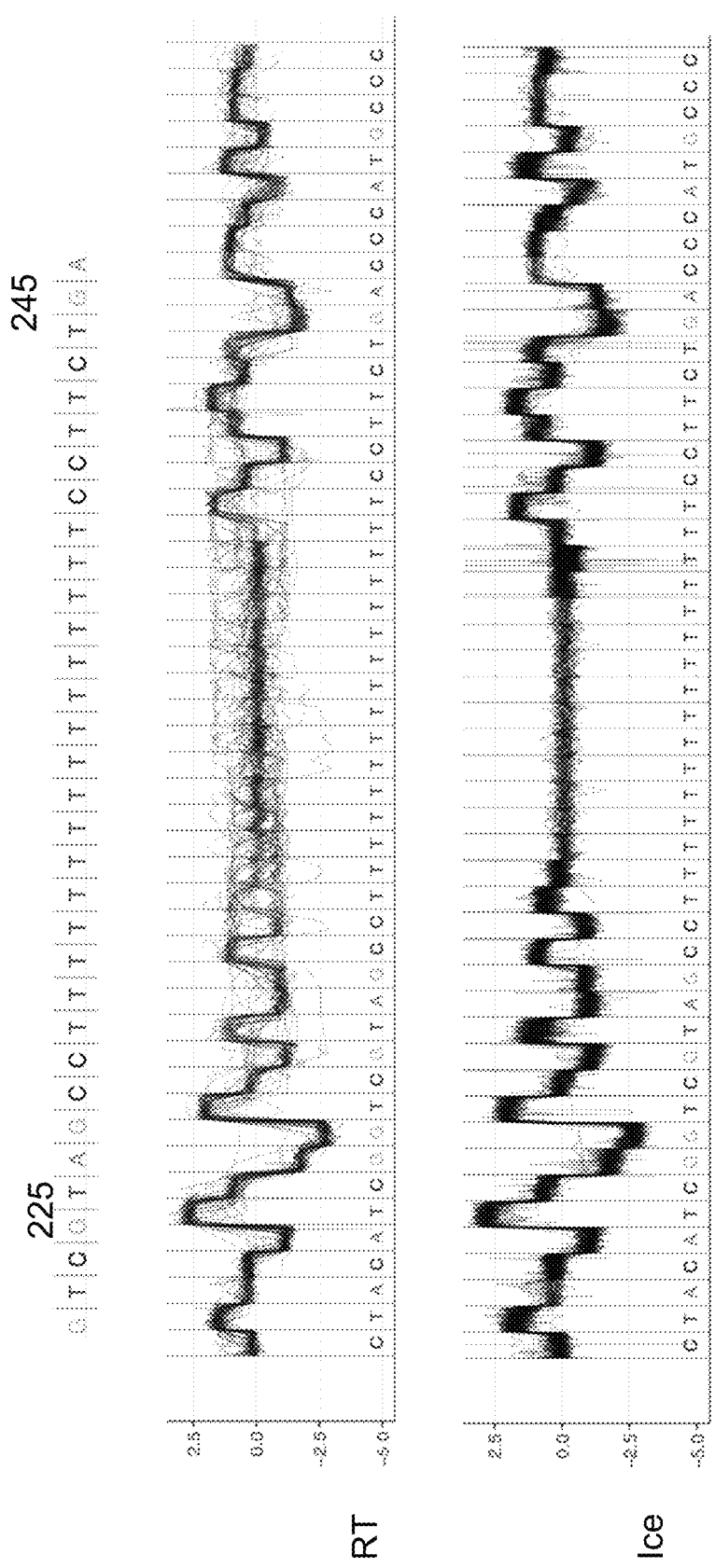
FIG. 11A shows example current traces obtained from a polymerizable molecule translocating through a nanopore sequencing system at different temperatures. Figure discloses SEQ ID NOS 4, 3 and 3, respectively, in order of appearance.

The polymerizable molecule includes a 450 nt dsDNA backbone that comprises a 16nt poly-dT sequence (SEQ ID NO: 1), as schematically illustrated in FIG. 11A (selected sequence from about −225 bp to −245 bp shown). The polymerizable molecule is run through a nanopore sequencing system (Oxford Nanopore Technologies MinION) to interrogate the effect of the temperature on the sequencing output. The measured temperature of the flow cell run at room temperature is 34 degrees Celsius, and the measured temperature of the flow cell run on ice is ~19-20 degrees Celsius. FIG. 11A shows the current traces (measured current signal) as a function of the base pair position and identified nucleotide of a selected sequence from the polymerizable molecule. Interestingly, the signal-to-noise ratio of the 16 nt poly-dT sequence (SEQ ID NO: 1) qualitatively appears higher.

Figure 11B:
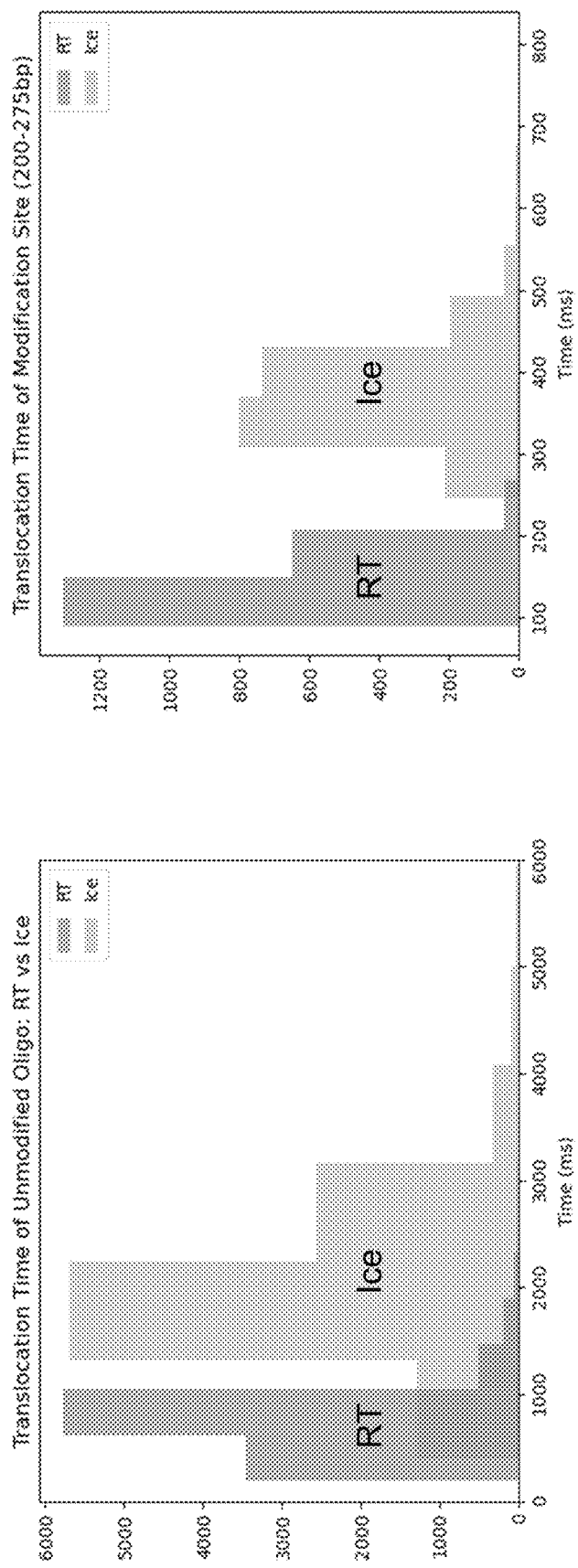
FIG. 11B shows histograms of the translocation duration of the molecules through the nanopore at the different temperatures.
Figure 11C:
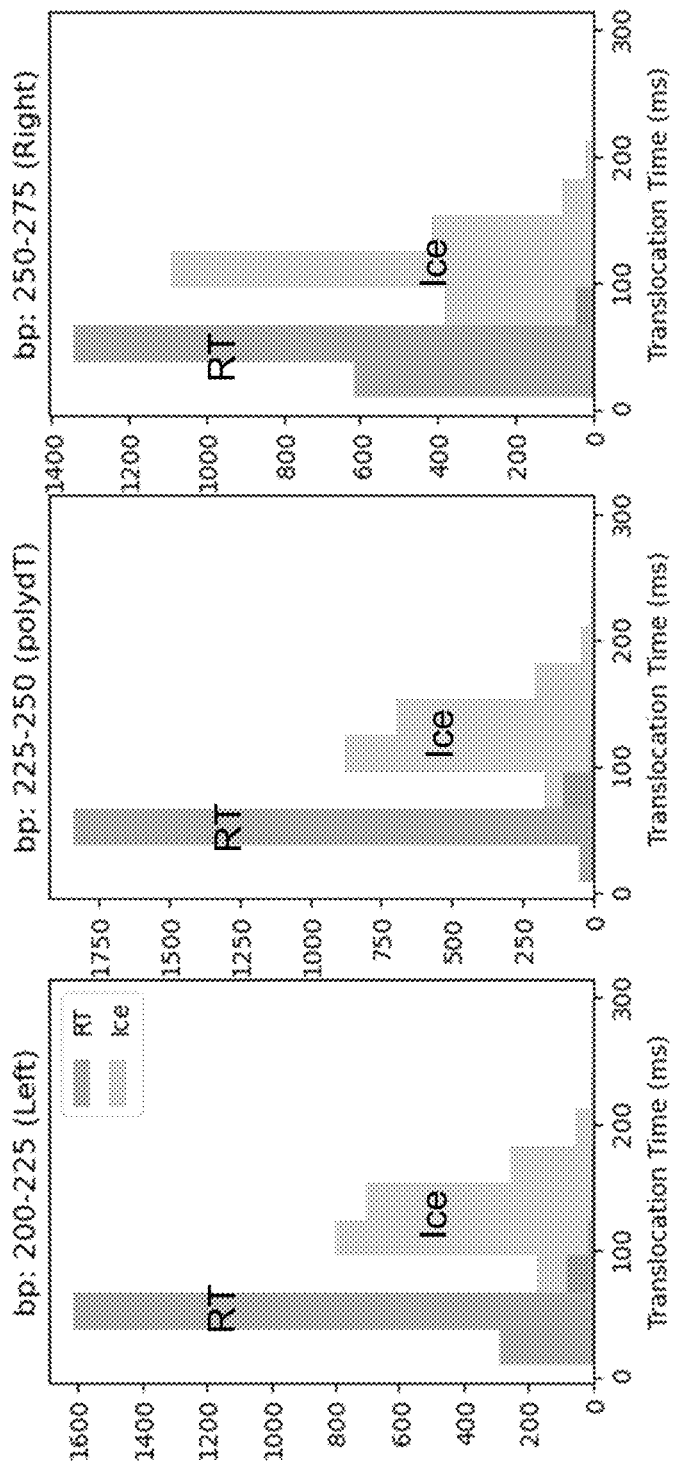
FIG. 11C shows histograms of the translocation durations of different sequences of the polymerizable molecule at the different temperatures.

FIG. 11B shows histograms of the translocation duration, which is a measure of the duration of time that the region or whole polymerizable molecule resides in the nanopore and corresponds to the translocation velocity of the region or whole polymerizable molecule. The translocation duration is measured in milliseconds (ms) of the polymerizable molecule for the two different temperature conditions (room temperature or ice). The left-hand plot shows the translocation durations of the entire polymerizable molecule and the right-hand plot shows the translocation durations of the selected site surrounding the 16nt poly-dT sequence (SEQ ID NO: 1) (200-275 nt position). As can be visualized from the histograms, the ice condition results in reduced translocation velocity (increased translocation duration) with greater variability or higher range of the measured duration values.

FIG. tIC shows histograms of the translocation duration in ms of the polymerizable molecule for the two different temperature conditions (room temperature or ice). The left-hand plot shows the translocation durations of the polymerizable molecule at the 200-225 nt position upstream of the 16nt poly-dT sequence (SEQ ID NO: 1). The middle plot shows the translocation durations for the selected site immediately adjacent to and encompassing the 16nt poly-dT sequence (SEQ ID NO: 1) (225-250 nt in position). The right-hand plot shows the translocation durations of the polymerizable molecule at the 250-275 nt position downstream of the 16nt poly-dT sequence (SEQ ID NO: 1). As can be visualized in all three plots, the ice condition results in reduced translocation velocity (increased translocation duration) with greater variability or higher range of the measured duration values for both the poly-dT region and adjacent regions.

Figure 11D:
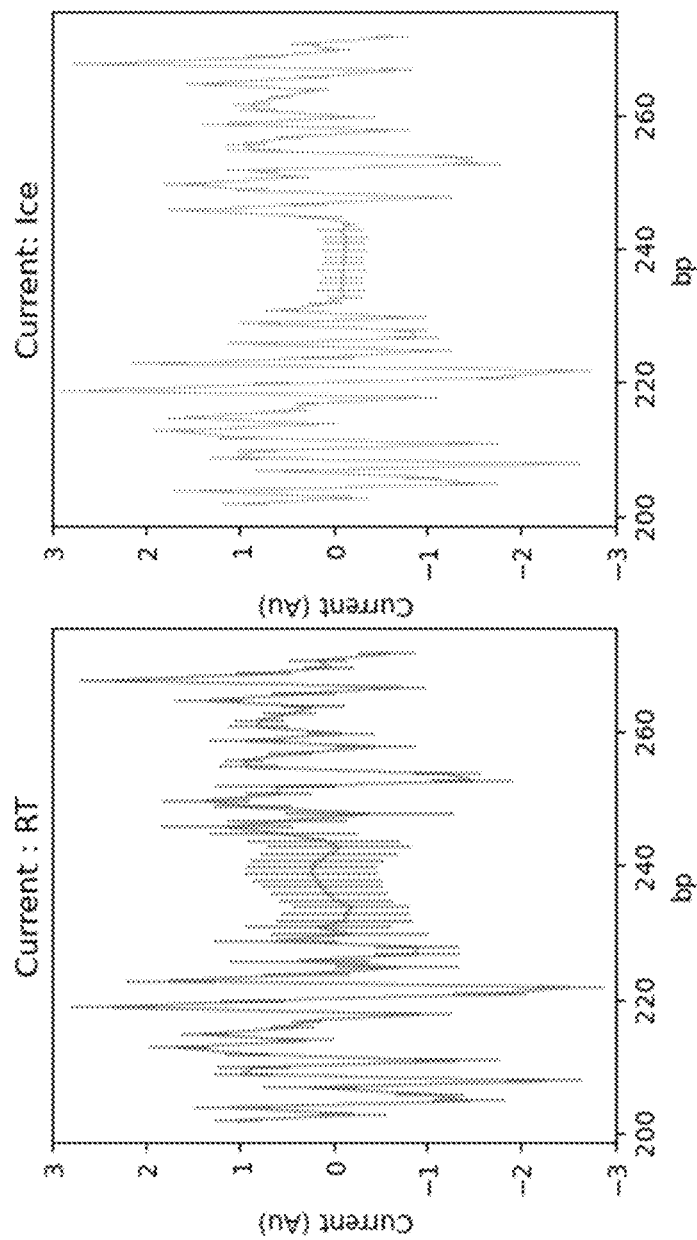
FIG. 11D shows example current traces of a portion of the polymerizable molecule.

FIG. 11D shows the current traces (measured current signal) as a function of base position from the 200-280 nt position. The left-hand plot shows the current trace for the room temperature condition and the right-hand plots shows the current trace for the ice condition. The ice condition improves the current signal-to-noise ratio, as evidenced by the decreased magnitude of the error bars in the poly-dT region (~225-245 nt region).

Figure 11E:
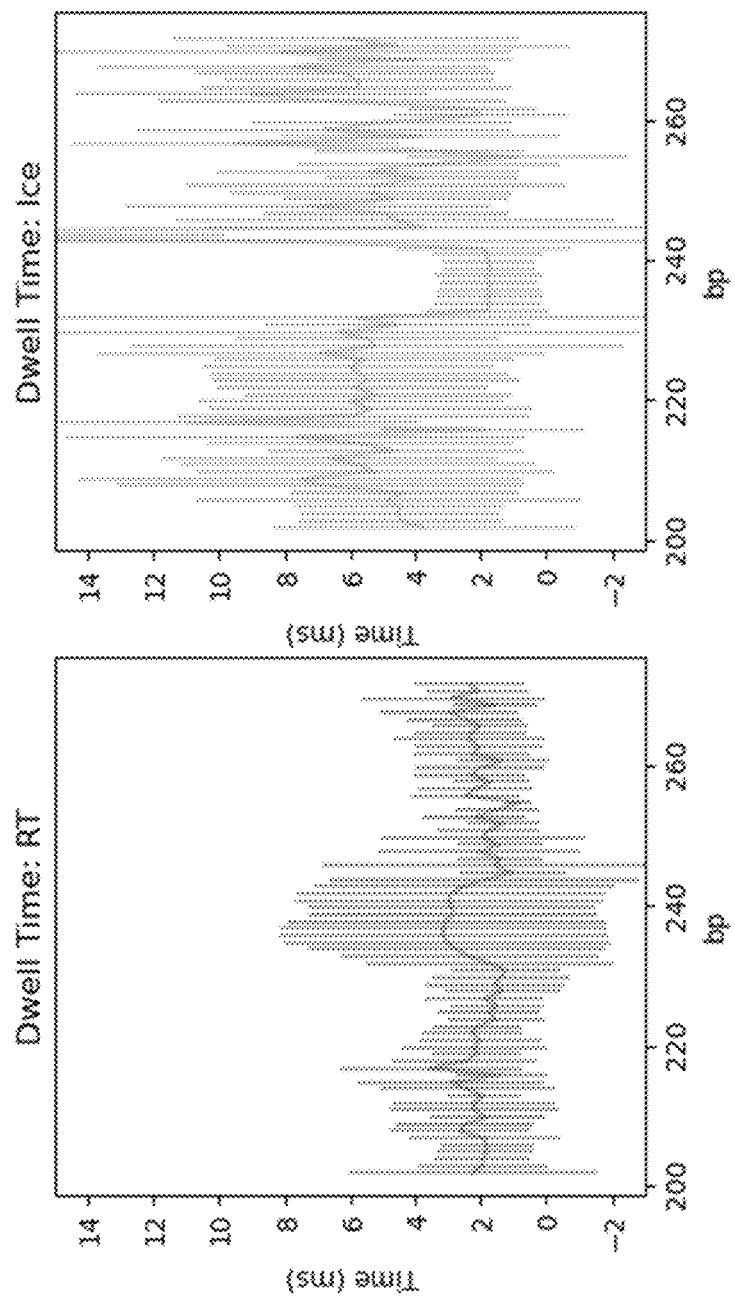
FIG. 11E shows example dwell times of a portion of the polymerizable molecule under the two different temperature conditions.

FIG. 11E shows the translocation duration in ms as a function of base position from the 200-280 nt position. The left-hand plot shows the current trace for the room temperature condition and the right-hand plots shows the current trace for the ice condition. Interestingly, while the ice condition results in an increased dwell time per base position, it also results in increased noise of the translocation duration except for the poly-dT region (~225-245 bp region).

Altogether, the results from FIGS. 11A-11E suggest that reducing the temperature may result in improved signal-to-noise ratio of current traces read out from polymerizable molecules from a nanopore sequencing system, which may be applicable for improved accuracy readout of modified amino acids or derivatives thereof.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of sequencing a peptide at single-amino acid resolution, comprising:
  (a) providing said peptide, a capture moiety comprising a first nucleic acid molecule, a linker, and a second nucleic acid molecule;
  (b) coupling said linker to a terminal amino acid of said peptide;
  (c) coupling said linker to said second nucleic acid molecule;
  (d) coupling said first nucleic acid molecule of said capture moiety to said second nucleic acid molecule;
  (e) cleaving said terminal amino acid from said peptide to yield an amino acid-linker-capture moiety (AALC) complex;
  (f) providing an additional linker comprising a third nucleic acid molecule, wherein said additional linker is capable of coupling to an additional amino acid of said peptide;
  (g) coupling said additional linker to said additional amino acid, thereby generating an additional amino acid-linker complex;
  (h) coupling said additional amino acid-linker complex to said AALC complex;
  (i) cleaving said additional amino acid from said peptide, thereby generating a stacked AALC complex;
  (j) translocating said stacked AALC complex through a nanopore or a nanogap;
  (k) during (j), measuring a current signal, thereby obtaining a measured current signal; and
  (l) using said measured current signal to determine an identity of said terminal amino acid and said additional amino acid, thereby sequencing said peptide.

2. The method of claim 1, wherein said linker comprises a reactive moiety.

3. The method of claim 2, wherein said second nucleic acid molecule comprises an additional reactive moiety capable of reacting with said reactive moiety of said linker, and wherein said coupling of (c) comprises reacting said reactive moiety with said additional reactive moiety.

4. The method of claim 3, wherein said second nucleic acid molecule comprises an additional linker comprising said additional reactive moiety, wherein said additional linker comprises a modified nucleobase and said additional reactive moiety comprises a click chemistry moiety.

5. The method of claim 1, wherein said capture moiety is affixed to a substrate.

6. The method of claim 5, wherein said substrate is substantially planar.

7. The method of claim 5, wherein said substrate is a bead.

8. The method of claim 1, wherein said capture moiety is coupled to said peptide.

9. The method of claim 1, wherein said first nucleic acid molecule or said second nucleic acid molecule comprises a DNA molecule, an RNA molecule, an XNA molecule, or modified variant thereof.

10. The method of claim 9, wherein said DNA molecule is single-stranded.

11. The method of claim 1, wherein said coupling of (d) is performed using a ligase.

12. The method of claim 1, wherein at least a portion of said first nucleic acid molecule is complementary to at least a portion of said second nucleic acid molecule.

13. The method of claim 12, wherein said coupling of (d) is performed by hybridizing said at least said portion of said first nucleic acid molecule to said at least said portion of said second nucleic acid molecule.

14. The method of claim 1, wherein said coupling of (d) is performed using a splint oligonucleotide, wherein said splint oligonucleotide comprises a first sequence complementary to at least a portion of said first nucleic acid molecule and a second sequence complementary to at least a portion of said second nucleic acid molecule.

15. The method of claim 1, wherein said first nucleic acid molecule of said capture moiety comprises a nucleic acid barcode molecule.

16. The method of claim 15, wherein said nucleic acid barcode molecule identifies said peptide.

17. The method of claim 1, wherein said terminal amino acid is an N-terminal amino acid.

18. The method of claim 1, wherein (b) occurs before (c).

19. The method of claim 1, wherein (c) occurs before (b).

20. The method of claim 1, further comprising, repeating (f)-(i) to generate said stacked AALC complex.

21. The method of claim 1, wherein said translocating of (j) occurs at a temperature below ambient temperature.

22. The method of claim 1, wherein said second nucleic acid molecule comprises a nucleic acid barcode molecule that comprises temporal information.

23. The method of claim 1, wherein said capture moiety comprises a cleavable moiety.

24. The method of claim 1, wherein said linker is a bifunctional linker.

25. The method of claim 1, wherein said linker comprises an amino acid reactive group and a click chemistry moiety.

26. The method of claim 1, wherein said cleaving of (e) or (i) is performed using treatment with acid.

27. The method of claim 26, wherein said acid is a Lewis acid.

28. The method of claim 1, wherein said peptide is derived from a biological sample.

29. The method of claim 1, wherein said terminal amino acid comprises a post-translational modification or a non-standard amino acid, and wherein (1) comprises identifying said post-translational modification or said non-standard amino acid.

30. The method of claim 1, wherein (a)-(i) are performed in absence of a substrate.

* * * * *

```
                           SEQUENCE LISTING

Sequence total quantity: 7
SEQ ID NO: 1             moltype = DNA  length = 16
FEATURE                  Location/Qualifiers
source                   1..16
                         mol_type = other DNA
                         organism = synthetic construct
SEQUENCE: 1
tttttttttt tttttt                                                     16

SEQ ID NO: 2             moltype = DNA  length = 33
FEATURE                  Location/Qualifiers
source                   1..33
                         mol_type = other DNA
                         organism = synthetic construct
modified_base            17
                         mod_base = OTHER
                         note = 5-(octa-1,7-diynyl)uracil
SEQUENCE: 2
gtcgtagcct tttttttttt tttttccttc tga                                  33

SEQ ID NO: 3             moltype = DNA  length = 50
FEATURE                  Location/Qualifiers
source                   1..50
                         mol_type = other DNA
                         organism = synthetic construct
SEQUENCE: 3
ctacatcggt cgtagccttt tttttttttt tttccttctg acccatgccc                50

SEQ ID NO: 4             moltype = DNA  length = 33
FEATURE                  Location/Qualifiers
source                   1..33
                         mol_type = other DNA
                         organism = synthetic construct
SEQUENCE: 4
gtcgtagcct tttttttttt tttttccttc tga                                  33

SEQ ID NO: 5             moltype = DNA  length = 31
FEATURE                  Location/Qualifiers
source                   1..31
                         mol_type = other DNA
                         organism = synthetic construct
modified_base            1
                         mod_base = OTHER
                         note = 5'-phosphorylated nucleotide
modified_base            15
                         mod_base = OTHER
                         note = 5-(octa-1,7-diynyl)uracil
SEQUENCE: 5
catccacgag gtcttcatgc gtatccttct g                                    31

SEQ ID NO: 6             moltype = DNA  length = 398
FEATURE                  Location/Qualifiers
source                   1..398
                         mol_type = other DNA
                         organism = synthetic construct
misc_difference          174
                         note = a, c, t, g, unknown or other
misc_difference          175
                         note = a, c, t, g, unknown or other
misc_difference          176
                         note = a, c, t, g, unknown or other
misc_difference          177
                         note = a, c, t, g, unknown or other
modified_base            200
                         mod_base = OTHER
                         note = 5-(octa-1,7-diynyl)uracil
SEQUENCE: 6
tttctcttct ccctctcttt ctctctttcc ctctctctct ctctctctct ctctctctct     60
ctctctctct ctttcttctt cttctccctc ctccctcct ctttctttct ctctctctct     120
ctctctctct ccctttctcc ctccctctcc cttactgaag tctcacgtaa attnnnngta    180
```

```
tattacatcc acgaggtctt catgcgtatc cttctgacca tcacgccctg gtgcctgggg    240
cgccccacga tggagggtaa gacggcccgg gtcgcatcgt cgcccgcgag ccggccttgc    300
acatgccgga gccgttgtcg acgacgagcg cggcgatatc atcatccatg gtgagctggc    360
ggcgggtgtg gactggcgga ggatcggcaa aggcgagg                            398

SEQ ID NO: 7            moltype = DNA  length = 21
FEATURE                 Location/Qualifiers
source                  1..21
                        mol_type = other DNA
                        organism = synthetic construct
modified_base           11
                        mod_base = OTHER
                        note = 5-(octa-1,7-diynyl)uracil
SEQUENCE: 7
gcctttttt tttttttttc c                                                21
```